United States Patent
Morgan et al.

(10) Patent No.: US 12,291,722 B2
(45) Date of Patent: May 6, 2025

(54) METHODS FOR MANUFACTURING ADOPTIVE CELL THERAPIES

(71) Applicant: 2seventy bio, Inc., Cambridge, MA (US)

(72) Inventors: Richard Morgan, Center Harbor, NH (US); Kevin Friedman, Medford, MA (US); Dawn Maier, North Reading, MA (US)

(73) Assignee: 2seventy bio, Inc., Cambridge, MA (US)

( * ) Notice: Subject to any disclaimer, the term of this patent is extended or adjusted under 35 U.S.C. 154(b) by 0 days.

(21) Appl. No.: 15/306,729

(22) PCT Filed: Apr. 24, 2015

(86) PCT No.: PCT/US2015/027518
§ 371 (c)(1),
(2) Date: Oct. 25, 2016

(87) PCT Pub. No.: WO2015/164745
PCT Pub. Date: Oct. 29, 2015

(65) Prior Publication Data
US 2017/0051252 A1    Feb. 23, 2017

Related U.S. Application Data

(60) Provisional application No. 61/984,558, filed on Apr. 25, 2014.

(51) Int. Cl.
| | |
|---|---|
| *C12N 5/0783* | (2010.01) |
| *A61K 35/12* | (2015.01) |
| *A61K 38/17* | (2006.01) |
| *A61K 39/00* | (2006.01) |
| *C12N 7/00* | (2006.01) |
| *C12N 15/86* | (2006.01) |

(52) U.S. Cl.
CPC .......... *C12N 5/0636* (2013.01); *A61K 38/177* (2013.01); *A61K 39/4611* (2023.05); *A61K 39/4631* (2023.05); *A61K 39/464412* (2023.05); *A61K 39/464417* (2023.05); *C12N 7/00* (2013.01); *C12N 15/86* (2013.01); *A61K 2035/124* (2013.01); *C07K 2319/00* (2013.01); *C12N 2501/2301* (2013.01); *C12N 2501/998* (2013.01); *C12N 2740/10043* (2013.01); *C12N 2740/15043* (2013.01); *C12N 2799/021* (2013.01); *C12N 2799/027* (2013.01); *C12N 2810/855* (2013.01)

(58) Field of Classification Search
None
See application file for complete search history.

(56) References Cited

U.S. PATENT DOCUMENTS

| | | |
|---|---|---|
| 5,585,089 A | 12/1996 | Queen et al. |
| 5,827,642 A | 10/1998 | Riddell et al. |
| 5,858,358 A | 1/1999 | June et al. |
| 5,883,223 A | 3/1999 | Gray |
| 5,994,136 A | 11/1999 | Naldini et al. |
| 6,005,079 A | 12/1999 | Casterman et al. |
| 6,013,516 A | 1/2000 | Verma et al. |
| 6,040,177 A | 3/2000 | Riddell et al. |
| 6,352,694 B1 | 3/2002 | June et al. |
| 6,534,055 B1 | 3/2003 | June et al. |
| 6,682,907 B1 | 1/2004 | Charneau et al. |
| 6,692,964 B1 | 2/2004 | June et al. |
| 6,797,514 B2 | 9/2004 | Berenson et al. |
| 6,867,041 B2 | 3/2005 | Berenson et al. |
| 6,887,466 B2 | 5/2005 | June et al. |
| 6,905,680 B2 | 6/2005 | June et al. |
| 6,905,681 B1 | 6/2005 | June et al. |
| 6,905,874 B2 | 6/2005 | Berenson et al. |
| 7,067,318 B2 | 6/2006 | June et al. |
| 7,144,575 B2 | 12/2006 | June et al. |
| 7,172,869 B2 | 2/2007 | June et al. |
| 7,175,843 B2 | 2/2007 | June et al. |
| 7,232,566 B2 | 6/2007 | June et al. |
| 7,754,482 B2 | 7/2010 | Riley et al. |
| 7,977,095 B2 * | 7/2011 | Bonyhadi ............ C12N 5/0636 435/372.3 |
| 9,034,324 B2 | 5/2015 | Kalled et al. |

(Continued)

FOREIGN PATENT DOCUMENTS

| | | |
|---|---|---|
| AU | 2013204923 A1 | 1/2014 |
| CN | 103442768 A | 12/2013 |

(Continued)

OTHER PUBLICATIONS

"Proleukin For Injection (Chiron)" 2000. 14 pages, downloaded from https://theodora.com/drugs/proleukin_for_injection_chiron.html on Apr. 28, 2018.*

(Continued)

*Primary Examiner* — Christopher M Babic
*Assistant Examiner* — Kimberly A Aron
(74) *Attorney, Agent, or Firm* — Foley Hoag LLP; Amy E. Mandragouras; Ariana D. Harris

(57) ABSTRACT

The invention provides compositions and methods for manufacturing adoptive cell therapies. In particular embodiments, the invention provides methods of harvesting populations of cells, isolating and activating PBMCs, expanding T cells, and administering the T cell therapeutic to a subject in need thereof.

35 Claims, 18 Drawing Sheets
Specification includes a Sequence Listing.

(56) References Cited

U.S. PATENT DOCUMENTS

| | | |
|---|---|---|
| 9,402,865 B2 | 8/2016 | Powell et al. |
| 9,499,629 B2 | 11/2016 | June et al. |
| 9,765,342 B2 | 9/2017 | Kochenderfer |
| 10,383,929 B2 | 8/2019 | Morgan et al. |
| 10,479,975 B2 | 11/2019 | Friedman |
| 10,624,960 B2 | 4/2020 | Morgan et al. |
| 10,639,358 B2 | 5/2020 | Morgan et al. |
| 10,639,359 B2 | 5/2020 | Morgan et al. |
| 10,646,558 B2 | 5/2020 | Morgan et al. |
| 10,774,343 B2 | 9/2020 | Morgan et al. |
| 11,020,466 B2 | 6/2021 | Morgan et al. |
| 11,351,236 B2 | 6/2022 | Morgan et al. |
| 11,382,965 B2 | 7/2022 | Morgan et al. |
| 11,479,755 B2 | 10/2022 | Friedman |
| 11,560,547 B2 | 1/2023 | Friedman |
| 11,633,463 B2 | 4/2023 | Morgan et al. |
| 12,006,369 B2 | 6/2024 | Morgan et al. |
| 12,029,784 B2 | 7/2024 | Morgan et al. |
| 12,109,234 B2 | 10/2024 | Quigley et al. |
| 2002/0115214 A1* | 8/2002 | June .................. A61K 35/17 435/372.3 |
| 2002/0177125 A1* | 11/2002 | Kamb ................ C07K 14/005 435/5 |
| 2003/0012783 A1 | 1/2003 | Kindsvogel |
| 2003/0095955 A1* | 5/2003 | Noessner .............. A61K 35/17 424/93.21 |
| 2003/0147869 A1 | 8/2003 | Riley et al. |
| 2006/0099177 A1* | 5/2006 | June .................. C07K 16/2809 424/93.1 |
| 2006/0121005 A1 | 6/2006 | Berenson et al. |
| 2008/0058019 A1 | 3/2008 | Natarajan et al. |
| 2008/0089863 A1 | 4/2008 | Mallet et al. |
| 2008/0274091 A1* | 11/2008 | Slepushkin ........ A01K 67/0271 424/93.21 |
| 2009/0137017 A1 | 5/2009 | Bonyhadi et al. |
| 2012/0148552 A1 | 6/2012 | Jensen |
| 2012/0301447 A1 | 11/2012 | Jensen |
| 2013/0004471 A1 | 1/2013 | Denaro et al. |
| 2013/0280220 A1* | 10/2013 | Ahmed .................. C12N 15/85 424/93.21 |
| 2013/0287748 A1* | 10/2013 | June ................ C07K 14/70521 424/93.21 |
| 2013/0288368 A1 | 10/2013 | June et al. |
| 2013/0309193 A1 | 11/2013 | Weinschenk et al. |
| 2014/0004132 A1 | 1/2014 | Brenner et al. |
| 2014/0086889 A1 | 3/2014 | Battaglia et al. |
| 2014/0087462 A1* | 3/2014 | Scheffold .............. A61K 35/17 435/375 |
| 2014/0322183 A1 | 10/2014 | Milone et al. |
| 2014/0322212 A1 | 10/2014 | Brogdon et al. |
| 2015/0024482 A1 | 1/2015 | Frigault et al. |
| 2017/0049819 A1 | 2/2017 | Friedman et al. |
| 2017/0051308 A1 | 2/2017 | Morgan et al. |
| 2017/0218337 A1 | 8/2017 | Friedman |
| 2017/0226216 A1 | 8/2017 | Morgan et al. |
| 2018/0085444 A1 | 3/2018 | Morgan et al. |
| 2018/0147271 A1 | 5/2018 | Morgan et al. |
| 2019/0194615 A1 | 6/2019 | Friedman |
| 2019/0388525 A1 | 12/2019 | Morgan et al. |
| 2019/0388526 A1 | 12/2019 | Morgan et al. |
| 2019/0388527 A1 | 12/2019 | Morgan et al. |
| 2019/0388528 A1 | 12/2019 | Morgan et al. |
| 2020/0079864 A1 | 3/2020 | Morgan et al. |
| 2020/0109365 A1 | 4/2020 | Friedman et al. |
| 2020/0330572 A1 | 10/2020 | Morgan et al. |
| 2021/0032658 A1 | 2/2021 | Morgan et al. |
| 2021/0038705 A1 | 2/2021 | Morgan et al. |
| 2021/0052711 A1 | 2/2021 | Morgan et al. |
| 2021/0077603 A1 | 3/2021 | Morgan et al. |
| 2021/0077604 A1 | 3/2021 | Morgan et al. |
| 2023/0193202 A1 | 6/2023 | Friedman |
| 2024/0091264 A1 | 3/2024 | Kochenderfer et al. |

FOREIGN PATENT DOCUMENTS

| | | | |
|---|---|---|---|
| EP | 0 324 154 A2 | 7/1989 | |
| EP | 0404097 A2 | 12/1990 | |
| EP | 2094837 A2 | 9/2009 | |
| JP | 2012-501180 | 1/2012 | |
| JP | 2013-522286 | 6/2013 | |
| JP | 2015513399 A | 5/2015 | |
| JP | 2017513891 A | 6/2017 | |
| JP | 2020015767 A | 1/2020 | |
| JP | 6671370 B2 | 3/2020 | |
| RU | 2477728 C1 | 3/2013 | |
| WO | WO 1993/001161 A1 | 1/1993 | |
| WO | WO 1994/004678 A1 | 3/1994 | |
| WO | WO 1994/025591 A1 | 11/1994 | |
| WO | WO 1995/028407 | 10/1995 | |
| WO | WO 1997/032970 A1 | 9/1997 | |
| WO | WO 2003/057171 A2 | 7/2003 | |
| WO | WO 2004/035768 A1 | 4/2004 | |
| WO | WO 2004/104185 A1 | 12/2004 | |
| WO | WO 2006/010834 A1 | 2/2006 | |
| WO | WO 2006/090291 A2 | 8/2006 | |
| WO | WO 2007/018318 A1 | 2/2007 | |
| WO | WO 2008/153742 A2 | 12/2008 | |
| WO | WO-2009058564 A2 | 5/2009 | |
| WO | WO 2009/091826 A2 | 7/2009 | |
| WO | WO 2010/104949 A2 | 9/2010 | |
| WO | WO 2011/041093 A1 | 4/2011 | |
| WO | WO 2011/057124 A1 | 5/2011 | |
| WO | WO 2011/114275 A1 | 9/2011 | |
| WO | WO 2012/079000 A1 | 6/2012 | |
| WO | WO 2012/099973 A2 | 7/2012 | |
| WO | WO 2012/129514 A1 | 9/2012 | |
| WO | WO 2012/140130 A1 | 10/2012 | |
| WO | WO 2012/163805 A1 | 12/2012 | |
| WO | WO 2012/170911 A2 | 12/2012 | |
| WO | WO 2013/070468 A1 | 5/2013 | |
| WO | WO 2013/126712 A1 | 8/2013 | |
| WO | WO-2013154760 A1 * | 10/2013 | ....... C07K 14/70517 |
| WO | WO 2014/011996 A1 | 1/2014 | |
| WO | WO 2014/031687 A1 | 2/2014 | |
| WO | WO 2014/039523 A1 | 3/2014 | |
| WO | WO 2014/048920 A1 | 4/2014 | |
| WO | WO 2014/055442 A1 | 4/2014 | |
| WO | WO 2014/055668 A1 | 4/2014 | |
| WO | WO 2014/055771 A1 | 4/2014 | |
| WO | WO 2014/059173 A2 | 4/2014 | |
| WO | WO 2014/089335 A2 | 6/2014 | |
| WO | WO 2014/099671 A1 | 6/2014 | |
| WO | WO 2014/100385 A1 | 6/2014 | |
| WO | WO 2014/130635 A1 | 8/2014 | |
| WO | WO 2015/120096 A2 | 8/2015 | |
| WO | WO 2015/123527 A1 | 8/2015 | |
| WO | WO 2015/158671 A1 | 10/2015 | |
| WO | WO 2015/164739 A1 | 10/2015 | |
| WO | WO 2015/164745 A1 | 10/2015 | |
| WO | WO 2015/164759 A2 | 10/2015 | |
| WO | WO 2015/188119 A1 | 12/2015 | |
| WO | WO 2016/014789 A2 | 1/2016 | |
| WO | WO 2016/094304 A2 | 6/2016 | |
| WO | WO 2016/164429 A1 | 10/2016 | |
| WO | WO 2017/099712 A1 | 6/2017 | |
| WO | WO-2021109977 A1 | 6/2021 | |

OTHER PUBLICATIONS

Mallone et al. Isolation and Preservation of Peripheral Blood Mononuclear Cells for Analysis of Islet Antigen-Reactive T Cell Responses: Position Statement of the T-Cell Workshop Committee of the Immunology of Diabetes Society. Clinical and Experimental Immunology, 2010. 163:33-49.*

Ledbetter et al. CD28 Ligation in T-Cell Activation: Evidence for Two Signal Transduction Pathways. Blood, 1990. 7(1):1531-1539.*

Vidan et al. Functional Integrity of the CD28 Co-Stimulatory Pathway in T Lymphocytes from Elderly Subjects. Age and Ageing, 1999. 28: 221-227.*

Wikipedia entry for White Blood Cell. Retrieved from the internet Sep. 26, 2023. https://en.wikipedia.org/wiki/White_blood_cell.*

(56) References Cited

OTHER PUBLICATIONS

The Reprocell Blog. Protocol for buffy coat preparation from whole blood. Retrieved from the internet Sep. 26, 2023. https://www.reprocell.com/blog/biopta/buffy-coat-preparation-from-whole-blood.*

The Reprocell Blog. Protocol for PBMC isolation from buffy coat samples. Retrieved from the internet Sep. 26, 2023. https://www.reprocell.com/blog/biopta/pbmc-isolation-from-buffy-coat-samples.*

Parel, et a. CD4+ CD8+ Double Positive (DP) T Cells in Health and Disease. Autoimmunity Reviews, 2004. (3)215-220.*

Alt and Caselmann. "Liver-directed gene therapy: molecular tools and current preclinical and clinical studies", Journal of Hepatology (1995); 23: 746-758.

Asheuer, M. et al., "Human CD34+Cells Differentiate into Microglia and Express Recombinant Therapeutic Protein", Proceedings of the National Academy of Sciences USA (2004); 101.10: 3557-3562.

Avery, Danielle T., et al. "BAFF selectively enhances the survival of plasmablasts generated from human memory B cells." The Journal of Clinical Investigation (2003); 112.2: 286-297.

Battaglia et al., "Rapamycin selectively expands CD4+CD25+ FoxP3+ regulatory T cells", Blood (2005); 105(12): 4743-4748.

Bellucci, Roberto, et al. "Graft-versus-tumor response in patients with multiple myeloma is associated with antibody response to BCMA, a plasma-cell membrane receptor." Blood (2005); 105.10: 3945-3950.

Bird, Robert E., et al. "Single-chain antigen-binding proteins." Science (1988); 242.4877: 423-427.

Borden and Kabat, "Nucleotide sequence of the cDNAs encoding the variable region heavy and light chains of a myeloma protein specific for the terminal nonreducing end of alpha(1----6)dextran", Proc Natl Acad Sci U S A (1987); 84(8): 2440-2443.

Brody and Crystal, "Adenovirus-mediated in vivo gene transfer", Ann. N. Y. Acad. Sci. (1994); 716: 90-101; discussion 101-3.

Carell, Thomas, et al. "A novel procedure for the synthesis of libraries containing small organic molecules." Angewandte Chemie International Edition in English (1994); 33.20: 2059-2061.

Carell, Thomas, et al. "A Solution-Phase Screening Procedure for the Isolation of Active Compounds from a Library of Molecules." Angewandte Chemie International Edition in English (1994); 33.20: 2061-2064.

Carpenito, Carmine, et al. "Control of large, established tumor xenografts with genetically retargeted human T cells containing CD28 and CD137 domains." Proceedings of the National Academy of Sciences USA (2009); 106.9: 3360-3365.

Carpenter, Robert O., et al. "B-cell maturation antigen is a promising target for adoptive T-cell therapy of multiple myeloma." Clinical Cancer Research (2013); 19.8: 2048-2060.

Challita, P. et al., "Multiple modifications in cis elements of the long terminal repeat of retroviral vectors lead to increased expression and decreased DNA methylation in embryonic carcinoma cells." J Virol. (1995); 69(2): 748-755.

Chan, W.K., et al. "Chimeric antigen receptor-redirected CD45RA-negative T cells have potent antileukemia and pathogen memory response without graft-versus-host activity." Leukemia (2015); 29(2): 387-395 (2015).

Chaudhary, Vuay K., et al. "A rapid method of cloning functional variable-region antibody genes in *Escherichia coli* as single-chain immunotoxins." Proceedings of the National Academy of Sciences (1990); 87.3: 1066-1070 (and correction).

Chiu, April, et al. "Hodgkin lymphoma cells express TACI and BCMA receptors and generate survival and proliferation signals in response to Baff and April." Blood (2007); 109.2: 729-739.

Cho, Charles Y., et al. "An unnatural biopolymer." Science (1993); 261: 1303-1304.

Chothia and Lesk, "Canonical structures for the hypervariable regions of immunoglobulins", J Mol Biol (1987); 196(4): 901-917.

Chothia, C. et al., "Conformations of immunoglobulin hypervariable regions", Nature (1989); 342(6252):877-883.

Clever, J. et al., "RNA Secondary Structure and Binding Sites for gag Gene Products in the 5' Packaging Signal of Human Immunodeficiency Virus Type 1." J. of Virology (1995); 69(4): 2101-2109.

Cooper, Laurence JN, et al. "T-cell clones can be rendered specific for CD19: Toward the selective augmentation of the graft-versus-B-lineage leukemia effect." Blood (2003); 101.4: 1637-1644.

Cribbs, A.P., et al., "Simplified production and concentration of lentiviral vectors to achieve high transduction in primary human T cells." BMC Biotechnology (2013); 13(1): 98.

Cullen and Greene, "Regulatory Pathways Governing HIV-1 Replication", Cell (1989); 58: 423-426.

Cullen, B.R., "Human Immunodeficiency Virus as a Prototypic Complex Retrovirus", Journal of Virology (1991); 65(3): 1053-1056.

De Felipe, Pablo, and Ryan, Martin D. "Targeting of proteins derived from self-processing polyproteins containing multiple signal sequences." Traffic (2004); 5.8: 616-626.

De Oliveira, S.N., et al. "Modification of Hematopoietic Stem/Progenitor Cells with CD19-Specific Chimeric Antigen Receptors as a Novel Approach for Cancer Immunotherapy." Human Gene Therapy (2013); 24(10): 824-839.

De-Gang, S., et al., "In Vivo Persistence, Tumor Localization, and Antitumor Activity of CAR-Engineered T Cells Is Enhanced by Costimulatory Signaling through CD137 (4-1BB)." Cancer Research (2011), 71(13): 4617-4627.

Desjarlais, John R., and Berg, Jeremy M. "Length-encoded multiplex binding site determination: application to zinc finger proteins." Proceedings of the National Academy of Sciences (1994); 91.23: 11099-11103.

Desjarlais, John R., and Berg, Jeremy M. "Use of a zinc-finger consensus sequence framework and specificity rules to design specific DNA binding proteins." Proceedings of the National Academy of Sciences (1993); 90.6: 2256-2260.

DeWitt, S. Hobbs, et al. "Diversomers": An approach to nonpeptide, nonoligomeric chemical diversity. Proceedings of the National Academy of Sciences USA (1993); 90.15: 6909-6913.

Donnelly, M. et al., "The 'cleavage' activities of foot-and-mouth disease virus 2A site-directed mutants and naturally occurring '2A-like' sequences." J Gen Virol. (2001); 82 (Pt 5): 1027-1041.

Dull et al., "A third-generation lentivirus vector with a conditional packaging system", Journal of Virology (1998); 72(11): 8463-8671.

European Application No. EP 15783117.3, Extended European Search Report dated Aug. 22, 2017, 8 pages.

European Application No. EP 15783862.4, Extended European Search Report dated Sep. 22, 2017, 7 pages.

European Application No. EP 15802488.5, Third Party Observation dated Oct. 17, 2017, 3 pages.

European Application No. EP 15782739.5, Extended European Search Report dated Nov. 9, 2017, 11 pages.

Ferry and Heard, "Liver-directed gene transfer vectors", Hum Gene Ther. (1998); 9(14): 1975-1981.

Gallop, Mark A., et al. "Applications of combinatorial technologies to drug discovery. 1. Background and peptide combinatorial libraries." Journal of Medicinal Chemistry (1994); 37.9: 1233-1251.

Garland, R. J., et al. "The use of Teflon cell culture bags to expand functionally active CD8+ cytotoxic T lymphocytes." Journal of Immunological Methods (1999); 227.1: 53-63.

Gattinoni, L., et al., "Adoptive immunotherapy for cancer: building on success." Nat Rev Immunol (2006); 6(5): 383-393, 25 pages.

GenBank Accession Reference # L09137.2, "Cloning vector pUC19c", Apr. 27, 1993, 3 pages.

Giannoni, F., et al., "Allelic Exclusion and Peripheral Reconstitution by TCR Transgenic T Cells Arising From Transduced Human Hematopoietic Stem/Progenitor Cells." Molecular Therapy (2013); 21(5): 1044-1054.

Guertin, David A., and Sabatini, David M. "Defining the role of mTOR in cancer." Cancer Cell (2007); 12.1: 9-22.

Haanen, John B.A.G., et al. "Selective expansion of cross-reactive CD8+ memory T cells by viral variants." Journal of Experimental Medicine (1999); 190.9: 1319-1328.

Holliger, Philipp, et al. "Diabodies": small bivalent and bispecific antibody fragments. Proceedings of the National Academy of Sciences (1993); 90.14: 6444-6448.

(56) References Cited

OTHER PUBLICATIONS

Holt, L. et al., "Domain antibodies: proteins for therapy", Trends in Biotechnology (2003); 21(11): 484-490.
Huang and Yen, "Role of the hepatitis B virus posttranscriptional regulatory element in export of intronless transcripts", Molecular and Cellular Biology (1995); 15(7): 3864-3869.
Hudson, Peter J., and Souriau, Christelle. "Engineered antibodies." Nature medicine 9.1 (2003): 129-134.
Imren, S. et al., "High-level beta-globin expression and preferred intragenic integration after lentiviral transduction of human cord blood stem cells", J Clin Invest (2004); 114(7): 953-962.
International Application No. PCT/US2015/041722, International Preliminary Report on Patentability dated Jan. 24, 2017, 7 pages.
International Preliminary Report on Patentability for International Application No. PCT/US2015/027510, dated Oct. 25, 2016, 6 pages.
International Preliminary Report on Patentability for International Application No. PCT/US2015/027518, dated Oct. 25, 2016, 6 pages.
International Preliminary Report on Patentability for International Application No. PCT/US2015/027539, dated Oct. 25, 2016, 6 pages.
International Preliminary Report on Patentability for International Application No. PCT/US2015/034515, dated Dec. 5, 2016, 10 pages.
International Preliminary Report on Patentability for International Application No. PCT/US2015/064269, dated Jun. 22, 2017, 6 pages.
International Search Report and Written Opinion for International Application No. PCT/US2015/027510, dated Jul. 30, 2015, 10 pages.
International Search Report and Written Opinion for International Application No. PCT/US2015/027518, dated Jul. 30, 2015, 9 pages.
International Search Report and Written Opinion for International Application No. PCT/US2015/027539, dated Nov. 2, 2015, 6 pages.
International Search Report and Written Opinion for International Application No. PCT/US2015/034515, dated Sep. 14, 2015, 12 pages.
International Search Report and Written Opinion for International Application No. PCT/US2015/041722, dated Jan. 6, 2016, 11 pages.
International Search Report and Written Opinion for International Application No. PCT/US2015/064269, dated Feb. 23, 2016, 9 pages.
International Search Report and Written Opinion for International Application No. PCT/US2015/064270, dated Feb. 11, 2016, 11 pages.
Irion, Stefan, et al. "Identification and targeting of the ROSA26 locus in human embryonic stem cells." Nature Biotechnology (2007); 25.12: 1477-1482.
Kalled, Susan L. "The role of BAFF in immune function and implications for autoimmunity." Immunological Reviews (2005); 204.1: 43-54.
Kay, M. A., "Adenoviral Vectors for Hepatic Gene Transfer in Animals." Chest (1997); 111: 138S-142S.
Kim, Yang-Gyun, et al. "Hybrid restriction enzymes: zinc finger fusions to Fok I cleavage domain." Proceedings of the National Academy of Sciences (1996); 93.3: 1156-1160.
Kochenderfer, J.N., et al. "Adoptive Transfer Of Syngeneic T Cells Transduced With A Chimeric Antigen Receptor That Recognizes Murine CD19 Can Eradicate Lymphoma And Normal B Cells." Blood (2010); 16(19): 3875-3886; Gen Bank Accession No. HM754222.1, 25 pages.
Koch-Nolte, F., "Single domain antibodies from llama effectively and specifically block T cell ecto-ADP-ribosyltransferase ART2.2 in vivo", Faseb J (2007); 21(13):3490-3498.
Koldej, R.M., et al., "Comparison of Insulators and Promoters for Expression of the Wiskott-Aldrich Syndrome Protein Using Lentiviral Vectors" Human Gene Therapy Clinical Development (2013); 24: 77-85.

Kozak, M., "An analysis of 5'-noncoding sequences from 699 vertebrate messenger RNAs", Nucleic Acids Res. (1987); 15(20): 8125-8148.
Kozak, M., "Point mutations define a sequence flanking the AUG initiator codon that modulates translation by eukaryotic ribosomes", Cell (1986); 44(2): 283-292.
Kutner et al., "Production, concentration and titration of pseudotyped HIV-1-based lentiviral vectors", Nature Protocols (2009); 4: 495-505.
Laabi, Y., et al. "A new gene, BCM, on chromosome 16 is fused to the interleukin 2 gene by at (4; 16)(q26; p13) translocation in a malignant T cell lymphoma." The EMBO Journal (1992); 11.11: 3897-3904.
Laabi, Yacine, et al. "The BCMA gene, preferentially expressed during B lymphoid maturation, is bidirectionally transcribed." Nucleic Acids Research (1994); 22.7: 1147-1154.
Landau and Littman. "Packaging system for rapid production of murine leukemia virus vectors with variable tropism." Journal of Virology (1992); 66.8: 5110-5113.
Larson, S.M., et al. "Anti-CD19 chimeric antigen receptor controlled by the suicide gene HSVsr39TK in hematopoietic stem cells for immunotherapy of B-lineage malignancies." Blood (2013); 122(21): 1659.
Lee, H. C. et al., "Remission in models of type 1 diabetes by gene therapy using a single-chain insulin analogue", Nature (2000); 408(6811): 483-488.
Levitt, "Definition of an efficient synthetic poly(A) site", Genes & Development (1989); 3: 1019-1025.
Liu, Lin, et al., "Adoptive T-cell therapy of B-cell malignancies: Conventional and physiological chimeric antigen receptors." Cancer Letters (2012); 316(1): 1-5.
Liu and Mertz, "HnRNP L binds a cis-acting RNA sequence element that enables intron-dependent gene expression." Genes & Dev. (1995); 9: 1766-1780.
Liu, Pixu, et al. "Targeting the phosphoinositide 3-kinase pathway in cancer." Nature Reviews Drug Discovery (2009); 8.8: 627-644.
Liu, Qiang, et al. "Design of polydactyl zinc-finger proteins for unique addressing within complex genomes." Proceedings of the National Academy of Sciences (1997);94.11: 5525-5530.
Lovelock and Bishop, "Prevention of freezing damage to living cells by dimethyl sulphoxide", Nature (1959); 183(4672): 1394-1395.
Mackay, Fabienne, et al. "BAFF and APRIL: a tutorial on B cell survival." Annual Review of Immunology (2003); 21.1: 231-264.
Maier, Dawn, et al., "Development of a Simple and Robust Closed System Manufacturing Platform for T Cells Engineered With Chimeric Antigen Receptor (CAR) for Adoptive Immunotherapy." Molecular Therapy (2014); Supplement 1(22): S284.
Maldarelli et al., "Identification of posttranscriptionally active inhibitory sequences in human immunodeficiency virus type 1 RNA: novel level of gene regulation", Journal of Virology (1991); 65(11): 5732-5743.
Malim et al., "Immunodeficiency virus rev trans-activator modulates the expression of the viral regulatory genes", Nature (1988); 335: 181-183.
Meuer, Stefan C., et al. "An alternative pathway of T-cell activation: a functional role for the 50 kd T11 sheep erythrocyte receptor protein." Cell (1984); 36.4: 897-906.
Miller, A.D., "Human gene therapy comes of age." Nature (1992); 357: 455-460.
Milone, M. et al., "Chimeric receptors containing CD137 signal transduction domains mediate enhanced survival of T cells and increased antileukemic efficacy in vivo", Molecular Therapy (2009); 17(8):1453-1464.
Moreaux, Jérôme, et al. "BAFF and APRIL protect myeloma cells from apoptosis induced by interleukin 6 deprivation and dexamethasone." Blood (2004); 103.8: 3148-3157.
Naldini L. et al., "Efficient transfer, integration, and sustained long-term expression of the transgene in adult rat brains injected with a lentiviral vector", Proc Natl Acad Sci USA (1996); 93(21): 11382-11388.

(56) References Cited

OTHER PUBLICATIONS

Naldini, L. et al., "In vivo gene delivery and stable transduction of nondividing cells by a lentiviral vector", Science (1996); 272(5259): 263-267.
Naldini, L., "Lentiviruses as gene transfer agents for delivery to non-dividing cells", Curr Opin Biotechnol. (1998); 5: 457-63.
Neri, Paola, et al. "Neutralizing B-Cell-Activating Factor Antibody Improves Survival and Inhibits Osteoclastogenesis in a Severe Combined Immunodeficient Human Multiple Myeloma Model." Clinical Cancer Research (2007); 13.19: 5903-5909.
Ng et al., "B Cell-Activating Factor Belonging to the TNF Family (BAFF)-R Is the Principal BAFF Receptor Facilitating BAFF Costimulation of Circulating T and B Cells." Journal of Immunology (2004); 173(2): 807-817.
Novak, Anne J., et al. "Expression of BCMA, TACI, and BAFF-R in multiple myeloma: a mechanism for growth and survival." Blood (2004); 103.2: 689-694.
O'Connor, Brian P., et al. "BCMA is essential for the survival of long-lived bone marrow plasma cells." Journal of Experimental Medicine (2004); 199.1: 91-98.
Oka, K. et al., "Recent advances in liver-directed gene therapy: implications for the treatment of dyslipidemia", Curr Opin Lipidol. (2000); 11(2): 179-186.
Orlandi, R. et al., "Cloning immunoglobulin variable domains for expression by the polymerase chain reaction", Proc Natl Acad Sci USA (1989); 86(10):3833-3737.
Patel, S. et al., "Impact of chimeric immune receptor extracellular protein domains on T cell function." Gene Ther (1999); 6(3): 412-419.
Plückthun, A. "Antibodies from *Escherichia coli*." The Pharmacology of Monoclonal Antibodies. (eds. Rosenburg and Moore), Springer Berlin Heidelberg (1994); 113: 269-315.
Pomerantz, Joel L., et al. "Structure-based design of transcription factors." Science (1995); 267.5194: 93-96.
Riechmann and Muyldermans, "Single domain antibodies: comparison of camel VH and camelised human VH domains", J Immunol Methods (1999); 231(1-2):25-38.
Ruella, M. and Kalos, M. "Adoptive immunotherapy for cancer." Immunological Reviews (2014); 257(1): 14-38.
Ryan, M. et al., "Virus-encoded proteinases of the picornavirus super-group." J Gen Virol. (1997); 78 (Pt 4): 699-723.
Sanchez, Eric, et al. "Serum B-cell maturation antigen is elevated in multiple myeloma and correlates with disease status and survival." British Journal of Haematology (2012); 158.6: 727-738.
Schiemann, Barbara, et al. "An essential role for BAFF in the normal development of B cells through a BCMA-independent pathway." Science (2001); 293.5537: 2111-2114.
Sather, B.B., et al. "Development of B-lineage Predominant Lentiviral Vectors for Use in Genetic Therapies for B Cell Disorders." Molecular Therapy (2011); 19(3): 515-525.
Shiratori, Y. et al., "Strategy of liver-directed gene therapy: present status and future prospects", Liver (1999); 19(4): 265-274.
Singh et al., "HER2-positive advanced breast cancer: optimizing patient outcomes and opportunities for drug development", British Journal of Cancer (2014); 111: 1888-1898.
Smith-Arica and Bartlett, "Gene Therapy: Recombinant Adeno-associated Virus Vectors", Curr. Cardiol. Rep. (2001); 3: 43-49.
Somerville and Dudley, "Bioreactors get personal." OncoImmunology (2012); 1(9): 1-3.
Soneoka, Yuko, et al. "A transient three-plasmid expression system for the production of high titer retroviral vectors." Nucleic Acids Research (1995); 23.4: 628-633.
Strayer, D.S., "Viral gene delivery", Expert Opinion on Investigational Drugs (1999); 8(12): 2159-2172.
Szymczak, Andrea L., et al. "Correction of multi-gene deficiency in vivo using a single'self-cleaving'2A peptide-based retroviral vector." Nature Biotechnology (2004); 22.5: 589-594.
Ten Berge, I. J. M., et al. "Selective expansion of a peripheral blood CD8+ memory T cell subset expressing both granzyme B and I-selectin during primary viral infection in renal allograft recipients." Transplantation Proceedings (1998); 30(8): 3975-3977.
Thompson, Jeffrey S., et al. "BAFF binds to the tumor necrosis factor receptor-like molecule B cell maturation antigen and is important for maintaining the peripheral B cell population." Journal of Experimental Medicine (2000); 192.1: 129-136.
Thulé and Liu, "Regulated hepatic insulin gene therapy of STZ-diabetic rats", Gene Therapy (2000); 7: 1744-1752.
Tumaini, B., et al., "Simplified process for the production of anti-CD19-CAR-engineered T cells." Cytotherapy (2013); 15: 1406-1415.
Van Der Waart, A.B., et al., "Akt Signalling Inhibition Promotes The Ex Vivo generation Of Minor Histocompatibility Antigen-Specific CD8+ Memory Stem T Cells." Blood (2013); 122(21): 3269. (Abstract, 2 pages).
Vera, Juan, et al. "T lymphocytes redirected against the K light chain of human immunoglobulin efficiently kill mature B lymphocyte-derived malignant cells." Blood (2006); 108.12: 3890-3897.
Wu and Kabat, "An analysis of the sequences of the variable regions of Bence Jones proteins and myeloma light chains and their implications for antibody complementarity", J Exp Med. (1970); 132(2): 211-250.
Xu, Shengli, and Lam, Kong-Peng. "B-cell maturation protein, which binds the tumor necrosis factor family members BAFF and APRIL, is dispensable for humoral immune responses." Molecular and Cellular Biology (2001); 21.12: 4067-4074.
Yang, N.S., "Gene Transfer into Mammalian Somatic Cells in Vivo", Critical Reviews in Biotechnology (1992); 12(4): 335-356.
Yang, Soo Young, et al. "A common pathway for T lymphocyte activation involving both the CD3-Ti complex and CD2 sheep erythrocyte receptor determinants." The Journal of Immunology (1986); 137.4: 1097-1100.
Yee, Jiing-Kuan, et al. "A general method for the generation of high-titer, pantropic retroviral vectors: highly efficient infection of primary hepatocytes." Proceedings of the National Academy of Sciences USA. (1994); 91.20: 9564-9568.
Zennou, V. et al., "HIV-1 genome nuclear import is mediated by a central DNA flap." Cell (2000); 101(2): 173-185.
Zhong, Shi, et al. "Retroviral transduction of T-cell receptors in mouse T-cells." JoVE (Journal of Visualized Experiments) (2010); 44: e2307, 4 pages.
Zuckermann, Ronald N., et al. "Discovery of nanomolar ligands for 7-transmembrane G-protein-coupled receptors from a diverse N-(substituted) glycine peptoid library." Journal of Medicinal Chemistry (1994); 37.17: 2678-2685.
Zufferey et al., "Multiply attenuated lentiviral vector achieves efficient gene delivery in vivo", Nat Biotechnol. (1997), 15(9): 871-875.
Zufferey, R. et al., "Woodchuck hepatitis virus posttranscriptional regulatory element enhances expression of transgenes delivered by retroviral vectors." J Virol. (1999); 73(4): 2886-2892.
Zufferey, R. et al., "Self-Inactivating Lentivirus Vector for Safe and Efficient In Vivo Gene Delivery", J Virol (1998); 72(12): 9873-9880.
Esser, et al., "NK cells engineered to express a GD2-specific antigen receptor display built-in ADCC-like activity against tumor cells of neuroectodermal origin." Journal of Cellular and Molecular Medicine (2012); 16(3): 569-581.
European Application No. EP 15802488.5, Extended European Search Report dated Dec. 19, 2017, 11 pages.
European Application No. EP 15824299.0, Extended European Search Report dated Dec. 13, 2017, 11 pages.
Garfall, A.L., "Immunotherapy with Chimeric Antigen Receptors for Multiple Myeloma." Discovery Medicine: Discovery Class of Medicine, Research Technology, and T. Solariz, Inc., (2014); 17(91): 37-46.
Hirai, et al., "MK-2206, an Allosteric Aid Inhibitor, Enhances Antitumor Efficacy by Standard Chemotherapeutic Agents or Molecular Targeted Drugs In vitro and In vivo." Molecular Cancer Therapeutics (2010); 9(7): 1956-1967.
Kim, et al., "Role of PI3K/Akt signaling in memory CD8 T cell differentiation." Frontiers in Immunology (2013); 4: 20, 11 pages.

(56) References Cited

OTHER PUBLICATIONS

Lanitis, et al., "Chimeric Antigen Receptor T Cells with Dissociated Signaling Domains Exhibit Focused Antitumor Activity with Reduced Potential for Toxicity In Vivo." Cancer Immunology Research (2013); 1(1): 43-53, published on line Apr. 7, 2013.
Li, Qun, "Recent progress in the discovery of Akt inhibitors as anticancer agents." Expert Opinion on Therapeutic Patents (2007); 17(9): 1077-1130.
Movassagh, et al., "Retrovirus-Mediated Gene Transfer into T cells: 95% transduction efficiency without Further in Vitro Selection." Human Gene Therapy (2000); 11: 1189-1200.
Perkins, et al., "Manufacturing an Enhanced CAR T Cell Product By Inhibition of the PI3K/Akt Pathway During T Cell Expansion Results in Improved In Vivo Efficacy of Anti-BCMA CAR T Cells." Blood (2015); 126(3): 1893.
Third Party Submission filed in U.S. Appl. No. 15/316,792, filed Feb. 23, 2018, 6 pages.
Urak, et al., "Ex vivo Akt inhibition promotes the generation of potent CD19CAR T cells for adoptive immunotherapy." Journal for Immuno Therapy of Cancer (2017); 5(1): 26, 13 pages.
Van Der Waart, A.B., et al., "Akt Signalling Inhibition Promotes The Ex Vivo generation Of Minor Histocompatibility Antigen-Specific CD8+ Memory Stem T Cells." Blood (2013); 122(21): 3269.
Van Der Waart, A.B., et al., "Inhibition of Akt signaling promotes the generation of superior tumor-reactive T cells for adoptive immunotherapy." Blood (2014); 124(23): 3490-3500.
Van Der Waart, A.B., et al., "Time to Akt Superior tumor-reactive T cells for adoptive immunotherapy." OncoImmunology (2015); 4(5): e1003016, 3 pages.
Weigelt, et al., "Genomic determinants of the PI3K pathway inhibitor response in cancer." Frontiers in Oncology (2012), 2: Article V 109, pp. 1-16.
Wu, et al., "Over-expressing Akt in T cells to resist tumor immunosuppression and increase anti-tumor activity." BMC Cancer (2015); 15(1): 603, 10 pages.
Yap, et al., "Preclinical Pharmacology, Antitumor Activity, and Development of Pharmacodynamic Markers for the Novel, Potent AKT Inhibitor CCT128930." Molecular Cancer Therapeutics (2011); 10(2): 360-371, (Published on-line First Dec. 29, 2010).
Zhang, et al., "An NKp30-Based Chimeric Antigen Receptor Promotes T cell Effector Functions and Antitumor Efficacy In Vivo." The Journal of Immunology (2012); 189: 2290-2299 (prepublished online Jul. 30, 2012).
European Application No. EP 15868392.0, Extended European Search Report dated Jun. 25, 2018, 5 pages.
Halene, et al., "Improved Expression in Hematopoietic and Lymphoid Cells in Mice After Transplantation of Bone Marrow Transduced With a Modified Retroviral Vector." Blood (1999); 94(10): 3349-3357.
International Preliminary Report on Patentability for International Application No. PCT/US2015/064270, dated Jun. 12, 2018, 12 pages.
Li, et al., "Optimal promoter usage for lentiviral vector-mediated transduction of cultured central nervous system cells." Journal of Neuroscience Methods (2010); 189 (1): 56-64.
Kochenderfer, J.N., et al., "Construction and Pre-clinical Evaluation of an Anti-CD19 Chimeric Antigen Receptor." J Immunother. (2009); 32 (7): 689-702.
Shirasu and Kuroki, "Functional Design of Chimeric T-Cell Antigen Receptors for Adoptive Immunotherapy of Cancer: Architecture and Outcomes." Anticancer Research (2012); 32 (6): 2377-2383.
Uchibori, et al., "CD269 (BCMA)-Specific CAR-Expressing T Cells Dramatically Eradicate Myeloma Cells from Bone Marrow of an Orthotopic Multiple Myeloma Mouse Model." Molecular Therapy (2016); Abstract 400, 24 (Supplement 1): p. S158-S159.
Wang, et al., "CS-1 Re-Directed Central Memory T Cell Therapy for Multiple Myeloma." Blood (2014); 124 (21): 1114.
Ward, et al., "Binding activities of a repertoire of single immunoglobulin variable domains secreted from *Escherichia coli*." Nature (1989); 341 (6242): 544-546.
Friedman et al., "Effective Targeting of Multiple B-Cell Maturation Antigen-Expressing Hematological Malignances by Anti-B-Cell Maturation Antigen Chimeric Antigen Receptor T Cells," Human Gene Therapy, vol. 29, No. 5, 585-601, 2018.
Huye L.E. et al. "Combining mTor inhibitors with rapamycin-resistant T cells: a two-pronged approach to tumor elimination". Molecular Therapy, 2011, 19(12): 2239-2248.
Kulemzin et al., "Engineering Chimeric Antigen Receptors," Acta Naturae, vol. 9, No. 1 (32) 2017, 6-14.
Muyldermans, et al., "Nanobodies: Natural Single-Domain Antibodies," Annual Review of Biochemistry vol. 82:775-797 (vol. publication date Jun. 2013) First published online as a Review in Advance on Mar. 13, 2013 https://doi.org/10.1146/annurev-biochem-063011-092449.
Xu et al., "The development of CAR design for tumor CAR-T cell therapy," Oncotarget, 2018, vol. 9, No. 17, pp. 13991-14004.
Xue L. et al., "The role of the PI3K-AKT kinase pathway in T-cell development beyond the beta checkpoint". Eur J Immunol., 2008, 38(11):3200-7.
Allan et al., "Generation of Potent and Stable Human CD4+ T Regulatory Cells by Activation-independent Expression of FOXP3," www.moleculartherapy.org vol. 16 No. 1, 194-202 Jan. 2008.
European Application No. EP 19193858.8, Extended European Search Report dated Feb. 21, 2020, 10 pages.
European Application No. EP 19210785.2, Extended European Search Report dated Feb. 21, 2020, 9 pages.
European Application No. EP 19218258.2, Extended European Search Report dated Jun. 26, 2020, 7 pages.
Fedorov VD et al., "PD-1- and CTLA-4-Based Inhibitory Chimeric Antigen Receptors (iCARs) Divert Off-Target Immunotherapy Responses", Sci Transl Med, 2013, vol. 5, No. 215, pp. 1-25.
Mallone et al., "Isolation and preservation of peripheral blood mononuclear cells for analysis of islet antigen-reactive T cell responses: position statement of the T-Cell Workshop Committee of the Immunology of Diabetes Society," Clin Exp Immunol. Jan. 2011;163(1):33-49.
Sadelain M et al., "The basic principles of chimeric antigen receptor (CAR) design", Cancer Discov, 2013, vol. 3, No. 4, pp. 388-398.
Xu et al., "Closely related T-memory stem cells correlate with in vivo expansion of CAR.CD19-T cells and are preserved by IL-7 and IL-15," Blood, Jun. 12, 2014, vol. 123, No. 24.
Zhong, X. et al., "Chimeric antigen receptors combining 4-1BB and CD28 signaling domains augment PI3kinase/AKT/Bcl-XL activation and CD8+T cell-mediated tumor eradication", Mol Ther (2010);18(2):413-20.
Astrakhan et al., "Ubiquitous high-level gene expression in hematopoietic lineages provides effective lentiviral gene therapy of murine Wiskott-Aldrich syndrome," Blood. May 10, 2012; 119(19): 4395-4407.
Aviles Mendoza et al., "Comparison of Five Retrovirus Vectors Containing the Human IL-2 Receptor g Chain Gene for Their Ability to Restore T and B Lymphocytes in the X-Linked Severe Combined Immunodeficiency Mouse Model," Molecular Therapy vol. 3, No. 4, Apr. 2001, 9 pages.
Dienstmann et al., "Picking the Point of Inhibition: A Comparative Review of PI3K/AKT/mTOR Pathway Inhibitors," Molecular Cancer Therapeutics, 13(5):1021-1031, Apr. 18, 2014.
European Application No. EP 15782739.5, Notice of Opposition dated Oct. 2, 2020, 9 pages.
European Application No. EP 20205511.7, Extended European Search Report dated May 6, 2021, 13 pages.
European Application No. EP 20170239.6, Extended European Search Report dated Sep. 18, 2020, 11 pages.
Gattinoni, L., et al., "Moving T memory stem cells to the clinic," Blood, Jan. 24, 2013, vol. 121, No. 4, pp. 567-568.
Han et al., "Chimeric antigen receptor-engineered T cells for cancer immunotherapy: progress and challenges," Journal of Hematology & Oncology, Jul. 8, 2013, 6:47, 7 pages.
Oh et al., "Lentiviral vector design using alternative RNA export elements," Retrovirology, 2007, 4:38, 10 pages.
Ryan et al., Antibody targeting of B-cell maturation antigen on malignant plasma cells, Mol Cancer Ther, Nov. 2007, vol. 6, No. 11, pp. 3009-3018.

(56) References Cited

OTHER PUBLICATIONS

Sigma-Aldrich, "Cryopreservation", Biofiles, vol. 5, No. 4, pp. 1-22, published 2010.
Adler and Dimitrov, Therapeutic Antibodies Against Cancer, 26 Hematology/Oncology Clinics of North America 447-481 (2012) ("Adler").
Ahmad et al., "scFv Antibody: Principles and Clinical Application," Clinical and Developmental Immunology, vol. 2012, Article ID 980250, 15 pages.
Almagro et al., "Humanization of antibodies," Frontiers in Bioscience, 13, Jan. 1, 2008, pp. 1619-1633.
Atanackovic, D., et al., "CD4+CD25+FOXP3+ T Regulatory Cells Reconstitute and Accumulate In The Bone Marrow of Patients With Multiple Myeloma Following Allogeneic Stem Cell Transplantation," Haematol 93(3):423-430 (2008).
Barthelemy et al., "Comprehensive Analysis of the Factors Contributing to the Stability and Solubility of Autonomous Human VH Domains," The Journal of Biological Chemistry, Feb. 8, 2008, vol. 283, No. 6, pp. 3639-3654.
Bausch-Fluck, et al., "A Mass Spectrometric-Derived Cell Surface Protein Atlas," PLoS One 10(4):e0121314, pp. 1-22 (2015).
Bausch-Fluck, et al., "The In Silico Human Surfaceome," PNAS 115(46): E10988-E10997 (2018).
Beck, A., et al., "Strategies and Challenges for the Next Generation of Therapeutic Antibodies," Immunol 10:345-352 (2010).
Beiboer et al., "Guided Selection of a Pan Carcinoma Specific Antibody Reveals Similar Binding Characteristics yet Structural Divergence Between the Original Murine Antibody and its Human Equivalent," J. Mol. Biol. (2000) 296, pp. 833-849.
Berger et al., "CD28 costimulation and immunoaffinity-based selection efficiently generat primary gene-modified T cells for adoptive immunotherapy," Blood, Jan. 15, 2003, vol. 101, No. 2, pp. 476-484.
Biagi et al., "Chimeric T-cell receptors: new challenges for targeted immunotherapy in hematologic malignancies," Haematologica 2007; 92:381-388.
Bleumer, I., et al., "A Phase II Trial of Chimeric Monoclonal Antibody G250 for Advanced Renal Cell Carcinoma Patients," Br J Cancer 90:985-990 (2004).
Bobisse et al., "Reprogramming T Lymphocytes for Melanoma Adoptive Immunotherapy by T-Cell Receptor Gene Transfer with Lentiviral Vectors," Cancer Research, Dec. 15, 2009; 69(24), pp. 9385-9394.
Braendstrup, P., et al., "The Long Road to The First FDA Approved Gene Therapy: Chimeric Antigen Receptor T Cells Targeting CD19," Cytotherapy 22(2):57-69 (2020).
Braga, W.M.T., et al., "The Role of Regulatory T Cells and TH17 Cells in Multiple Myeloma," Clin Dev Immunol 2012(293479):1-4, (2012).
Brenner, M. K. and Heslop, H.E., "Adoptive T Cell Therapy of Cancer," Curr Opin Immunol 22:251-257 (2010).
Brentjens, R.J., et al., "Genetically Targeted T Cells Eradicate Systemic Acute Lymphoblastic Leukemia Xenografts," Clin Cancer Res 13(18):5426-5435 (2007).
Brentjens, R., et al., "Treatment of Chronic Lymphocytic Leukemia With Genetically Targeted Autologous T Cells: Case Report of an unforeseen Adverse Event in a Phase I Clinical Trial," Molecular Therapy 18(4):666-668 (2010).
Brimnes, M.K. et al., "Increased Level of Both CD4+FOXP3+ Regulatory T Cells and CH14+HLA-DR-/low Myeloid-Derived Suppressor Cells and Decreased Level of Dendritic Cells in Patients with Multiple Myeloma," Clin Immunol 72:540-547 (2010).
Bross et al., "Approval Summary: Gemtuzumab Ozogamicin in Relapsed Acute Myeloid Leukemia," Clinical Cancer Research, Jun. 2001, vol. 7, 1490-1496.
Caers et al., "Multiple myeloma—an update on diagnosis and treatment," European Journal of Haematology, 2008 81 (329-343).
Cartellieri, M., et al., "Chimeric Antigen Receptor-Engineered T Cells for Immunotherapy of Cancer," J Biomed and Biotech 2010(956304):1-13 (2010).
Ch'en et al., "Characterisation of monoclonal antibodies to the TNF and TNF receptor families," Cellular Immunology 236 (2005) 78-85.
Chauhan, A.K., "Human CD4+ T-Cells: A Role for Low-Affinity Fc Receptors," Front. Immunol. (2016) 7:215, 8 pages.
Chinnasamy et al., "Gene therapy using genetically modified lymphocytes targeting VEGFR-2 inhibits the growth of vascularized syngenic tumors in mice," J Clin Invest. 2010;120(11):3953-3968.
Cho et al., "Targeting B Cell Maturation Antigen (BCMA) in Multiple Myeloma: Potential Uses of BCMA-Based Immunotherapy," Front. Immunol. (2018) 9:1821.
Choi et al., "Predicting antibody complementarity determining region structures without classification," Molecular BioSystems, 2011, 7, pp. 3327-3334.
Clarke et al., "Improved Post-Thaw Recovery of Peripheral Blood Stem/Progenitor Cells Using a Novel Intracellular-like Cryopreservation Solution," Cytotherapy, 2009, 11(4): 472-479.
Extract from ThermoFisher Website page, Dynabeads cell isolation and expansion support—getting started, 1 page.
Dai et al., "Human Immunodeficiency Virus Integrates Directly into Naïve Resting CD4+ T Cells but Enters Naïve Cells Less Efficiently than Memory Cells," Journal of Virology, May 2009, pp. 4528-4537.
De Claro, "U.S. Food and Drug Administration Approval Summary: Brentuximab Vedotin for the Treatment of Relapsed Hodgkin Lymphoma or Relapsed Systemic Anaplastic Large-Cell Lymphoma," Clin Cancer Res; 2012; 18(21); 5845-9.
De Genst et al., "Antibody repertoire development in camelids," Developmental and Comparative Immunology, 30 (2006), pp. 187-198.
Demko et al., "FDA Drug Approval Summary: Alemtuzumab as Single-Agent Treatment for B-Cell Chronic Lymphocytic Leukemia," The Oncologist 2008;13:167-174.
Di Bernardo, A., et al., "Humoral Immunotherapy of Multiple Myeloma: Perspectives and Perplexities," Expert Opin. Biol. Ther. 10(6):863-873 (2010).
Di Ianni et al., "Immunomagnetic isoloation of CD4+CD25+ FoxP3+ natural T regulatory lymphocytes for clinical applications," Jan. 9, 2009, British Society for Immunology, Clinical and Experimental Immunology, 156: pp. 246-253.
Di Stassi et al., "T lymphocytes coexpressing CCR4 and a chimeric antigen receptor targeting CD30 have improved homing and anti-tumor activity in a Hodgkin tumor model," Blood, Jun. 18, 2009, vol. 113, No. 25, 6392-6402.
Dimopoulos and Terpos, "Multiple myeloma," Annals of Oncology 21 (Supplement 7): vii143-vii150, 2010.
Dimopoulos et al., "Current treatment landscape for relapsed and/or refractory multiple myeloma," Nat. Rev. Clin. Oncol. 12, 42-54 (2015) published online Nov. 25, 2014.
Edwards et al., "The Remarkable Flexibility of the Human Antibody Repertoire; Isolation of Over One Thousand Different Antibodies to a Single Protein, BLyS," J. Mol. Biol. (2003) 334, pp. 103-118.
Eshhar et al., "Specific activation and targeting of cytotoxic lymphocytes through chimeric single chains consisting of antibody-binding domains and the γ or ζ subunits of the immunoglobulin and T-cell receptors," PNAS USA, Jan. 1993, vol. 90, pp. 720-724.
European Application No. EP 15783117.3, Notice of Opposition dated Jan. 19, 2021, 37 pages.
European Application No. EP 15783117.3, Notice of Opposition dated Jan. 21, 2021, 28 pages.
European Application No. EP 15783117.3, Notice of Opposition dated Jan. 22, 2021, 41 pages.
Extract from Signal Peptide Database, Jun. 10, 2010, 3 pages.
Feyler, S., et al., "CD4+CD35+FoxP3+ Regulatory T Cells are Increase Whilst CD3+CD4-CD8-αβTCR+ Double Negative T Cells are Decreased the Peripheral Blood of Patients with Multiple Myeloma Which Correlates With Disease Burden," Br J Haematol 144:686-695 (2009).
Ficoll-Paque manual, GE Healthcare Life Sciences, Isolation of mononuclear cells, Methodology and applications, Aug. 2014, 20 pages.
Finney et al., "Activation of resting human primary T cells with chimeric receptors: costimulationfrom CD28, inducible costimula-

(56) References Cited

OTHER PUBLICATIONS tor, CD134, and CD137 in series with signals from the TCRζ chain," J Immunol 2004; 172:104-113.
Finney et al., "Chimeric receptors providing both primary and costimulatory signaling in T cells from a single gene product," J Immunol 1998; 161:2791-2797.
Geffen and Man, "New Drugs for the Treatment of Cancer, 1990-2001," IMAJ 2002;4:1124-1131.
Gentile, M., et al., "Emerging Biological Insights and Novel Treatment Strategies in Multiple Myeloma," Expert Opin Emerg Drugs 17(3):407-438 (2012).
Giannopoulos, K., et al., "The Frequency of T Regulatory Cells Modulates the Survival of Multiple Myeloma Patients: Detailed Characterisation of Immune Status in Multiple Myeloma," Br J Cancer 106:546-552 (2012).
Griffiths et al., "Human anti-self antibodies with high specificity from phage display libraries," The EMBO Journal, vol. 12, No. 2, 1993, pp. 725-734.
Gross et al., "Expression of immunoglobulin-T-cell receptor chimeric molecules as functional receptors with antibody-type specificity," PNAS USA, Dec. 1989, vol. 86, pp. 10024-10028.
Guidance for Industry, Estimating the Maximum Safe Starting Dose in Initial Clinical Trials for Therapeutics in Adult Healthy Volunteers, U.S. Department of Health and Human Services Food and Drug Administration, Center for Drug Evaluation and Research (CDER), Jul. 2005, 32 pages.
Guest et al., "Definition and application of good manufacturing process-compliant production of CEA-specific chimeric antigen receptor expressing T-cells for phase I/II clinical trial," Cancer Immunol Immunother (2014) 63: 133-145, Nov. 5, 2013; Supplementary Materials published with Guest et al. (2014) Cancer Immunol. Immunother. 63: 133-145.
Gupta et al., "Flow Cytometric Immunophenotyping and Minimal Residual Disease Analysis in Multiple Myeloma," Am J Clin Pathol 2009;132:728-732.
Hajela, K., "Structure and Function of Fc Receptors," Biochemical Education 19(2):50-57 (1991).
Hammer, O., "CD19 as an attractive target for antibody-based therapy," mAbs; Sep./Oct. 2012, 4:5, 571-577.
Han et al., "Polyfunctional responses by human T cells result from sequential release of cytokines," PNAS, Jan. 31, 2012, vol. 109, No. 5, pp. 1607-1612.
Haynes et al., "Single-chain antigen recognition receptors that costimulate potent rejection of established experimental tumors," Blood, 2002; 100(9): 3155-3163.
Hillerdal et al., "Systemic treatment with CAR-engineered T cells against PSCA delays subcutaneous tumor growth and prolongs survival of mice," BMC Cancer, Jan. 8, 2014, 14:30, 9 pages.
Hombach et al., "An Anti-CD30 Chimeric Receptor That Mediates CD3-ζ-independent T-Cell Activation against Hodgkin's Lymphoma Cells in the Presence of Soluble CD301," Cancer Research, Mar. 15, 1998, 58, 1116-1119.
Huang et al., "Recent advances in CAR-T cell engineering," Journal of Hematology & Oncology (2020) 13:86, 19 pages.
Huston et al., "Protein engineering of antibody binding sites: recovery of specific activity in an anti-digoxin single-chain Fv analogue produced in *Escherichia coli*," PNAS USA, Aug. 1988, vol. 85, pp. 5879-5883.
Iliopoulou et al., "Increased Frequency of CD4+ Cells Expressing CD161 in Cancer Patients," Clinical Cancer Research, Dec. 1, 2006, 12(23), pp. 6901-6909.
Imai et al., "Chimeric receptors with 4-1BB signaling capacity provoke potent cytotoxicity against acute lymphoblastic leukemia," Leukemia (2004) 18, 676-684.
Imai, C., et al., "Genetic Modification of Primary Natural Killer Cells Overcomes Inhibitory Signals and Induces Specific Killing of Leukemic Cells," Blood 106(1):376-383 (2005).
James and Kipp, "Rituximab in Chronic Lymphocytic Leukemia," Adv Ther (2011) 28(7):534-554.

Jena et al., "Redirecting T-cell specificity by introducing a tumor-specific chimeric antigen receptor," Blood, 2010; 116(7):1035-1044.
Jensen et al., "Antitransgene Rejection Responses Contribute to Attenuated Persistence of Adoptively Transferred CD20/CD19-Specific Chimeric Antigen Receptor Redirected T Cells in Humans," Biol Blood Marrow Transplant 16: 1245-1256 (2010).
Kalos et al., "T Cells with Chimeric Antigen Receptors Have Potent Antitumor Effects and Can Establish Memory in Patients with Advanced Leukemia," Science Translational Medicine, Aug. 2011, vol. 3., Issue 95, 95ra73, 13 pages.
Klimka et al., "Human anti-CD30 recombinant antibodies by guided phage antibody selection using cell panning," British Journal of Cancer (2000) 83(2), pp. 252-260.
Kochenderfer, J.N., et al., "A Phase I Clinical Trial of Treatment of B-Cell Malignancies with Autologous Anti-CD19-CAR-Transduced T Cells," Blood (2010) 116 (21): 2865.
Kochenderfer, J.N., et al., "B-cell depletion and remissions of malignancy along with cytokine-associated toxicity in a clinical trial of anti-CD19 chimeric-antigen-receptor-transduced T cells," Blood, 2012; 119(12): 2709-2720.
Kochenderfer, J.N., et al., "Chimeric Antigen Receptor-Modified T Cells in CLL," N Engl J Med 365;20: 1937-1939 (published: 2011).
Kochenderfer, J.N., et al., "Eradication of B-lineage cells and regression of lymphoma in a patient treated with autologous T cells genetically engineered to recognize CD19," Blood, 2010;116(20): 4099-4102.
Kumar et al., "Improved survival in multiple myeloma and the impact of novel therapies," Blood, 2008;111: 2516-2520.
Lamers, C.H.J., et al., "Treatment of Metastatic Renal Cell Carcinoma With Autologous T-Lymphocytes Genetically Retargeted Against Carbonic Anhydrase IX: First Clinical Experience," J Clin Oncol 24(13): e20-e22 (2006).
Lantis et al., "Redirected Antitumor Activity of Primary Human Lymphocytes Transduced With a Fully Human Anti-mesothelin Chimeric Receptor," Molecular Therapy, Mar. 2012, vol. 20, No. 3, 633-643.
Laubach et al., "Daratumumab granted breakthrough drug status," Expert Opin. Investig. Drugs (2014) 23(4): 445-452.
Lee et al., "The Genomic Organization of the CD28 Gene," The Journal of Immunology, vol. 145, No. 1, Jul. 1, 1990, pp. 344-352.
Lin et al., "Flow Cytometric Immunophenotypic Analysis of 306 Cases of Multiple Myeloma," Am J Clin Pathol 2004;121:482-488.
Lo et al., "Anti-GD3 Chimeric sFv-CD28/T-Cell Receptor ζ Designer T Cells for Treatment of Metastatic Melanoma and Other Neuroectodermal Tumors," Clin Cancer Res; 16(10); May 11, 2010, pp. 2769-2780.
Lloyd et al., "Modelling the human immune response: performance of a 1 0 human antibody repertoire against a broad panel of therapeutically relevant antigens," Protein Engineering, Design & Selection, vol. 22, No. 3, 2009, pp. 159-168.
Mahindra, A., et al., "Latest Advances And Current Challenges In The Treatment of Multiple Myeloma," Nat. Rev. Clin. Oncol. 9:135-143 (2012).
Mei et al., "Blood-borne human plasma cells in steady state are derived from mucosal immune responses," Blood, Mar. 12, 2009, vol. 113, No. 11, pp. 2461-2469.
Supplementary Materials published with Milone et al. (2009) Mol. Ther. 17(8): 1453-1464.
Mitsiades, C.S., et al., "Future Directions of Next-Generation Novel Therapies, Combination Approaches, and the Development of Personalized Medicine in Myeloma," J Clin Oncol 29(14):1916-1923 (2011).
Morgan, G., "Future Drug Developments in Multiple Myeloma: An Overview of Novel Lenalidomide-Based Combination Therapies," Blood Reviews 24(1):S27-S32 (2010).
Morgan, R., et al., "Case report of a Serious Adverse Event Following the Administration of T Cells Transduced With a Chimeric Antigen Receptor Recognizing ERBB2," Mol Therapy 18(4):843-851 (2010).
Nakazawa Y., "Gene-Modified T-cell Therapy Using Chimeric Antigen Receptor," Shinshu Medical Journal, 2013, vol. 61(4), pp. 197-203.

(56) References Cited

OTHER PUBLICATIONS

Nicholson et al., "Construction and characterisation of a functional CD19 specific single chain Fv fragment for immunotherapy of B lineage leukaemia and lymphoma," Molecular Immunology, 1997, vol. 34, No. 16-17, pp. 1157-1165.
Palumbo and Anderson, "Multiple Myeloma," The New England Journal of Medicine, 2011;364:1046-60.
Park, J.H. and Brentjens, R.J., "Adoptive Immunotherapy for Bcell Malignancies With Autologous Chimeric Antigen Receptor Modified Tumor Targeted T Cells," Discov Med. 9(47):277-288 (2010).
Payandeh et al., "The applications of anti-CD20 antibodies to treat various B cells disorders," Biomedicine & Pharmacotherapy 109 (2019) 2415-2426.
Pegram, H.J., et al., "Tumor-Targeted T Cells Modified to Secrete IL-12 Eradicate Systemic Tumors Without Need For Prior Conditioning," Blood 119(18):4133-4141 (2012).
Pizzolo and Roamgnani et al., "CD30 molecule (Ki-1 Ag): more than just a marker of CD30+ lymphoma," Haematologica 1995; 80:357-366.
Polonelli, L., et al., "Antibody Complementarity-Determining Regions (CDRs) Can Display Differential Antimicrobial, Antiviral and Antitumor Activities," PLoS One 3(6):e2371, pp. 1-9 (2008).
Porter et al., "Chimeric Antigen Receptor-Modified T Cells in Chronic Lymphoid Leukemia," N Engl J Med 2011;365:725-33.
Pouw et al., "TCR gene-engineered T cell: Limited T cell activation and combined use of IL-15 and IL-21 ensure minimal differentiation and maximal antigen-specificity," Molecular Immunology, Feb. 19, 2010, 47, pp. 1411-1420.
Preithner et al., "High concentrations of therapeutic IgG1 antibodies are needed to compensate for inhibition of antibody-dependent cellular cytotoxicity by excess endogenous immunoglobulin G," Mol Immunol., (2006) 43:1183-1193.
Prescribing label for KYMRIAH® (tisagenlecleucel), 24 pages (2017).
Product Leaflet, Dynabeads® CD3/CD28, 2018, 2 pages.
Raab et al., "Multiple myeloma," Lancet 2009; 374: 324-39.
Rajkumar, S.V., "Multiple Myeloma," Curr Probl Cancer 2009;33:7-64.
Ramos and Dotti, "Chimeric antigen receptor (CAR)-engineered lymphocytes for cancer therapy," Expert Opinion on Biological Therapy, (2011) 11:7, 855-873.
Rizoli, "PlasmaLyte," The Journal of Trauma, Injury, Infection, and Critical Care, vol. 70, No. 5, May Supplement 2011, 2 pages.
Rosenberg et al., "Personalized Cell Transfer Immunotherapy for B-Cell Malignancies and Solid Cancers," Molecular Therapy, Nov. 2011, vol. 19, No. 11, 1928-1930.
RosetteSep Data Sheet, 2018, 3 pages.
Sadelain, M., et al., "The Promise and Potential Pitfalls of Chimeric Antigen Receptors," Curr Opin Immunol. 21:215-223 (2009).
Saini, K., et al., "Beyond Trastuzumab: New Treatment Options for HER2-Positive Breast Cancer," The Breast 20: S20-S27, (2011).
Savoldo et al., "CD28 costimulation improves expansion and persistence of chimeric antigen receptor-modified T cells in lymphoma patients," J Clin Invest. 2011;121(5):1822-1826.
Schuler et al., "Separation of human CD4+CD39+ T cells by magnetic beads reveals two phenotypically and functionally different subsets," J. Immunol. Methods, Jun. 30, 2011, 369(1-2), 59-68, 19 pages.
Scott, A.M., et al., "Antibody Therapy of Cancer," Nat Rev Cancer 12:278-287 (2012).
Shirasu et al., "Construction and Molecular Characterization of Human Chimeric T-Cell Antigen Receptors Specific for Carcinoembryonic Antigen," Anticancer Research (2010) 33: 2731-2738.
Somerville et al., "Clinical scale rapid expansion of lymphocytes for adoptive cell transfer therapy in the WAVE® bioreactor," Journal of Translational Medicine, Apr. 4, 2012, 10:69, 11 pages.
Thistlethwaite et al., "Engineering T-cells with antibody-based chimeric receptors for effective cancer therapy," Current Opinion in Molecular Therapeutics 2005 7(1):48-55.
Till et al., "CD20-specific adoptive immunotherapy for lymphoma using a chimeric antigen receptor with both CD28 and 4-1BB domains: pilot clinical trial results," Blood, 2012; 119(17):3940-3950.
Van De Donk, N.W.C.J., et al., "Monoclonal antibody-based therapy as a new treatment strategy in multiple myeloma," Leukemia 26:199-213 (2012).
Verhoeyen et al., "Lentiviral Vector Gene Transfer Into Human T Cells," Methods in Molecular Biology, Methods and Protocols, 2009, vol. 506, pp. 97-114.
Westwood et al., "Adoptive transfer of T cells modified with a humanized chimeric receptor gene inhibits growth of Lewis-Y-expressing tumors in mice," PNAS, Dec. 27, 2005, vol. 102, No. 52, pp. 19051-19056.
Zhang et al., "Anti-melanoma activity of T cells redirected with a TCR-like chimeric antigen receptor," Scientific Reports, Jan. 6, 2014, 4: 3571, 8 pages.
Zhang et al., "Engineering CAR-T cells," Biomarker Research (2017) 5:22, 6 pages.
Zhao et al., "A herceptin-based chimeric antigen receptor with modified signaling domains leadsto enhanced survival of transduced T lymphocytes and antitumor activity," J Immunol 2009; 183:5563-5574.
Kalled Sequence Listing from WO 2010/104949 A2 (Sep. 16, 2010) ("Kalled Sequence Listing").
Chono et al., "Engineering of CD19-CAR T Cells from Non-HodgkinLymphoma Patients in a Closed System in Combinationwith Retronectin/OKT3 Stimulation," Blood, Dec. 6, 2014, vol. 124, Issue 21, 6 pages.
Chono et al., "Optimization of lentiviral vector transduction into peripheral blood mononuclear cells in combination with the fibronectin fragment CH-296 stimulation," J. Biochem., Nov. 23, 2010, 149(3), pp. 285-292.
Cieri et al., "IL-7 and IL-15 instruct the generation of human memory stem T cells from naive precursors," Blood, Jan. 24, 2013, 12 pages.
Dotti, et al., "Design and development of therapies using chimeric antigen receptor-expressing T cells." Immunol Rev. (2014); 257 (1): 107-126, 35 pages. First published: Dec. 13, 2013.
Field et al., "Comparison of Lentiviral and Sleeping Beauty Mediated αβ T Cell Receptor Gene Transfer," PLoS One, 8(6), Jun. 28, 2013, 9 pages.
Ho Y.J., et al., "Promoter usage regulating the surface density of CAR molecules may modulate the kinetics of CAR-T cells in vivo," Molecular Therapy, Methods & Clinical Development, Jun. 11, 2021, pp. 237-246, doi: 10.1016/j.omtm.2021.03.007. eCollection 2021.
June et al., "Engineering lymphocyte subsets: tools, trials and tribulations," Nature Reviews Immunology 9(10):704-716, Oct. 2009.
Min et al., "Molecular Targeted Tumor Therapy," Jinan: Shandong Science and Technology Press, Mar. 2009, 6 pages.
Park, T.S., et al., "Treating Cancer With Genetically Engineered T Cells," Trends in Biotechnology, Nov. 2011, vol. 29(11), pp. 550-557.
Shi et al., "Chimeric antigen receptor for adoptive immunotherapy of cancer: latest research and future prospects," Molecular Cancer 2014, 13:219, 8 pages.
Tumeh et al., "The impact of ex vivo clinical grade activation protocols on human T cell phenotype and function for the generation of genetically modified cells for adoptive cell transfer therapy," J Immunother., Oct. 2010, 33(8):759-68.
Walpole et al., "The weight of nations: an estimation of adult human biomass," BMC Public Health, 2012, vol. 12, p. 439.
Washington et al., "Innate Immune Factors Are Expressed among Peripheral BloodCD34 + HSCs, Are Induced upon Exposure to Lentiviral Vectors and May Limit Transduction Efficiency," Blood, Nov. 16, 2007, vol. 110, Issue 11, 6 pages.
Xue et al., "ZSTK474, a novel PI3K inhibitor, modulates human CD14+ monocyte-derived dendritic cell functions and suppresses experimental autoimmune encephalomyelitis," J Mol Med, May 22, 2014, 92:1057-1068.

(56) References Cited

OTHER PUBLICATIONS

Yang, S., "In vitro generated anti-tumor T lymphocytes exhibit distinct subsets mimicking in vivo antigen-experienced cells", Cancer Immunol Immunother (2011) 60:739-749.

Brudno et al., "T cells genetically modified to express an anti-B-cell maturation antigen chimeric antigen receptor cause remissions of poor-prognosis relapsed multiple myeloma", Journal of Clinical Oncology 36(22): 2267 (2018).

Duong et al., "Peripheral blood progenitor cell mobilization for autologous and allogeneic hematopoietic cell transplantation: guidelines from the American Society for Blood and Marrow Transplantation." Biology of Blood and Marrow Transplantation 20(9) (2014): 1262-1273.

Extended European Search Report for EP Application No. 21187802.0 dated Feb. 18, 2022, 14 pages.

Extended European Search Report for EP Application No. 21198992.6 dated Apr. 20, 2022, 15 pages.

Kleiveland, "Peripheral blood mononuclear cells." The Impact of Food Bioactives on Health: in vitro and ex vivo models (2015).

Morgan et al., "Engineering CAR-T Cells for Improved Function Against Solid Tumors", Frontiers in Immunology, Oct. 29, 2018, vol. 9, Art. 2493, pp. 1-11.

Munshi et al., "Idecabtagene Vicleucel in Relapsed and Refractory Multiple Myeloma", New England Journal of Medicine, 2021; 384:705-716.

Notice Regarding the General Guideline Relating to Clinical Evaluation of New Pharmaceuticals, Yakushinyako No. 43, Notice from the Chief of the Section of New Pharmaceuticals, the Department of Pharmaceutical Affair, the Ministry of Health, Labour and Welfare to the chief of the Main Department of Sanitation Control of each prefecture, 1992, pp. 1-12.

Polyak et al., "Overview: Gene Structure." Holland-Frei Cancer Medicine. 6th edition (2003).

Raje et al., "Anti-BCMA CAR T-Cell Therapy bb2121 in Relapsed or Refractory Multiple Myeloma", New England Journal of Medicine, 2019; 380: 1726-1737.

Rodriguez-Otero et al., "Ide-cel or Standard Regimens in Relapsed and Refractory Multiple Myeloma", New England Journal of Medicine, 2023; 388: 1002-1014.

Gschweng et al., "Hematopoietic stem cells for cancer immunotherapy," Immunological Reviews 257.1 (2013): 237-249.

Tsuruta et al., "Recent Advances in Hematopoietic Stem Cell Gene Therapy," In: Innovations in Stem Cell Transplantation, InTech (2013): 107-135.

\* cited by examiner

METHODS FOR MANUFACTURING ADOPTIVE CELL THERAPIES

CROSS REFERENCE TO RELATED APPLICATIONS

This application is the National Stage of International Application No. PCT/US2015/027518, filed Apr. 24, 2015, which claims the benefit under 35 U.S.C. § 119 (e) of U.S. Provisional Application No. 61/984,558, filed Apr. 25, 2014, each of which is incorporated by reference herein in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is BLBD_028_01WO_ST25.txt. The text file is 3 KB, was created on Apr. 24, 2015, and is being submitted electronically via EFS-Web, concurrent with the filing of the specification.

BACKGROUND

Technical Field

The present invention relates to improved platforms and associated methods for manufacturing immune effector cells. More particularly, the invention relates to scalable, flexible, reliable, and reproducible methods for manufacturing therapeutic immune effector cell compositions comprising T cells.

Description of the Related Art

Adoptive immunotherapy or adoptive cellular therapy (ACT) is the transfer of gene modified T lymphocytes to a subject for the therapy of disease. Adoptive immunotherapy has yet to realize its potential for treating a wide variety of diseases including cancer, infectious disease, autoimmune disease, inflammatory disease, and immunodeficiency. However, most, if not all adoptive immunotherapy strategies require T cell activation and expansion steps to generate a clinically effective, therapeutic dose of T cells. Due to the inherent complexity of live cell culture and patient to patient variability, current technologies for generating therapeutic doses of T cells, including engineered T cells, remain limited by cumbersome T cell manufacturing processes. Existing T cell manufacturing processes are not easily scalable, repeatable, reliable, or efficient and often produce an inferior T cell product that may be prone to exhaustion and loss of effector immune cell function.

To date, engineered T cell adoptive immunotherapies have met with only limited success and routinely show variable clinical activity. Therefore, such therapies are not suitable for widespread clinical use.

BRIEF SUMMARY

The invention generally provides methods for adoptive cellular therapy.

In various embodiments, a method for manufacturing a T cell therapeutic is provided comprising: obtaining a population of cells that comprises T cells and antigen presenting cells (APCs); culturing the population of cells in a cell culture medium comprising i) one or more cytokines, ii) an anti-CD3 antibody or CD3-binding fragment thereof, and iii) an anti-CD28 antibody or a CD28-binding fragment thereof, B7-1 or a CD28-binding fragment thereof, or B7-2 or a CD28-binding fragment thereof, wherein the culture activates and stimulates the T cells; transducing the population of activated cells with a viral vector; and culturing the population of cells in a cell growth medium to expand the transduced T cells; thereby manufacturing the T cell therapeutic.

In particular embodiments, the population of cells is obtained from peripheral blood, peripheral blood mononuclear cells, bone marrow, lymph nodes tissue, cord blood, thymus issue, tissue from a site of infection, ascites, pleural effusion, spleen tissue, or tumors.

In certain embodiments, the T cells are obtained from peripheral blood, peripheral blood mononuclear cells, bone marrow, lymph nodes tissue, cord blood, thymus issue, tissue from a site of infection, ascites, pleural effusion, spleen tissue, tumors, or a T cell line.

In additional embodiments, the APCs are obtained from peripheral blood, peripheral blood mononuclear cells, bone marrow, lymph nodes tissue, cord blood, thymus issue, tissue from a site of infection, ascites, pleural effusion, spleen tissue, or tumors.

In some embodiments, the population of cells comprises peripheral blood mononuclear cells (PBMCs).

In further embodiments, harvesting or obtaining the population of cells comprises leukapheresis.

In particular embodiments, isolating the population of cells comprises sedimentation.

In additional embodiments, the sedimentation comprises a FICOLL™ or a PERCOLL™ gradient.

In certain embodiments, the sedimentation is performed using a semiautomated flowthrough centrifuge.

In additional embodiments, the semiautomated flow-through centrifuge is a Cobe 2991 cell processor, a Cell Saver 5+, or a Teruma Elutra.

In particular embodiments, the methods further comprise washing the population of cells in a buffer or cell culture medium.

In some embodiments, the population of cells are washed in T cell growth medium (TCGM) containing one or more cytokines.

In some embodiments, the one or more cytokines in the TCGM are selected from the group consisting of: IL-2, IL7, IL-15, IL-9, and IL-21.

In particular embodiments, the cytokine is IL-2.

In certain embodiments, the concentration of IL-2 is about 250 IU/mL.

In certain embodiments, the concentration of IL-2 is about from 100 IU/mL to about 300 IU/mL.

In some embodiments, the isolated population of cells comprises PBMCs.

In additional embodiments, the population of cells is cryopreserved in a controlled rate freezer.

In further embodiments, the cryopreserved population of cells is thawed.

In further embodiments, the population of cells is seeded for culturing in step (b) in TCGM at a density of about $1 \times 10^8$ cells/mL.

In further embodiments, the population of cells is seeded for culturing in step (b) in TCGM at a density of about $1 \times 10^7$ cells/mL.

In further embodiments, the population of cells is seeded for culturing in step (b) in TCGM at a density of about $1\times10^6$ cells/mL.

In further embodiments, about $1\times10^8$ cells are seeded for culturing in step (b) in TCGM at a density of about $1\times10^6$ cells/mL.

In particular embodiments, the population of cells is cultured in a cell culture bag or a bioreactor.

In certain embodiments, the TCGM comprises one or more cytokines selected from the group consisting of: IL-2, IL7, IL-15, IL-9, and IL-21.

In further embodiments, the one or more cytokines are selected from the group consisting of: IL-2, IL-7, and IL-15.

In additional embodiments, the one or more cytokines comprise IL-2.

In additional embodiments, the concentration of the one or more cytokines is about 250 IU/mL.

In additional embodiments, the concentration of the one or more cytokines is about from 25 IU/mL to about 500 IU/mL In further embodiments, the population of cells is cultured with a soluble anti-CD3 antibody and a soluble anti-CD28 antibody.

In certain embodiments, the concentration of the anti-CD3 antibody is about 50 ng/mL.

In particular embodiments, the concentration of the anti-CD28 antibody is about 50 ng/mL.

In particular embodiments, the population of cells of step b) is cultured for about 12 hours to about 48 hours prior to transduction.

In further embodiments, the population of cells of step b) is cultured for about 16 hours to about 32 hours prior to transduction.

In additional embodiments, the population of cells of step b) is cultured for at least 18 hours prior to transduction.

In further embodiments, the population of cells of step b) is cultured for at least 24 hours prior to transduction.

In certain embodiments, the population of cells of step d) is transduced with a retroviral vector.

In certain embodiments, the population of cells of step d) is transduced with a lentiviral vector.

In further embodiments, about $1\times10^9$ TU to about $2\times10^9$ TU of viral vector are used to transduce the $1\times10^8$ seeded cells.

In further embodiments, about $1\times10^9$ TU to about $4\times10^9$ TU of viral vector are used to transduce the $1\times10^8$ seeded cells.

In particular embodiments, the viral vector is diluted to 20% v/v of the total culture volume.

In particular embodiments, the viral vector is diluted to about 20% to about 40% v/v of the total culture volume.

In additional embodiments, the population of cells is transduced for about 18 to about 48 hours.

In further embodiments, the population of cells is transduced for about 18 to about 36 hours.

In further embodiments, the population of cells is transduced for about 24 hours.

In additional embodiments, the viral vector comprises a polynucleotide encoding a chimeric antigen receptor.

In certain embodiments, the CAR comprises: an extracellular domain that binds an antigen selected from the group consisting of: alpha folate receptor, 5T4, αvβ6 integrin, BCMA, B7-H3, B7-H6, CAIX, CD19, CD20, CD22, CD30, CD33, CD44, CD44v6, CD44v7/8, CD70, CD79a, CD79b, CD123, CD138, CD171, CEA, CSPG4, EGFR, EGFR family including ErbB2 (HER2), EGFRvIII, EGP2, EGP40, EPCAM, EphA2, EpCAM, FAP, fetal AchR, FRα, GD2, GD3, 'Glypican-3 (GPC3), HLA-A1+MAGE1, HLA-A2+MAGE1, HLA-A3+MAGE1, HLA-A1+NY-ESO-1, HLA-A2+NY-ESO-1, HLA-A3+NY-ESO-1, IL-11Rα, IL-13Rα2, Lambda, Lewis-Y, Kappa, Mesothelin, Muc1, Muc16, NCAM, NKG2D Ligands, NY-ESO-1, PRAME, PSCA, PSMA, ROR1, SSX, Survivin, TAG72, TEMs, and VEGFR2; a transmembrane domain derived from a polypeptide selected from the group consisting of: CD8α; CD4, CD28, CD45, PD1, and CD152; one or more intracellular co-stimulatory signaling domains selected from the group consisting of: CD28, CD54 (ICAM), CD134 (OX40), CD137 (41BB), CD152 (CTLA4), CD273 (PD-L2), CD274 (PD-L1), and CD278 (ICOS); and a CD3ζ signaling domain.

In particular embodiments, the extracellular domain comprises an antibody or antigen binding fragment that binds the antigen.

In further embodiments, the transmembrane domain is derived from CD8α or CD28.

In certain embodiments, the one or more co-stimulatory signaling domains selected from the group consisting of: CD28, CD134, and CD137.

In further embodiments, comprising a hinge region polypeptide.

In additional embodiments, the hinge region polypeptide comprises a hinge region of IgG1 or CD8α.

In particular embodiments, the CAR further comprises a signal peptide.

In particular embodiments, the signal peptide comprises an IgG1 heavy chain signal polypeptide, a CD8α signal polypeptide, or a human GM-CSF receptor alpha signal polypeptide.

In additional embodiments, the population of cells in step d) is cultured for expansion for about 5 to about 8 days.

In certain embodiments, the population of cells in step d) is cultured for expansion for about 5 days to about 8 days in a cell culture bag.

In further embodiments, the population of cells in step d) is cultured for expansion for about 5 days in a cell culture bag and then cultured for about 3 days in a bioreactor.

In additional embodiments, the population of cells in step d) is cultured for expansion for about 5 days to about 8 days in a bioreactor.

In further embodiments, the bioreactor is a WAVE bioreactor or a GREX bioreactor.

In particular embodiments, the number of T cells is expanded at least 50 fold during the culture of step d).

In certain embodiments, the number of T cells is expanded at least 100 fold during the culture of step d).

In particular embodiments, the number of T cells is expanded at least 200 fold during the culture of step d).

In further embodiments, the number of T cells is expanded at least 300 fold during the culture of step d).

In additional embodiments, the number of T cells is expanded at least 400 fold during the culture of step d).

In additional embodiments, the number of T cells is expanded at least 500 fold during the culture of step d).

In further embodiments, the number of T cells is expanded at least 600 fold during the culture of step d).

In certain embodiments, the method further comprises recovering the manufactured T cell therapeutic.

In certain embodiments, recovering the T cell therapeutic comprises concentrating and washing the cells expanded in step d).

In particular embodiments, the T cell therapeutic is concentrated and washed using a semiautomated flowthrough centrifuge.

In further embodiments, the semiautomated flowthrough centrifuge is a Cell Saver 5+ or LOVO.

In particular embodiments, the method further comprises cryopreserving the T cell therapeutic.

In additional embodiments, the cryopreserved T cells are thawed for use in a method of adoptive cell therapy.

In various embodiments, a composition comprising the manufactured T cells of any one of the preceding embodiments described supra and elsewhere herein and a physiologically acceptable excipient is provided.

In various other embodiments, a method of treating a malignancy in a subject in need thereof, comprising administering to the subject the T cell therapeutic of any one of the preceding embodiments described supra and elsewhere herein is provided.

DETAILED DESCRIPTION

A. Overview

Figure 1:
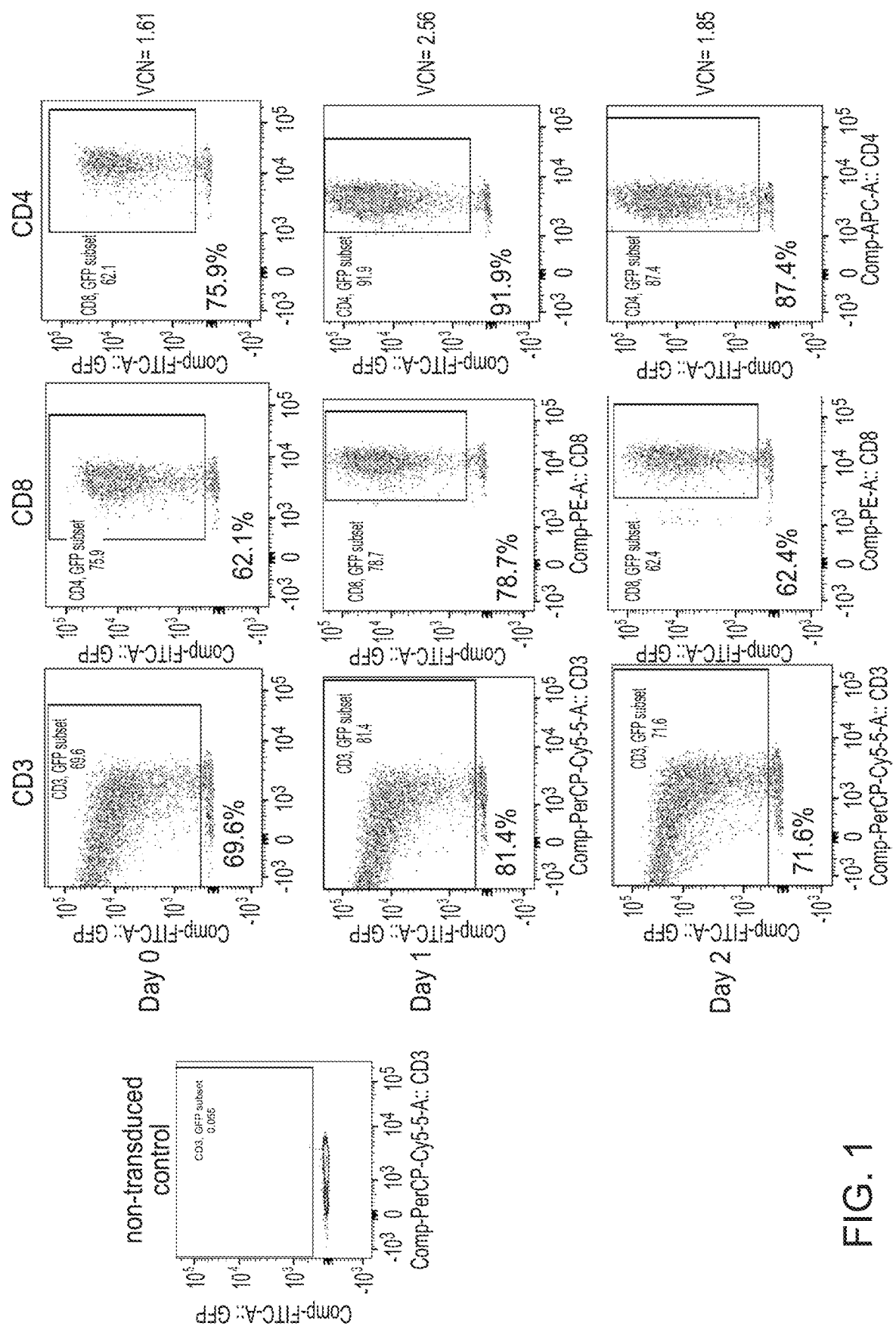
FIG. 1 shows transduction efficiency and VCN of transduced cells transduced at different times during the T cell manufacturing process. Cells were transduced with a GFP expressing lentivirus at $1-2\times10^8$ TU/$10^6$ PBMCs at D0, D1, and D2. FACS analysis of GFP expressing cells expressing CD3, CD8, or CD4 determined that transduction efficiency and VCN were highest in cells transduced 20 to 24 hours (D1) after activation.

Existing methods for manufacturing adoptive cell therapies are cumbersome and expensive and have presented a formidable barrier to the use of ACT as a widespread treatment in the clinic. The compositions and methods offer a solution to these and other problems related to manufacturing cell-based therapeutics. The invention generally relates to improved methods for manufacturing T cell therapeutics. Without wishing to be bound to any particular theory, the inventive methods contemplated herein result in a reproducible, reliable, and robust ACT manufacturing platform, compared to existing T cell compositions in the art.

In various embodiments, methods for manufacturing adoptive cellular therapies, immune effector cell compositions or therapeutics, methods for expanding immune effector cells, and immune effector cell manufacturing platforms are provided. In particular preferred embodiments, an engineered TCR or CAR immune effector cell composition is manufactured by the methods contemplated herein, which may further increase the efficacy of an immune effector cell adoptive cellular therapy. Manufactured cell compositions contemplated herein are useful in the treatment or prevention of numerous conditions including, but not limited to cancer, infectious disease, autoimmune disease, inflammatory disease, and immunodeficiency.

In various embodiments, a method for manufacturing a therapeutic composition comprising immune effector cells involves obtaining a population of cells comprising immune effector cells, activating the population of cells, and culturing the population of cells to expand immune effector cells. In particular embodiments, the immune effector cells comprise T cells, and optionally NK cells and/or NKT cells.

In various embodiments, immune effector cells are manufactured in cell culture bags and/or bioreactors.

In other various embodiments, immune effector cells are manufactured in bioreactors.

In one embodiment, a method for manufacturing a therapeutic composition comprising T cells comprises harvesting cells from a subject and isolating a population of cells using a closed system process. In particular embodiments, cells may be isolated from any suitable fresh or frozen sources. In certain embodiments, the isolated population of cells comprises peripheral blood mononuclear cells (PBMCs). The isolated population of cells is seeded to initiate cultures and T cells are activated and stimulated by contacting the cells with primary and costimulatory ligands. In particular embodiments, populations of cells comprising activated T cells are transduced with a viral vector in order to redirect the transduced cells to a particular target antigen. In certain embodiments, the cells are transduced with a viral vector encoding a CAR or engineered TCR. Transduced cells or non-transduced cells may then be cultured in growth medium to expand immune effector cells, e.g., T cells. Manufactured immune effector cell compositions may then be used to treat subjects in need thereof or frozen for later use.

Adoptive cellular therapies manufactured using the methods contemplated herein are effective in producing cellular drug products with reproducible levels of expansion, cellular profiles, VCN, and that are effective in mediating antigen-specific tumor clearance.

The methods offer reduced patient-to-patient variability in producing adoptive cellular therapies and are reproducible, reliable, scalable, and transferrable to cGMP manufacturing processes. Accordingly, the methods and compositions contemplated herein represent a quantum improvement compared to existing adoptive cell immunotherapies.

The practice of the invention will employ, unless indicated specifically to the contrary, conventional methods of chemistry, biochemistry, organic chemistry, molecular biology, microbiology, recombinant DNA techniques, genetics, immunology, and cell biology that are within the skill of the art, many of which are described below for the purpose of illustration. Such techniques are explained fully in the literature. See, e.g., Sambrook, et al., *Molecular Cloning: A Laboratory Manual* (3rd Edition, 2001); Sambrook, et al., *Molecular Cloning: A Laboratory Manual* (2nd Edition, 1989); Maniatis et al., *Molecular Cloning: A Laboratory Manual* (1982); Ausubel et al., *Current Protocols in Molecular Biology* (John Wiley and Sons, updated July 2008); *Short Protocols in Molecular Biology: A Compendium of Methods from Current Protocols in Molecular Biology*, Greene Pub. Associates and Wiley-Interscience; Glover, *DNA Cloning: A Practical Approach*, vol. I & II (IRL Press, Oxford, 1985); Anand, *Techniques for the Analysis of Complex Genomes*, (Academic Press, New York, 1992); *Transcription and Translation* (B. Hames & S. Higgins, Eds., 1984); Perbal, *A Practical Guide to Molecular Cloning* (1984); Harlow and Lane, *Antibodies*, (Cold Spring Harbor Laboratory Press, Cold Spring Harbor, N.Y., 1998) *Current Protocols in Immunology* Q. E. Coligan, A. M. Kruisbeek, D. H. Margulies, E. M. Shevach and W. Strober, eds., 1991); *Annual Review of Immunology*; as well as monographs in journals such as *Advances in Immunology*.

All publications, patents and patent applications cited herein are hereby incorporated by reference in their entirety.

B. Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred embodiments of compositions, methods and materials are described herein. For the purposes of the present invention, the following terms are defined below.

The articles "a," "an," and "the" are used herein to refer to one or to more than one (i.e., to at least one) of the grammatical object of the article. By way of example, "an element" means one element or more than one element.

As used herein, the term "about" or "approximately" refers to a quantity, level, value, number, frequency, percentage, dimension, size, amount, weight or length that varies by as much as 30, 25, 20, 25, 10, 9, 8, 7, 6, 5, 4, 3, 2 or 1% to a reference quantity, level, value, number, frequency, percentage, dimension, size, amount, weight or length. In particular embodiments, the terms "about" or "approximately" when preceding a numerical value indicates the value plus or minus a range of 15%, 10%, 5%, or 1%.

As used herein, the term "substantially" refers to a quantity, level, value, number, frequency, percentage, dimension, size, amount, weight or length that is 80%, 85%, 90%, 91%, 92%, 93%, 94%, 95%, 96%, 97%, 98%, 99% or higher of a reference quantity, level, value, number, frequency, percentage, dimension, size, amount, weight or length. In one embodiment, "substantially the same" refers to a quantity, level, value, number, frequency, percentage, dimension, size, amount, weight or length that produces an effect, e.g., a physiological effect, that is approximately the same as a reference quantity, level, value, number, frequency, percentage, dimension, size, amount, weight or length.

Throughout this specification, unless the context requires otherwise, the words "comprise", "comprises" and "comprising" will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are optional and may or may not be present depending upon whether or not they affect the activity or action of the listed elements Reference throughout this specification to "one embodiment," "an embodiment," "a particular embodiment," "a related embodiment," "a certain embodiment," "an additional embodiment," or "a further embodiment" or combinations thereof means that a particular feature, structure or characteristic described in connection with the embodiment is included in at least one embodiment of the present invention. Thus, the appearances of the foregoing phrases in various places throughout this specification are not necessarily all referring to the same embodiment. Furthermore, the particular features, structures, or characteristics may be combined in any suitable manner in one or more embodiments.

As used herein, the terms "T cell manufacturing" or "methods of manufacturing T cells or comparable terms refer to the process of producing a therapeutic composition of T cells, which manufacturing methods may comprise one or more of, or all of the following steps performed one or more times on a population of cells comprising T cells or a population of purified T cells: harvesting, isolating, washing, stimulating, activating, modifying, expanding, cryopreserving, and thawing, or any suitable combination thereof.

The terms "T cell" or "T lymphocyte" are art-recognized and are intended to include thymocytes, naïve T lymphocytes, immature T lymphocytes, mature T lymphocytes, resting T lymphocytes, or activated T lymphocytes. Illustrative populations of T cells suitable for use in particular embodiments include but are not limited to helper T cells (HTL; $CD4^+$ T cell), a cytotoxic T cell (CTL; $CD8^+$ T cell), $CD4+CD8^+$ T cell, $CD4-CD8^-$ T cell, or any other subset of T cells. Other illustrative populations of T cells suitable for use in particular embodiments include but are not limited to T cells expressing one or more of the following markers: CD3, CD4, CD8, CD27, CD28, CD45RA, CD45RO, CD62L, CD127, CD197, and HLA-DR and if desired, can be further isolated by positive or negative selection techniques.

A peripheral blood mononuclear cell (PBMC) is defined as any blood cell with a round nucleus (i.e., a lymphocyte, a monocyte, or a macrophage). These blood cells are a critical component in the immune system to fight infection and adapt to intruders. The lymphocyte population consists of CD4+ and CD8+ T cells, B cells and Natural Killer cells, CD14+ monocytes, and basophils/neutrophils/eosinophils/dendritic cells. These cells are often separated from whole blood or from leukopacks using FICOLL™, a hydrophilic polysaccharide that separates layers of blood, with monocytes and lymphocytes forming a buffy coat under a layer of plasma. In one embodiment, "PBMCs" refers to a population of cells comprising at least T cells, and optionally NK cells, and antigen presenting cells.

"Antigen-presenting cells" refer to a heterogeneous group of immunocompetent cells that mediate the cellular immune response by processing and presenting antigens to the T-cells. Antigen-presenting cells include, but are not limited to macrophages, dendritic cells, langerhans cells, B-lymphocytes, platelets and artificial antigen presenting cells (aAPC).

aAPCs may be made by engineering K562, U937, 721.221, T2, and C1R cells to direct the stable expression and secretion, of a variety of costimulatory molecules and cytokines. In a particular embodiment, K32 or U32 aAPCs are used to direct the display of one or more antibody-based stimulatory molecules on the AAPC cell surface. Populations of T cells can be expanded by aAPCs expressing a variety of costimulatory molecules including, but not limited to, CD137L (4-1BBL), CD134L (OX40L), and/or CD80 or CD86. Finally, the aAPCs provide an efficient platform to expand genetically modified T cells and to maintain CD28 expression on CD8 T cells. aAPCs provided in WO 03/057171 and US2003/0147869 are hereby incorporated by reference in their entirety.

As used herein, the term "proliferation" refers to an increase in cell division, either symmetric or asymmetric division of cells. In particular embodiments, "proliferation" refers to the symmetric or asymmetric division of T cells. "Increased proliferation" occurs when there is an increase in the number of cells in a treated sample compared to cells in a non-treated sample.

An "immune effector cell," is any cell of the immune system that has one or more effector functions (e.g., cytotoxic cell killing activity, secretion of cytokines, induction of ADCC and/or CDC). The illustrative immune effector cells contemplated herein are T lymphocytes, in particular cytotoxic T cells (CTLs; $CD8^+$ T cells) and helper T cells (HTLs; $CD4^+$ T cells). As would be understood by the skilled person, other cells may also be used as immune effector cells with the CARs as described herein. In particular, immune effector cells also include NK cells, NKT cells, neutrophils, and macrophages. In particular embodiments, T cells and one or more other cell types such as NK cells, NKT cells, neutrophils, and/or macrophages are genetically modified and expanding using the manufacturing methods contemplated herein.

"Modified T cells" refer to T cells that have been modified by the introduction of a polynucleotide encoding an engineered TCR or CAR contemplated herein. Modified T cells include both genetic and non-genetic modifications (e.g., episomal or extrachromosomal).

As used herein, the term "genetically engineered" or "genetically modified" refers to the addition of extra genetic material in the form of DNA or RNA into the total genetic material in a cell.

The terms, "genetically modified cells," "modified cells," and, "redirected cells," are used interchangeably.

As used herein, the term "gene therapy" refers to the introduction of extra genetic material in the form of DNA or RNA into the total genetic material in a cell that restores, corrects, or modifies expression of a gene, or for the purpose of expressing a therapeutic polypeptide, e.g., a TCR or CAR and/or one or more cytokines. In particular embodiments, T cells are modified to express an engineered TCR or CAR without modifying the genome of the cells, e.g., by introducing an episomal vector that expresses the TCR or CAR into the cell.

The term "ex vivo" refers generally to activities that take place outside an organism, such as experimentation or measurements done in or on living tissue in an artificial environment outside the organism, preferably with minimum alteration of the natural conditions. In particular embodiments, "ex vivo" procedures involve living cells or tissues taken from an organism and cultured or modulated in a laboratory apparatus, usually under sterile conditions, and typically for a few hours or up to about 24 hours, but including up to 48 or 72 hours, depending on the circumstances. In certain embodiments, such tissues or cells can be collected and frozen, and later thawed for ex vivo treatment. Tissue culture experiments or procedures lasting longer than a few days using living cells or tissue are typically considered to be "in vitro," though in certain embodiments, this term can be used interchangeably with ex vivo.

The term "in vivo" refers generally to activities that take place inside an organism, such as cell self-renewal and expansion of cells. In one embodiment, the term "in vivo expansion" refers to the ability of a cell population to increase in number in vivo.

The term "stimulation" refers to a primary response induced by binding of a stimulatory molecule (e.g., a TCR/CD3 complex) with its cognate ligand thereby mediating a signal transduction event including, but not limited to, signal transduction via the TCR/CD3 complex.

A "stimulatory molecule," refers to a molecule on a T cell that specifically binds with a cognate stimulatory ligand.

A "stimulatory ligand," as used herein, means a ligand that when present on an antigen presenting cell (e.g., an aAPC, a dendritic cell, a B-cell, and the like) can specifically bind with a cognate binding partner (referred to herein as a "stimulatory molecule") on a T cell, thereby mediating a primary response by the T cell, including, but not limited to, activation, initiation of an immune response, proliferation, and the like. Stimulatory ligands include, but are not limited to CD3 ligands or binding agents, e.g., an anti-CD3 antibody and CD2 ligands or binding agents, e.g., anti-CD2 antibody.

The term, "activation" refers to the state of a T cell that has been sufficiently stimulated to induce detectable cellular proliferation. In particular embodiments, activation can also be associated with induced cytokine production, and detectable effector functions. The term "activated T cells" refers to, among other things, T cells that are proliferating. Signals generated through the TCR alone are insufficient for full activation of the T cell and one or more secondary or costimulatory signals are also required. Thus, T cell activation comprises a primary stimulation signal through the TCR/CD3 complex and one or more secondary costimulatory signals. Costimulation can be evidenced by proliferation and/or cytokine production by T cells that have received a primary activation signal, such as stimulation through the CD3/TCR complex or through CD2.

A "costimulatory signal," refers to a signal, which in combination with a primary signal, such as TCR/CD3 ligation, leads to T cell proliferation, cytokine production, and/or upregulation or downregulation of particular molecules.

A "costimulatory ligand," refers to a molecule that binds a costimulatory molecule. A costimulatory ligand may be soluble or provided on a surface. A co-stimulatory ligand can include, but is not limited to, CD7, B7-1 (CD80), B7-2 (CD86), PD-L1, PD-L2, 4-1BBL, OX40L, inducible costimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, an agonist or antibody that binds Toll ligand receptor and a ligand that specifically binds with B7-H3. A co-stimulatory ligand also encompasses, inter alia, an antibody or antigen binding fragment thereof that specifically binds with a co-stimulatory molecule present on a T cell, such as, but not limited to, CD27, CD28, 4-1BB, OX40, CD30, CD40, PD-1, ICOS, lymphocyte function-associated antigen-1 (LFA-1), CD2, CD7, LIGHT, NKG2C, B7-H3, and a ligand that specifically binds with CD83.

A "costimulatory molecule" refers to the cognate binding partner on a T cell, e.g., CD28 that specifically binds with a costimulatory ligand, thereby mediating a co-stimulatory response by the T cell, including, but not limited to, proliferation.

"Autologous," as used herein, refers to cells from the same subject.

"Allogeneic," as used herein, refers to cells of the same species that differ genetically to the cell in comparison.

"Syngeneic," as used herein, refers to cells of a different subject that are genetically identical to the cell in comparison.

"Xenogeneic," as used herein, refers to cells of a different species to the cell in comparison.

As used herein, the terms "individual" and "subject" are often used interchangeably and refer to any animal that exhibits a symptom of a cancer, infectious disease, immunodeficiency, inflammatory disease, or auto-immune disorder that can be treated with the gene therapy vectors, cell-based therapeutics, and methods disclosed elsewhere herein. Suitable subjects (e.g., patients) include laboratory animals (such as mouse, rat, rabbit, or guinea pig), farm animals, and domestic animals or pets (such as a cat or dog). Non-human primates and, preferably, humans, are included. Typical subjects include humans that have a cancer, infectious disease, immunodeficiency, inflammatory disease, or auto-immune disorder, that have been diagnosed with a cancer, infectious disease, immunodeficiency, inflammatory disease, or auto-immune disorder, or that are at risk or having a cancer, infectious disease, immunodeficiency, inflammatory disease, or auto-immune disorder.

As used herein, the term "patient" refers to a subject that has been diagnosed with a particular indication that can be treated with the gene therapy vectors, cell-based therapeutics, and methods disclosed elsewhere herein.

As used herein "treatment" or "treating," includes any beneficial or desirable effect on the symptoms or pathology of a disease or pathological condition, and may include even minimal reductions in one or more measurable markers of the disease or condition being treated, e.g., cancer. Treatment can involve optionally either amelioration of, or complete reduction of, one or more symptoms of the disease or condition, or the delaying of the progression of the disease or condition. "Treatment" does not necessarily indicate complete eradication or cure of the disease or condition, or associated symptoms thereof.

As used herein, "prevent," and similar words such as "prevented," "preventing" etc., indicate an approach for preventing, inhibiting, or reducing the likelihood of the occurrence or recurrence of, a disease or condition, e.g., cancer. It also refers to delaying the onset or recurrence of a disease or condition or delaying the occurrence or recurrence of the symptoms of a disease or condition. As used herein, "prevention" and similar words also includes reducing the intensity, effect, symptoms and/or burden of a disease or condition prior to onset or recurrence of the disease or condition.

As used herein, the term "amount" refers to "an amount effective" or "an effective amount" of a genetically modified therapeutic cell, e.g., T cell, to achieve a beneficial or desired prophylactic or therapeutic result, including clinical results.

A "prophylactically effective amount" refers to an amount of a genetically modified therapeutic cell effective to achieve the desired prophylactic result. Typically but not necessarily, since a prophylactic dose is used in subjects prior to or at an earlier stage of disease, the prophylactically effective amount is less than the therapeutically effective amount.

A "therapeutically effective amount" of a genetically modified therapeutic cell may vary according to factors such as the disease state, age, sex, and weight of the individual, and the ability of the T cells to elicit a desired response in the individual. A therapeutically effective amount is also one in which any toxic or detrimental effects of the virus or transduced therapeutic cells are outweighed by the therapeutically beneficial effects. The term "therapeutically effective amount" includes an amount that is effective to "treat" a subject (e.g., a patient). When a therapeutic amount is indicated, the precise amount of the compositions of the present invention to be administered can be determined by a physician with consideration of individual differences in age, weight, tumor size, extent of infection or metastasis, and condition of the patient (subject).

As used herein, the term "cancer" relates generally to a class of diseases or conditions in which abnormal cells divide without control and can invade nearby tissues.

As used herein, the term "malignant" refers to a cancer in which a group of tumor cells display one or more of uncontrolled growth (i.e., division beyond normal limits), invasion (i.e., intrusion on and destruction of adjacent tissues), and metastasis (i.e., spread to other locations in the body via lymph or blood). As used herein, the term "metastasize" refers to the spread of cancer from one part of the body to another. A tumor formed by cells that have spread is called a "metastatic tumor" or a "metastasis." The metastatic tumor contains cells that are like those in the original (primary) tumor.

As used herein, the term "benign" or "non-malignant" refers to tumors that may grow larger but do not spread to other parts of the body. Benign tumors are self-limited and typically do not invade or metastasize.

A "cancer cell" or "tumor cell" refers to an individual cell of a cancerous growth or tissue. A tumor refers generally to a swelling or lesion formed by an abnormal growth of cells, which may be benign, pre-malignant, or malignant. Most cancers form tumors, but some, e.g., leukemia, do not necessarily form tumors. For those cancers that form tumors, the terms cancer (cell) and tumor (cell) are used interchangeably. The amount of a tumor in an individual is the "tumor burden" which can be measured as the number, volume, or weight of the tumor.

An "infectious disease" refers to a disease that can be transmitted from person to person or from organism to organism, and is caused by a microbial agent (e.g., common cold). Infectious diseases are known in the art and include, for example, hepatitis, sexually transmitted diseases (e.g., Chlamydia, gonorrhea), tuberculosis, HIV/AIDS, diphtheria, hepatitis B, hepatitis C, cholera, and influenza.

An "autoimmune disease" refers to a disease in which the body produces an immunogenic (i.e., immune system) response to some constituent of its own tissue. In other words the immune system loses its ability to recognize some tissue or system within the body as "self" and targets and attacks it as if it were foreign. Autoimmune diseases can be classified into those in which predominantly one organ is affected (e.g., hemolytic anemia and anti-immune thyroiditis), and those in which the autoimmune disease process is diffused through many tissues (e.g., systemic lupus erytnematosus). For example, multiple sclerosis is thought to be caused by T cells attacking the sheaths that surround the nerve fibers of the brain and spinal cord. This results in loss of coordination, weakness, and blurred vision. Autoimmune diseases are known in the art and include, for instance, Hashimoto's thyroiditis, Grave's disease, lupus, multiple sclerosis, rheumatic arthritis, hemolytic anemia, anti-immune thyroiditis, systemic lupus erythematosus, celiac disease, Crohn's disease, colitis, diabetes, scleroderma, psoriasis, and the like.

An "immunodeficiency" means the state of a patient whose immune system has been compromised by disease or by administration of chemicals. This condition makes the system deficient in the number and type of blood cells needed to defend against a foreign substance. Immunodeficiency conditions or diseases are known in the art and include, for example, AIDS (acquired immunodeficiency syndrome), SCID (severe combined immunodeficiency disease), selective IgA deficiency, common variable immunodeficiency, X-linked agammaglobulinemia, chronic granulomatous disease, hyper-IgM syndrome, and diabetes.

As used herein, the term "inflammatory disease" refers to either an acute or chronic inflammatory condition, which can result from infections or non-infectious causes. Various infectious causes include meningitis, encephalitis, uveitis, colitis, tuberculosis, dermatitis, and adult respiratory distress syndrome. Non-infectious causes include trauma (burns, cuts, contusions, crush injuries), autoimmune diseases, and organ rejection episodes.

By "enhance" or "promote," or "increase" or "expand" refers generally to the ability of a composition contemplated herein to produce, elicit, or cause a greater physiological response (i.e., downstream effects) compared to the response caused by either vehicle or a control molecule/composition. A measurable physiological response may include an increase in T cell expansion, activation, proliferation, and/or an increase in cancer cell death killing ability, among others apparent from the understanding in the art and the description herein. An "increased" or "enhanced" amount is typically a "statistically significant" amount, and may include an increase that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7, 1.8, etc.) the response produced by vehicle or a control composition.

By "decrease" or "lower," or "lessen," or "reduce," or "abate" refers generally to the ability of composition contemplated herein to produce, elicit, or cause a lesser physiological response (i.e., downstream effects) compared to the response caused by either vehicle or a control molecule/composition. A "decrease" or "reduced" amount is typically a "statistically significant" amount, and may include an decrease that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7, 1.8, etc.) the response (reference response) produced by vehicle, a control composition, or the response in a particular cell lineage.

By "maintain," or "preserve," or "maintenance," or "no change," or "no substantial change," or "no substantial decrease" refers generally to the ability of a composition contemplated herein to produce, elicit, or cause a lesser physiological response (i.e., downstream effects) in a cell, as compared to the response caused by either vehicle, a control molecule/composition, or the response in a particular cell lineage. A comparable response is one that is not significantly different or measurable different from the reference response.

The terms "specific binding affinity" or "specifically binds" or "specifically bound" or "specific binding" or "specifically targets" as used herein, describe binding of one molecule to another at greater binding affinity than background binding. A binding domain (or a CAR comprising a binding domain or a fusion protein containing a binding domain) "specifically binds" to a target molecule if it binds to or associates with a target molecule with an affinity or $K_a$ (i.e., an equilibrium association constant of a particular binding interaction with units of 1/M) of, for example, greater than or equal to about $10^5$ $M^{-1}$. In certain embodiments, a binding domain (or a fusion protein thereof) binds to a target with a Ka greater than or equal to about $10^6$ $M^{-1}$, $10^7$ $M^{-1}$, $10^8$ $M^{-1}$, $10^9$ $M^{-1}$, $10^{10}$ $M^{-1}$, $10^{11}$ $M^{-1}$, $10^{12}$ $M^{-1}$, or $10^{13}$ $M^{-1}$. "High affinity" binding domains (or single chain fusion proteins thereof) refers to those binding domains with a $K_a$ of at least $10^7$ $M^{-1}$, at least $10^8$ $M^{-1}$, at least $10^9$ $M^{-1}$, at least $10^{10}$ $M^{-1}$, at least $10^{11}$ $M^{-1}$, at least $10^{12}$ $M^{-1}$, at least $10^{13}$ $M^{-1}$, or greater.

Alternatively, affinity may be defined as an equilibrium dissociation constant ($K_d$) of a particular binding interaction with units of M (e.g., $10^{-5}$ M to $10^{-13}$ M, or less). Affinities of binding domain polypeptides and CAR proteins according to the present disclosure can be readily determined using conventional techniques, e.g., by competitive ELISA (enzyme-linked immunosorbent assay), or by binding association, or displacement assays using labeled ligands, or using a surface-plasmon resonance device such as the Biacore T100, which is available from Biacore, Inc., Piscataway, NJ, or optical biosensor technology such as the EPIC system or EnSpire that are available from Corning and Perkin Elmer respectively (see also, e.g., Scatchard et al. (1949) Ann. N.Y. Acad. Sci. 51:660; and U.S. Pat. Nos. 5,283,173; 5,468,614, or the equivalent).

In one embodiment, the affinity of specific binding is about 2 times greater than background binding, about 5 times greater than background binding, about 10 times greater than background binding, about 20 times greater than background binding, about 50 times greater than background binding, about 100 times greater than background binding, or about 1000 times greater than background binding or more.

An "antigen (Ag)" refers to a compound, composition, or substance that can stimulate the production of antibodies or a T cell response in an animal, including compositions (such as one that includes a tumor-specific protein) that are injected or absorbed into an animal. An antigen reacts with the products of specific humoral or cellular immunity, including those induced by heterologous antigens, such as the disclosed antigens. A "target antigen" or "target antigen or interest" is an antigen that a binding domain of a CAR or engineered TCR contemplated herein, is designed to bind.

An "epitope" or "antigenic determinant" refers to the region of an antigen to which a binding agent binds.

An "isolated peptide" or an "isolated polypeptide" and the like, as used herein, refer to in vitro isolation, synthesis, and/or purification of a recombinant or synthetic peptide or polypeptide molecule or of a non-naturally occurring peptide or polypeptide from a cellular environment, and from association with other components of the cell, i.e., it is not significantly associated with in vivo substances.

As used herein, "isolated polynucleotide" refers to in vitro isolation, synthesis, and/or purification of a recombinant, synthetic, or non-naturally occurring polynucleotide, e.g., an isolated complementary DNA (cDNA) or other polynucleotide that does not exist in nature and that has been made by the hand of man. In particular embodiments, an isolated polynucleotide refers to a recombinant, synthetic, or non-naturally occurring polynucleotide that has been purified from the sequences which flank it in a naturally-occurring state, e.g., a DNA fragment that has been removed from the sequences that are normally adjacent to the fragment.

Preferably, the cellular therapeutics manufactured using the methods contemplated herein are endotoxin free, and manufactured according to cGMP practices. As used herein, the term "endotoxin free" refers to vessels and/or compositions that contain at most trace amounts (i.e., amounts having no adverse physiological effects to a subject) of endotoxin, and preferably undetectable amounts of endotoxin. In one embodiment, the term "endotoxin free" refers to compositions that are at least 95%, at least 96%, at least 97%, at least 98%, at least 99%, or 100% endotoxin free. Endotoxins are toxins associated with certain bacteria, typically gram-negative bacteria, although endotoxins may be found in gram-positive bacteria, such as *Listeria monocytogenes*. The most prevalent endotoxins are lipopolysaccharides (LPS) or lipooligosaccharides (LOS) found in the outer membrane of various Gram-negative bacteria, and which represent a central pathogenic feature in the ability of these bacteria to cause disease. Small amounts of endotoxin in humans can produce fever, a lowering of the blood pressure, and activation of inflammation and coagulation, among other adverse physiological effects. Therefore, it is often desirable to remove most or all traces of endotoxin from drug product containers, because even small amounts may cause adverse effects in humans. Endotoxins can be removed from vessels using methods known in the art, for example, vessels can be cleaned in HEPA filtered washing equipment with endotoxin-free water, depyrogenated at 250° C., and clean-packaged in HEPA filtered workstations located inside a class 100/10 clean room (e.g., a class 100 clean room, contains no more than 100 particles bigger than half a micron in a cubic foot of air).

As used herein, the term "current good manufacturing practice (cGMP)" refers to the control and management of manufacturing, and quality control testing, of foods, pharmaceutical products, and medical devices. cGMP does not necessarily rely on sampling, but instead relies on documentation of every aspect of the process, activities, and operations involved with drug and medical device manufacture. If the documentation showing how the product was made and tested (which enables traceability and, in the event of future problems, recall from the market) is not correct and in order, then the product does not meet the required specification and is considered contaminated (i.e., adulterated in the US). Additionally, cGMP typically requires that all manufacturing and testing equipment has been qualified as suitable for use, and that all operational methodologies and procedures (e.g., manufacturing, cleaning, and analytical testing) utilized in the drug manufacturing process have been validated according to predetermined specifications to demonstrate that they can perform their purported function(s). In the US, the phrase "current good manufacturing practice" appears in 501(B) of the 1938 Food, Drug, and Cosmetic Act (21 U.S.C. § 351).

C. T Cell Manufacturing Methods

Currently, existing T cell manufacturing methods include various complex steps for the isolation, activation, transduction and expansion of CAR T cells. In contrast, the present inventors used a small-scale research model to develop a simple, robust, well characterized, flexible, closed system T cell manufacturing platform that was transferred to large-scale clinical cGMP manufacturing process for engineered CAR T cells.

In various embodiments, cells are manufactured using a closed processing system, or in in combination with a closed cell processing system. Closed cell processing systems automate processes including treatment, centrifugation, incubation, media addition, cell selection, cell washing, and final fill and finish within "closed" or resealable vessels. Closed cell processing systems integrate and automate the processes and replicate many qualitatively controlled manual tasks to provide consistent and operator-independent quality.

The benefits associated with an automated, closed-cell processing system would include significant reduction in the cost of therapies (typically 25-90%) and the number of operators required (typically >70%); lowered dependence on skilled labor; significant savings in capital investment through better facility use (typically 30-50%); improved quality and fewer quality events; and an ability to more rapidly scale up and scale out to match market demands.

In various embodiments, a method for manufacturing therapeutic T cell compositions comprises obtaining a population of cells comprising immune effector cells and antigen presenting cells using a closed system process. In certain embodiments, the isolated population of cells is seeded at a particular density to initiate cultures and T cells are activated and stimulated by contacting the cells with primary and costimulatory ligands. In particular embodiments, populations of cells comprising activated T cells are transduced with a viral vector encoding a CAR or engineered TCR and cultured to expand the T cells. Manufactured immune effector cell compositions comprising the therapeutic T cells may then be used to treat subjects in need thereof or frozen for later use.

1. Source of T Cells

In particular embodiments, T cells can be obtained from a number of sources including, but not limited to, peripheral blood, peripheral blood mononuclear cells, bone marrow, lymph nodes tissue, cord blood, thymus issue, tissue from a site of infection, ascites, pleural effusion, spleen tissue, and tumors. In one embodiment, T cells may also be obtained from a cultured T cell line, e.g., Jurkat, SupT 1, etc. In particular embodiments, a population of cells comprising T cells, e.g., PBMCs, is used in the manufacturing methods contemplated herein. In other embodiments, an isolated or purified population of T cells is used in the manufacturing methods contemplated herein.

In one embodiment, sources of T cells may also be obtained commercially, e.g., Sanguine Biosciences.

2. Harvesting Cells

The present invention contemplates the manufacture of improved T cell compositions. Cells may be autologous/autogeneic ("self") or non-autologous ("non-self," e.g., allogeneic, syngeneic or xenogeneic). In one embodiment, the cells are obtained from a mammalian subject. In another embodiment, the cells are obtained from a primate subject. In a particular embodiment, the cells are obtained from a human subject.

In various embodiments, cell populations comprising T cells are obtained from an individual and subjected to the manufacturing methods contemplated herein. In one embodiment, cells from the circulating blood of an individual are obtained by a method of apheresis, e.g., leukapheresis. The apheresis product may contain lymphocytes, including T cells, monocytes, granulocytes, B cells, other nucleated white blood cells, red blood cells, and platelets or may be a leukapheresis product comprising lymphocytes, including T cells, monocytes, granulocytes, B cells, and other nucleated white blood cells. In one embodiment, the cells collected by apheresis may be washed to remove the plasma fraction and to place the cells in an appropriate buffer or media for subsequent processing. The cells can be washed with PBS or with another suitable solution that lacks calcium, magnesium, and most, if not all other, divalent cations.

Once a population of cells comprising T cells has been obtained, cell counts and viability of cells within the population of cells can be determined, the population or portions thereof may be cryopreserved for future use or analyses, and cells in the population, e.g., PBMCs, may be characterized using a number of cell marker panels, e.g., CD3, CD4, CD8, CD14, CD16, CD19, CD28, CD45RA, CD45RO, CD61, CD62L, CD66b, CD127, and HLA-DR.

In particular embodiments, the volume of apheresed cells used in the manufacturing methods contemplated herein is about 50 mL to about 500 mL, about 50 mL to about 250 mL, about 50 mL to about 200 mL, about 100 mL to about 500 mL, about 100 mL to about 250 mL, or about 100 mL to about 200 mL, or any intervening range thereof.

In certain embodiments, the volume of apheresed cells used in the manufacturing methods contemplated herein is about 25 mL, about 50 mL, about 75 mL, about 100 mL, about 125 mL, about 150 mL, about 175 mL, about 200 mL, about 225 mL, about 250 mL, about 275 mL, about 300 mL, about 325 mL, about 350 mL, about 375 mL, about 400 mL, about 425 mL, about 450 mL, about 475 mL, or about 500 mL, or any intervening volume thereof.

3. PBMC Isolation

In particular embodiments, a population of PBMCs is used in the T cell manufacturing methods contemplated herein. In certain embodiments, PBMCs comprising T cells can be obtained from a unit of blood or apheresed fraction collected from a subject using any number of techniques known to the skilled person, such as centrifugation and sedimentation, e.g., FICOLL™ separation, PERCOLL™ separation, etc.

In certain embodiments, the PBMCs collected by apheresis are isolated in a FICOLL™ or PERCOLL™ gradient using a semiautomated flowthrough centrifuge, e.g., the Cobe 2991 cell processor, the Cell Saver 5 or the like. In some embodiments, the PBMCs collected by apheresis are isolated without the use of FICOLL™ or PERCOLL™ gradient using a counter-flow centrifugal elutriation device, e.g., Terumo BCT ELUTRA®, or the like. Use of the Cell Saver 5 allows for closed system processing of PBMC starting material via Ficoll as well as final concentration and washing of the manufactured T cell compositions on one device. Use of the closed system simplifies manufacturing by minimizing the equipment needed for cGMP processing and results in consistent and reproducibly pure PBMC or final T cell compositions.

In one embodiment, PBMCs are isolated using an ELUTRA® counter-flow centrifugal elutriation device and washed in a Cell Saver 5+ or LOVO.

In some embodiments, after isolation of PBMC, both cytotoxic and helper T lymphocytes can be sorted into naïve, memory, and effector T cell subpopulations either before or after activation, expansion, and/or genetic modification, using a closed system device and cGMP reagents, e.g., CliniMACS.

After isolation, PBMC cell counts and viability can be determined, PBMCs or portions thereof can be cryopreserved for future use or analyses, and PBMCs can be characterized using a number of cell marker panels, e.g., CD3, CD4, CD8, CD11b, CD11c, CD14, CD16, CD19, CD45RA, CD45RO, CD61, and CD66b.

In particular embodiments, after PBMCs are isolated, they are subject to one or more wash steps, e.g., to remove the Ficoll. In certain embodiments, cells may be washed one or more times before, during, or after, any number of the manufacturing steps contemplated herein. Washing may be performed in any suitable buffer or culture media, e.g., CliniMACS buffer supplemented with HABS or HSA, PlasmaLyte, TCGM, PBS, Ringer's solution, physiological saline, 0.9% NaCl, or another suitable solution that lacks calcium, magnesium, and most, if not all other, divalent cations, or any suitable culture media, or any suitable combination thereof. In one embodiment, after PBMCs are isolated, they are washed in a semiautomated flowthrough centrifuge, e.g., the Cobe 2991 cell processor, the Cell Saver 5, the Baxter CytoMate, LOVO or the like. In another embodiment, after PBMCs are isolated they are transferred to another sterile vessel, e.g., a transfer or culture vessel. As used herein, the term "vessel" relates generally to any container capable of being used for purposes of culturing, handling, manipulating, storing, analyzing, incubating, administering and otherwise establishing, supporting, growing, harvesting, treating, and using cells and by-products thereof ex vivo or in vitro or otherwise for a variety of purposes as set forth and as contemplated herein.

"Transfer vessels" generally refer to vessels that are not gas-permeable. In one embodiment, washes are performed in transfer vessels and subsequent cell manipulation are performed in one or more types of cell culture vessels.

Illustrative examples of cell culture vessels include, but are not limited to cell culture bags, bioreactors (e.g., Gas-permeable Rapid Expansion Flask (G-Rex) bioreactor, Wilson-Wolf Manufacturing; and WAVE bioreactors, GE Healthcare Life Sciences), cell or tissue culture devices, pouches, capsules, culture vials, apparatuses, cell factories, containers, culture tubes (e.g., microcentrifuge tubes, EPPENDORF TUBES®, FALCON® conical tubes, etc.), culture dishes (e.g., Petri dishes), culture flasks, spinner flasks, roller bottles, multi-well plates (e.g., 2-well, 4-well, 6-well, 12-well, 24-well, 48 well, 96-well, and 384-well plates), micro-incubators, micro-carriers, microplates, microslide and chamber slides.

In yet another embodiment, PBMCs may be washed one or more times in a semiautomated flowthrough centrifuge and transferred and washed one or more times in a suitable vessel.

Illustrative embodiments of cell culture bags include, but are not limited to MACS® GMP Cell Expansion Bags, MACS® GMP Cell Differentiation Bags, EXP-Pak™ Cell Expansion Bio-Containers, VueLife™ bags, KryoSure™ bags, KryoVue™ bags, Lifecell® bags, PermaLife™ bags, X-Fold™ bags, Si-Culture™ bags, Origen biomedical cryobags, and VectraCell™ bags. In particular embodiments, cell culture bags comprise one or more of the following characteristics: gas permeability (materials have suitable gas transfer rates for oxygen, carbon dioxide and nitrogen); negligible water loss rates (materials are practically impermeable to water); chemically and biologically inert (materials do not react with the vessel contents), and retention of flexibility and strength in various conditions (materials enable vessel to be microwaved, treated with UV irradiation, centrifuged, or used within a broad range of temperatures, e.g., from $-100°$ C. to $+100°$ C.).

Exemplary volumes of the cell culture vessel contemplated herein include, without limitation, volumes of about 10 mL, about 25 mL, about 50 mL, about 75 mL, about 100 mL, about 150 mL, about 250 mL, about 500 mL, about 750 mL, about 1000 mL, about 1250 mL, about 1500 mL, about 1750 mL, about 2000 mL, or more, including any intervening volume. For example, intervening volumes between 10 mL and 25 mL, include 11 mL, 12 mL, 13 mL, 14 mL, 15 mL, 16 mL, 17 mL, 18 mL, 19 mL, 20 mL, 21 mL, 22 mL, 23 mL, and 24 mL. In one embodiment, the volume of the cell culture vessel is about 100 mL to about 10 L.

Subsequent to washing the isolated cells, post-wash cells counts and viability can be determined, can be cryopreserved for future use or analyses, and/or can be characterized using fluorescence activated cell sorting (FACS) analysis, using a number of cell markers, e.g., CD3, CD4, CD8, CD27, CD28, CD45RA, CD45RO, CD62L, CD127, CD197, CD279, and HLA-DR.

4. Cryopreservation

In particular embodiments, the T cell manufacturing methods contemplated herein are practiced using freshly isolated populations of cells comprising T cells. In other particular embodiments, the methods contemplated herein are practiced using cryopreserved populations of cells comprising T cells. Cells may be cryopreserved following harvest or isolation of PBMCs, after culture initiation and activation, after transduction, or after expansion or after any process step. Manufactured T cell compositions may also be cryopreserved following the T cell manufacturing process. The freeze-thaw cycle may provide a more uniform T cell composition by removing non-T cell populations.

Cell populations may be cryopreserved in a suitable cell culture vessel as contemplated herein, see supra, under PBMC isolation and elsewhere herein. The cell populations may be frozen in a suitable cell culture medium and/or freezing medium, e.g., 50% plasmalyte and 50% Cryostor 10; 50/40/10 (XVIVO/HABS/DMSO); Cryostor 10; PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A. Cells then are frozen to a temperature of about −80° C. to about −135° C. at a rate of 1 per minute in a controlled rate freezer and stored in the vapor phase of a liquid nitrogen storage tank. Other illustrative methods of controlled freezing may be used as well as uncontrolled freezing immediately at −20° C. or in liquid nitrogen.

After cryopreservation, cells are thawed in a 37° C. water bath and washed in a suitable cell culture media or buffer, e.g., TCGM. The thawed cells may be subsequently used, either for the manufacturing methods contemplated herein or for administration to a subject. Wash steps may be performed as contemplated elsewhere herein.

In certain embodiments, the populations of cells comprising T cells are isolated from an individual and activated and stimulated to proliferate in vitro without further manipulation ex vivo or in vitro. Such cells can then be directly re-administered into the individual. In further embodiments, after a population of cells comprising T cells has been isolated, the cells are first activated and stimulated to proliferate in vitro prior to being genetically modified to express an engineered TCR or CAR. In this regard, the T cells may be cultured before and/or after being genetically modified (i.e., transduced or transfected to express an engineered TCR or CAR contemplated herein).

5. Culture Initiation and Activation

In order to achieve sufficient therapeutic doses of T cell compositions, existing methods for manufacturing T cells are often subject to one or more rounds of stimulation, activation and/or expansion, thereby introducing more opportunities for contamination, increasing the expense and time of the manufacturing process, and generally result in an inferior cell therapy product.

The T cell manufacturing methods contemplated herein simple and robust culture initiation and activation steps that contribute to a resulting T cell composition that is a superior therapeutic product. In one embodiment, culture initiation and activation comprises seeding cell populations in a cell culture vessel, e.g., cell culture bag, GREX bioreactor, WAVE bioreactor, etc. and activating T cells through primary and co-stimulatory T cell signaling pathways. The cellular compositions may further be cultured in the presence of one or more additional growth factors or cytokines, e.g., IL-2, IL7, and/or IL-15, or any suitable combination thereof.

In particular embodiments, culture initiation comprises seeding a population of cells comprising T cells, e.g., PBMCs, in a cell culture vessel, at a desired density, e.g., $1$-$5 \times 10^6$ cells/mL in a suitable cell culture medium containing one or more cytokines, primary stimulatory ligands, and co-stimulatory ligands. In another embodiment, the cytokines, stimulatory, and co-stimulatory ligands may be subsequently added to the PBMCs in the cell culture medium.

In one embodiment, the cell culture vessel is a cell culture bag, including but not limited MACS® GMP Cell Expansion Bags, MACS® GMP Cell Differentiation Bags, EXP-Pak™ Cell Expansion Bio-Containers, VueLife™ bags, KryoSure™ bags, KryoVue™ bags, Lifecell® bags, PermaLife™ bags, X-Fold™ bags, Si-Culture™ bags, and VectraCell™ bags, as contemplated elsewhere herein.

In particular embodiments, the cell culture vessel is seeded with a total of about $1 \times 10^9$ cells, about $5 \times 10^8$ cells, about $1 \times 10^8$ cells, about $5 \times 10^7$ cells, about $1 \times 10^7$ cells, about $5 \times 10^6$ cells, or about $1 \times 10^6$ cells, or any intervening amount of cells. In particular embodiments, the cells are PBMCs and are seeded at a total of about $1 \times 10^8$ cells.

In certain embodiments, cell populations, e.g., PBMCs, are seeded in the cell culture vessel at a density of about $1 \times 10^7$ cells/mL, about $9 \times 10^6$ cells/mL, about $8 \times 10^6$ cells/mL, about $7 \times 10^6$ cells/mL, about $6 \times 10^6$ cells/mL, about $5 \times 10^6$ cells/mL, about $4 \times 10^6$ cells/mL, about $3 \times 10^6$ cells/mL, about $2 \times 10^6$ cells/mL, about $1 \times 10^6$ cells/mL, about $9 \times 10^5$ cells/mL, about $8 \times 10^5$ cells/mL, about $7 \times 10^5$ cells/mL, about $6 \times 10^5$ cells/mL, about $5 \times 10^5$ cells/mL, about $4 \times 10^5$ cells/mL, about $3 \times 10^5$ cells/mL, about $2 \times 10^5$ cells/mL, or about $1 \times 10^5$ cells/mL, or any intervening density of cells. In particular embodiments, PBMCs are seeded at a density of about $1 \times 10^6$ cells/mL.

In particular embodiments, the cells are seeded in a cell culture vessel comprising a suitable cell culture medium. Illustrative examples of suitable cell culture media include, but are not limited to T cell growth medium (TCGM; X-VIVO™15 supplemented with 2 mM GlutaMAX™-I, 10 mM HEPES, and 5% human AB serum), CTS™ OpTmizer™ T Cell Expansion SFM (Life Technologies), CTS™ AIM V® Medium (Life Technologies), RPMI 1640, Clicks, DMEM, MEM, a-MEM, F-12, X-Vivo 15 (Lonza), CellGro® Serum-Free Medium (CellGenix), and X-Vivo 20 (Lonza) with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. In a particualr embodiment, the cell culture medium is TCGM.

Cell culture media contemplated herein may further comprise one or more factors including, but not limited to serum (e.g., fetal bovine or human serum), interleukin-2 (IL-2), insulin, IFN-γ, IL-4, IL-7, IL-21, GM-CSF, IL-10, IL-12, IL-15, TGFβ, and TNF-α.

In one embodiment, the cell culture medium may comprise one or more cytokines, e.g., such as IL-2, IL-7, and/or IL-15, or any suitable combination thereof. Illustrative examples of suitable concentrations of each cytokine or the total concentration of cytokines includes about 25 IU/mL, about 50 IU/mL, about 75 IU/mL, about 100 IU/mL, about 125 IU/mL, about 150 IU/mL, about 175 IU/mL, about 200 IU/mL, about 250 IU/mL, about 300 IU/mL, about 350 IU/mL, about 400 IU/mL, about 450 IU/mL, or about 500 IU/mL or any intervening amount of cytokine thereof. In particular embodiments, the cell culture medium comprises about 100 IU/mL of each of, or in total of, IL-2, IL-1, and/or IL-15, or any combination thereof.

In particular embodiments, the cell culture medium comprises about 250 IU/mL of each of, or in total of, IL-2, IL-1, and/or IL-15, or any combination thereof.

In particular embodiments, PBMCs or isolated T cells are contacted with one or more stimulatory agents and costimulatory agents, such as anti-CD3 and anti-CD28 antibodies, and one or more cytokines, such as IL-2, IL-7, and/or IL-15.

T cell activation can be accomplished by providing a primary stimulation signal through the T cell TCR/CD3 complex or via stimulation of the CD2 surface protein and by providing a secondary costimulation signal through an accessory molecule, e.g, CD28 or 4-1BBL The TCR/CD3 complex may be stimulated by contacting the T cell with a suitable CD3 binding agent, e.g., a CD3 ligand or an anti-CD3 monoclonal antibody. Illustrative examples of CD3 antibodies include, but are not limited to, OKT3, G19-4, BC3, and 64.1. Other antibodies which bind to the same epitopes as any of the above described antibodies can also be used. Additional antibodies, or combinations of antibodies, can be prepared and identified by standard techniques as disclosed elsewhere herein. In one embodiment, the anti-CD3 antibody is OKT3.

In another embodiment, a CD2 binding agent may be used to provide a primary stimulation signal to the T cells. Illustrative examples of CD2 binding agents include, but are not limited to, CD2 ligands and anti-CD2 antibodies, e.g., the T11.3 antibody in combination with the T11.1 or T11.2 antibody (Meuer, S. C. et al. (1984) *Cell* 36:897-906) and the 9.6 antibody (which recognizes the same epitope as TI 1.1) in combination with the 9-1 antibody (Yang, S. Y. et al. (1986) *J. Immunol.* 137:1097-1100).

In addition to the primary stimulation signal provided through the TCR/CD3 complex, or via CD2, induction of T cell responses requires a second, costimulatory signal. In particular embodiments, a CD28 binding agent can be used to provide a costimulatory signal. Suitable costimulatory ligands include, but are not limited to, CD7, B7-1 (CD80), B7-2 (CD86), PD-L1, PD-L2, 4-1BBL, OX40L, inducible costimulatory ligand (ICOS-L), intercellular adhesion molecule (ICAM), CD30L, CD40, CD70, CD83, HLA-G, MICA, MICB, HVEM, lymphotoxin beta receptor, ILT3, ILT4, an agonist or antibody that binds Toll ligand receptor, and a ligand that specifically binds with B7-H3.

In a particular embodiment, a costimulatory ligand comprises an antibody or antigen binding fragment thereof that specifically binds to a costimulatory molecule present on a T cell, including but not limited to, CD27, CD28, 4-IBB, OX40, CD30, CD40, PD-1, 1COS, lymphocyte function-associated antigen-1 (LFA-1), CD7, LIGHT, NKG2C, B7-H3, and a ligand that specifically binds with CD83.

Illustrative examples of CD28 binding agents include but are not limited to: natural CD28 ligands, e.g., a natural ligand for CD28 (e.g., a member of the B7 family of proteins, such as B7-1(CD80) and B7-2 (CD86); and anti-CD28 monoclonal antibody or fragment thereof capable of crosslinking the CD28 molecule, e.g., monoclonal antibodies 9.3, B-T3, XR-CD28, KOLT-2, 15E8, 248.23.2, and EX5.3D10. In one embodiment, the anti-CD28 antibody is 15E8.

In one embodiment, the molecule providing the primary stimulation signal, for example a molecule which provides stimulation through the TCR/CD3 complex or CD2, and the costimulatory molecule are coupled to the same surface.

In certain embodiments, binding agents that provide stimulatory and costimulatory signals are localized on the surface of a cell. This can be accomplished by transfecting or transducing a cell with a nucleic acid encoding the binding agent in a form suitable for its expression on the cell surface or alternatively by coupling a binding agent to the cell surface.

In another embodiment, the molecule providing the primary stimulation signal, for example a molecule which provides stimulation through the TCR/CD3 complex or CD2, and the costimulatory molecule are displayed on antigen presenting cells.

In one embodiment, the molecule providing the primary stimulation signal, for example a molecule which provides stimulation through the TCR/CD3 complex or CD2, and the costimulatory molecule are provided on separate surfaces.

In a certain embodiment, one of the binding agents that provide stimulatory and costimulatory signals is soluble (provided in solution) and the other agent(s) is provided on one or more surfaces.

In a particular embodiment, the binding agents that provide stimulatory and costimulatory signals are both provided in a soluble form (provided in solution).

In various embodiments, the methods for manufacturing T cells contemplated herein comprise activating T cells by contacting the T cells with soluble anti-CD3 and anti-CD28 antibodies.

In particular embodiments, the cell culture medium for activating T cells comprises a concentration of anti-CD3 antibody or CD3 binding agent of about 10 ng/mL, about 20 ng/mL, about 30 ng/mL, about 40 ng/mL, about 50 ng/mL, about 60 ng/mL, about 70 ng/mL, about 80 ng/mL, about 90 ng/mL, about 100 ng/mL, or about 200 ng/mL, or any intervening concentration.

In certain embodiments, the cell culture medium for activating T cells comprises a concentration of anti-CD28 antibody or CD28 binding agent of about 10 ng/mL, about 20 ng/mL, about 30 ng/mL, about 40 ng/mL, about 50 ng/mL, about 60 ng/mL, about 70 ng/mL, about 80 ng/mL, about 90 ng/mL, about 100 ng/mL, or about 200 ng/mL, or any intervening concentration.

In various embodiments, the cell culture medium for activating T cells comprises about 50 ng/mL of anti-CD3 antibody and 50 ng/mL of anti-CD28 antibody.

The populations of cells seeded in the cell culture vessel are activated for at least 30 minutes, at least 1 hour, at least 2 hours, at least 3 hours, at least 4 hours, a least 5 hours, at least 6 hours, at least 7 hours, at least 9 hours, at least 10 hours, at least 11 hours, at least 12 hours, at least 13 hours, at least 14 hours, at least 15 hours, at least 16 hours, at least 17 hours, at least 18 hours, at least 19 hours, at least 20 hours, at least 21 hours, at least 22 hours, at least 23 hours, or at least 24 hours, or any intervening length of time.

In certain embodiments, cells are harvested, isolated, and washed, cell cultures are initiated and T cells are activated all within a period of about 18 hours to about 36 hours, or within a period of about 24 hours, or any intervening length of time thereof.

6. Transduction

The T cell manufacturing methods contemplated herein comprise modifying immune effector cells and/or T cells to express an engineered T cell receptor (TCR) or chimeric antigen receptor (CAR). In particular embodiments, a population of cells comprising T cells is activated, modified to express an engineered TCR or CAR, and then cultured for expansion. The steps may take place in the same cell culture vessel or in different vessels. "Transduction" refers to the delivery of a gene(s) or other polynucleotide sequence, e.g., an engineered TCR or CAR to immune effector cells, including T cells, using a retroviral or lentiviral vector by means of viral infection. In one embodiment, retroviral vectors are transduced into a cell through infection and provirus integration. In certain embodiments, a target cell, e.g., a PBMC or a T cell, is "transduced" if it comprises a gene or other polynucleotide sequence delivered to the cell by infection using a viral or retroviral vector. In particular embodiments, a transduced cell comprises one or more genes or other polynucleotide sequences delivered by a retroviral or lentiviral vector in its cellular genome.

The production of infectious viral particles and viral stock solutions may be carried out using conventional techniques. Methods of preparing viral stock solutions are known in the art and are illustrated by, e.g., Y. Soneoka et al. (1995) *Nucl. Acids Res.* 23:628-633, and N. R. Landau et al. (1992) *J. Virol.* 66:5110-5113. Recombinant viruses with titers of several millions of transducing units per milliliter (TU/mL) can be generated by known techniques. After ultracentrifugation concentrated stocks of about $10^8$ TU/mL, $10^9$ TU/mL, $10^{10}$ TU/mL, $10^{11}$ TU/mL, or $10^{12}$ TU/mL, or any intervening titer can be obtained.

Viruses may be delivered according to viral titer (TU/mL), which can be measured, for example, by using a commercially available p24 titer assay, which is an ELISA against the p24 viral coat protein. The following formula can be used to calculate the pg/mL of p24: there are approximately 2000 molecules of p24 per physical particle (PP) of lentivirus: $(2\times10^3)\times(24\times10^3$ Da of p24 per PP), $48\times10^6$/Avogadro=$(48\times10^6)$ I $(6\times10^{23})$=$8\times10^{-17}$ g of p24 per PP, approximately 1 PP per $1\times10^{-16}$ g of p24, $1\times10^4$ PP per pg of p24. A reasonably well packaged, VSV-G pseudotyped lentiviral vector will have an infectivity index in the range of 1 TU per 1000 physical particles (PP) to 1 TU per 100 PP (or less). Thus, the range is approximately 10 to 100 TU/pg of p24. It is through this conversion that TU/mL is obtained.

Infectious titers may also be determined by analysis of transduced human osteosarcoma (HOS) cells (Kutner et al., 2009, Nature Protocols 4: 495-505). Briefly, transduced HOS cells are cultured for seven days in DMEM supplemented with 10% fetal bovine serum (FBS) after which the genomic DNA is extracted by DNeasy (Qiagen, Venlo Netherlands, Cat #69506) and evaluated by quantitative PCR (qPCR). The primer/probe sets of the qPCR protocol measures the vector copy number (VCN) of the transduced cells by determining the number of lentiviral psi-gag region copies per number of endogenous human RNaseP copies. The integrity of the provirus was assessed by sequencing individual proviral insertions.

In one embodiment, viral titer is determined using a HOS cell line assay.

In particular embodiments, a population of cells comprising activated T cells is transduced in a cell culture vessel about the time of activation, about 1 hour after activation, about 2 hours after activation, about 3 hours after activation, about 4 hours after activation, about 5 hours after activation, about 6 hours after activation, about 7 hours after activation, about 8 hours after activation, about 9 hours after activation, about 10 hours after activation, about 11 hours after activation, about 12 hours after activation, about 13 hours after activation, about 14 hours after activation, about 15 hours after activation, about 16 hours after activation, about 17 hours after activation, about 18 hours after activation, about 19 hours after activation, about 20 hours after activation, about 21 hours after activation, about 22 hours after activation, about 23 hours after activation, about 24 hours after activation, about 25 hours after activation, about 26 hours after activation, about 27 hours after activation, about 28 hours after activation, about 29 hours after activation, or about 30 hours after activation or any intervening period of time after activation.

In one embodiment, the population of cells is transduced about 20 to about 24 hours after activation.

The manufacturing methods contemplated herein comprise transducing PBMCs comprising activated T cells in a cell culture vessel with a vector of about $1\times10^8$ to about $1\times10^{10}$ TU/$10^8$ PBMCs, about $5\times10^8$ to about $5\times10^9$ TU/$10^8$ PBMCs, about $1\times10^9$ to about $5\times10^9$ TU/$10^8$ PBMCs, about $1\times1\times10^9$ to about $4\times10^9$ TU/$10^9$ PBMCs, about $1\times10^9$ to about $3\times10^9$ TU/$10^8$ PBMCs, about $1\times10^9$ to about $2\times10^9$ TU/$10^8$ PBMCs, or any intervening TU thereof.

In one embodiment, the manufacturing methods contemplated herein comprise transducing PBMCs comprising activated T cells in a cell culture vessel with a vector of about $1\times10^8$ TU/$10^8$ PBMCs, about $5\times10^8$ TU/$10^8$ PBMCs, about $6\times10^8$ TU/$10^8$ PBMCs, about $7\times10^8$ TU/$10^8$ PBMCs, about $8\times10^8$ TU/$10^8$ PBMCs, about $9\times10^8$ TU/$10^8$ PBMCs, about $1\times10^9$ TU/$10^8$ PBMCs, about $2\times10^9$ TU/$10^8$ PBMCs, about $3\times10^9$ TU/$10^8$ PBMCs, about $4\times10^9$ TU/$10^8$ PBMCs, about $5\times10^9$ TU/$10^8$ PBMCs, about $6\times10^9$ TU/$10^8$ PBMCs, about $7\times10^9$ TU/$10^8$ PBMCs, about $8\times10^9$ TU/$10^8$ PBMCs, about $9\times10^9$ TU/$10^8$ PBMCs, or about $1\times10^{10}$ TU/$10^8$ PBMCs, or any intervening TU.

In a particular embodiment, the cells are transduced with a vector of about $1\times10^7$ to about $2\times10^9$ TU/$10^8$ PBMCs.

In one embodiment, the manufacturing methods contemplated herein comprise transducing PBMCs comprising activated T cells in a cell culture vessel with a vector at an MOI of about 1, 5, 10, 15, 20, 25, 30, 35, 40, 45, 50, 55, 60, 65, 70, 75, 80, 85, 90, 95 or 100, or any intervening integer. In one embodiment, PBMCs are transduced with a vector at an MOI of about 20.

In certain embodiments, the vector may be diluted in cell culture medium up to about 10% of the cell culture volume, about 15% of the cell culture volume, about 16% of the cell culture volume, about 17% of the cell culture volume, about 18% of the cell culture volume, about 19% of the cell culture volume, about 20% of the cell culture volume, about 21% of the cell culture volume, about 22% of the cell culture volume, about 23% of the cell culture volume, about 24% of the cell culture volume, about 25% of the cell culture volume, about 30% of the cell culture volume, about 35% of the cell culture volume, about 40% of the cell culture volume, about 45% of the cell culture volume, or about 50% of the cell culture volume, or any intervening percent thereof.

In a particular embodiment, the vector is diluted in cell culture medium, e.g., TCGM, up to about 20% of the cell culture volume.

The populations of cells seeded in the cell culture vessel are transduced for about 6 hours, about 12 hours, about 18 hours, about 24 hours, about 30 hours, about 36 hours, about 42 hours, about 48 hours, about 54 hours, or about 60 hours, or any intervening length of time.

In a particular embodiment, the cells are transduced for about 48 hours.

After the cells are transduced they may be subjected to one or more wash steps as contemplated herein and subsequently seeded into a suitable cell culture vessel for expansion.

7. Expansion

The T cell manufacturing platforms contemplated herein may comprise one or more rounds of T cell expansion. In particular embodiments, populations of cells comprising T cells that have been activated and/or transduced are seeded into suitable cell culture vessels comprising cell culture medium suitable for expansion. In particular embodiments, cells are seeded into a bioreactor and are periodically harvested without reseeding.

In certain embodiments, cells are reseeded at a density to maintain log-phase growth of the cells.

In particular embodiments, the cells are seeded into the cell culture at a density of about $0.1\times10^6$ to about $1\times10^7$ cells/mL, about $0.1\times10^6$ to about $0.9\times10^6$ cells/mL, about $0.1\times10^6$ to about $0.8\times10^6$ cells/mL, about $0.1\times10^6$ to about $0.7\times10^6$ cells/mL, about $0.1\times10^6$ to about $0.6\times10^6$ cells/mL, about $0.1\times10^6$ to about $0.5\times10^6$ cells/mL, about $0.2\times10^6$ to about $0.5\times10^6$ cells/mL, or about $0.3\times10^6$ to about $0.5\times10^6$ cells/mL, or any intervening density of cells, so long as the cells remain in log-phase growth.

In certain embodiments, the cells are seeded into the cell culture at a density of about $0.1\times10^6$ cells/mL, about $0.2\times10^6$ cells/mL, about $0.3\times10^6$ cells/mL, about $0.4\times10^6$ cells/mL, about $0.5\times10^6$ cells/mL, about $0.6\times10^6$ cells/mL, about $0.7\times10^6$ cells/mL, about $0.8\times10^6$ cells/mL, about $0.9\times10^6$ cells/ mL, or about 1×10⁷ cells/mL, or any intervening density of cells, so long as the cells remain in log-phase growth.

In some embodiments, the cells are seeded into a bioreactor, e.g., WAVE bioreactor, at a density of about 0.1×10⁶ cells/mL, about 0.5×10⁶ cells/mL, about 1×10⁶ cells/mL, about 2×10⁶ cells/mL, about 3×10⁶ cells/mL, about 4×10⁶ cells/mL, about 5×10⁶ cells/mL, about 6×10⁶ cells/mL, about 7×10⁶ cells/mL, about 8×10⁶ cells/mL, about 9×10⁶ cells/mL, or about 1×10⁷ cells/mL or any intervening density of cells, so long as the cells remain in log-phase growth.

In particular embodiments, the cells are seeded in a cell culture vessel comprising a suitable cell culture medium for T cell expansion. Illustrative examples of suitable cell culture media for T cell expansion include, but are not limited to T cell growth medium (TCGM), CTS™ OpT-mizer™ T Cell Expansion SFM (Life Technologies), CTS™ AIM V® Medium (Life Technologies), RPMI 1640, Clicks, DMEM, MEM, a-MEM, F-12, X-Vivo 15 (Lonza), and X-Vivo 20 (Lonza) and/or additional hormones, growth factors, or cytokine(s) sufficient for the growth and expansion of T cells. In a particular embodiment, the cell culture medium is TCGM. In a certain embodiment, the cell culture media further comprises one or more factors including, but not limited to serum (e.g., fetal bovine or human serum), interleukin-2 (IL-2), insulin, IFN-γ, IL-4, IL-7, IL-21, GM-CSF, IL-10, IL-12, IL-15, TGFβ, and TNF-α, or any combination thereof.

In one embodiment, the cell culture medium may comprise one or more cytokines, e.g., such as IL-2, IL-7, and/or IL-15, or any suitable combination thereof. Illustrative examples of suitable concentrations of each cytokine or the total concentration of cytokines includes about 25 IU/mL, about 50 IU/mL, about 75 IU/mL, about 100 IU/mL, about 125 IU/mL, about 150 IU/mL, about 175 IU/mL, about 200 IU/mL, about 250 IU/mL, about 300 IU/mL, about 350 IU/mL, about 400 IU/mL, about 450 IU/mL, or about 500 IU/mL or any intervening amount of cytokine thereof. In particular embodiments, the cell culture medium comprises about 100 IU/mL of each of, or in total of, IL-2, IL-1, and/or IL-15, or any combination thereof.

In particular embodiments, the cell culture medium comprises about 250 IU/mL of each of, or in total of, IL-2, IL-1, and/or IL-15, or any combination thereof.

In particular embodiments, the T cell manufacturing methods contemplated herein comprise expanding T cells for about 3 days to about 14 days, about 3 days to about 13 days, about 3 days to about 12 days, about 3 days to about 11 days, about 3 days to about 10 days, about 3 days to about 9 days, about 3 days to about 8 days, or about 3 to about 7 days, or about 5 to about 8 days or any intervening number of days. In certain embodiments, the T cell manufacturing methods contemplated herein comprise expanding T cells for about 3 days, about 4 days, about 5 days, about 6 days, about 7 days, about 8 days, about 9 days, about 10 days, about 11 days, or about 12 days. The expansion may be performed in the same vessel and/or type of vessel for the entire expansion period or in different vessels and/or types of vessels for the expansion period.

In one embodiment, the T cell expansion is performed for about 5 days to about 8 days in a cell culture bag.

In one embodiment, the T cell expansion is performed for about 5 days to about 8 days in a cell culture bag and then expansion is continued in a bioreactor, including but not limited to, a WAVE or G-REX bioreactor. In a particular embodiment, expansion may be continued in the bioreactor for about 1 day, about 2 days, about 3 days, about 4 days, or about 5 days or more.

In another embodiment, the T cell expansion is performed for about 5 days to about 8 days in a bioreactor, including but not limited to, a WAVE bioreactor or G-REX bioreactor.

The WAVE bioreactor allows for varying rates of rocking and at a variety of different rocking angles. Illustrative rocking rates include, but are not limited to 1, 2, 3, 4, 5, 6, 7, 8, 9, 10, 11, 12, 13, 14, 15, 16, 17, 18, 19, or 20 rocks per minute. In certain embodiments, the methods of stimulation and expansion of the present invention provide for the angle of the rocking platform to be set at 1.5°, 2°, 2.5°, 3°, 3.5°, 4°, 4.5°, 5°, 5.5°, 6°, 6.5°, 7°, 7.5°, 8°, 8.5°, or 9.0°.

In one embodiment, the volume of the WAVE bioreactor is 2500 mL, the rocking rate is about 6 or about 7 rpm and the angle is between about 7 and about 8.

In one embodiment, cells are initially seeded in about 100 mL in a GREX bioreactor, and about 200 mL of fresh growth media is added to the culture at days 3, 4, and 5. In certain embodiments, additional media is added to the GREX bioreactor to bring the culture volume to about 1 L at day 7.

Cell counts and viability are checked daily or on any number of days, the cells or a portion of the cells may be cryopreserved, and/or cells may be characterized by FACs analysis for marker expression, e.g., CD3, CD4, CD8, CD28, CD45RA, CD45RO, CD62L, CD127, CD27, CD197 and HLA-DR, transgene.

In one embodiment, a population of T cells subjected to the manufacturing methods contemplated herein is expanded at least 50 fold, at least 100 fold, at least 200 fold, at least 300 fold, at least 400 fold, at least 500 fold, at least 600 fold, at least 700 fold, at least 800 fold, at least 900 fold, or at least 1000 fold, or more compared the starting population of T cells.

8. Recovery of Manufactured T Cell Compositions

In particular embodiments, methods for manufacturing T cells contemplated herein comprise a step of recovering the manufactured T cell compositions comprising harvesting and washing the expanded cells in using a semiautomated flowthrough centrifuge, e.g., the Cobe 2991 cell processor, the Cell Saver 5, the Baxter CytoMate, LOVO, or the like.

Prior to harvesting the expanded cells, pre-harvest sample aliquots may be taken to establish cell counts, viability, cell characterization, e.g., FACs analysis, purity, and/or other general release criteria for the cells. In addition, post-harvest sample aliquots may be taken to establish cell counts and/or viability.

The recovered T cell compositions are then transferred to one or more IV bags or other suitable vessels, e.g., MACS® GMP Cell Expansion Bags, MACS® GMP Cell Differentiation Bags, EXP-Pak™ Cell Expansion Bio-Containers, VueLife™ bags, KryoSure™ bags, KryoVue™ bags, Lifecell® bags, PermaLife™ bags, X-Fold™ bags, Si-Culture™ bags, Origen biomedical cryobags and VectraCell™ bags and cryopreserved in a controlled rate freezer as discussed supra and elsewhere herein, until the cells are ready for use. In particular embodiments, cells are frozen in 50% plasmalyte and 50% Cryostor 10; 50/40/10 (XVIVO/HABS/DMSO); or Cryostor 10.

Bags (10 to 250 mL capacity) containing therapeutic T cell compositions are stored in blood bank conditions in a monitored −80° C. to −135° C. Infusion bags are stored in the freezer until needed.

D. Engineered T Cell Receptors and Chimeric Antigen Receptors

The T cell manufacturing methods contemplated are particularly useful for expanding T cells modified to express high affinity T cell receptors (engineered TCRs) or chimeric antigen receptors (CARs) in a reliable and reproducible manner. In one embodiment, the T cell is genetically modified to express one ore more engineered TCRs or CARs. As used herein, T cells modified to express an engineered TCR or CAR contemplated herein may be referred to as, "antigen-specific redirected T cells."

1. Engineered TCRs

Naturally occurring T cell receptors comprise two subunits, an α-subunit and a 3-subunit, each of which is a unique protein produced by recombination event in each T cell's genome. Libraries of TCRs may be screened for their selectivity to particular target antigens. In this manner, natural TCRs, which have a high-avidity and reactivity toward target antigens may be selected, cloned, and subsequently introduced into a population of T cells used for adoptive immunotherapy.

In one embodiment, T cells are modified by introducing a polynucleotide encoding a subunit of a TCR that has the ability to form TCRs that confer specificity to T cells for tumor cells expressing a target antigen. In particular embodiments, the subunits have one or more amino acid substitutions, deletions, insertions, or modifications compared to the naturally occurring subunit, so long as the subunits retain the ability to form TCRs conferring upon transfected T cells the ability to home to target cells, and participate in immunologically-relevant cytokine signaling. The engineered TCRs preferably also bind target cells displaying the relevant tumor-associated peptide with high avidity, and optionally mediate efficient killing of target cells presenting the relevant peptide in vivo.

The nucleic acids encoding engineered TCRs are preferably isolated from their natural context in a (naturally-occurring) chromosome of a T cell, and can be incorporated into suitable vectors as described elsewhere herein. Both the nucleic acids and the vectors comprising them usefully can be transferred into a cell, which cell is preferably a T cell. The modified T cells are then able to express both chains of a TCR encoded by the transduced nucleic acid or nucleic acids. In preferred embodiments, the engineered TCR is an exogenous TCR because it is introduced into T cells that do not normally express the particular TCR. The essential aspect of the engineered TCRs is that it has high avidity for a tumor antigen presented by a major histocompatibility complex (MHC) or similar immunological component. In contrast to engineered TCRs, CARs are engineered to bind target antigens in an MHC independent manner.

The protein encoded by the inventive nucleic acids can be expressed with additional polypeptides attached to the amino-terminal or carboxyl-terminal portion of the inventive α-chain or β-chain of a TCR so long as the attached additional polypeptide does not interfere with the ability of the α-chain or β-chain to form a functional T cell receptor and the MHC dependent antigen recognition.

Antigens that are recognized by the engineered TCRs contemplated herein include, but are not limited to cancer antigens, including antigens on both hematological cancers and solid tumors. Illustrative antigens include, but are not limited to alpha folate receptor, 5T4, $α_vβ_6$ integrin, BCMA, B7-H3, B7-H6, CAIX, CD19, CD20, CD22, CD30, CD33, CD44, CD44v6, CD44v7/8, CD70, CD79a, CD79b, CD123, CD138, CD171, CEA, CSPG4, EGFR, EGFR family including ErbB2 (HER2), EGFRvIII, EGP2, EGP40, EPCAM, EphA2, EpCAM, FAP, fetal AchR, FRα, GD2, GD3, 'Glypican-3 (GPC3), HLA-A1+MAGE1, HLA-A2+MAGE1, HLA-A3+MAGE1, HLA-A1+NY-ESO-1, HLA-A2+NY-ESO-1, HLA-A3+NY-ESO-1, IL-11Rα, IL-13Rα2, Lambda, Lewis-Y, Kappa, Mesothelin, Muc1, Muc16, NCAM, NKG2D Ligands, NY-ESO-1, PRAME, PSCA, PSMA, ROR1, SSX, Survivin, TAG72, TEMs, and VEGFR2.

2. Chimeric Antigen Receptors (CARs)

The T cell manufacturing methods contemplated herein include modifying T cells to express one or more CARs as contemplated herein. In various embodiments, the present invention provides T cells genetically engineered with vectors designed to express CARs that redirect cytotoxicity toward tumor cells. CARs are molecules that combine antibody-based specificity for a target antigen (e.g., tumor antigen) with a T cell receptor-activating intracellular domain to generate a chimeric protein that exhibits a specific anti-tumor cellular immune activity. As used herein, the term, "chimeric," describes being composed of parts of different proteins or DNAs from different origins.

The CARs contemplated herein comprise an extracellular domain that binds to a specific target antigen (also referred to as a binding domain or antigen-specific binding domain), a transmembrane domain and an intracellular signaling domain. The main characteristic of CARs are their ability to redirect immune effector cell specificity, thereby triggering proliferation, cytokine production, phagocytosis or production of molecules that can mediate cell death of the target antigen expressing cell in a major histocompatibility (MHC) independent manner, exploiting the cell specific targeting abilities of monoclonal antibodies, soluble ligands or cell specific coreceptors.

In particular embodiments, a CAR comprises an extracellular binding domain including but not limited to an antibody or antigen binding fragment thereof, a tethered ligand, or the extracellular domain of a coreceptor, that specifically binds a target antigen that is a tumor-associated antigen (TAA) or a tumor-specific antigen (TSA). In certain embodiments, the TAA or TSA is expressed on a blood cancer cell. In another embodiment, the TAA or TSA is expressed on a cell of a solid tumor. In particular embodiments, the solid tumor is a glioblastoma, a non-small cell lung cancer, a lung cancer other than a non-small cell lung cancer, breast cancer, prostate cancer, pancreatic cancer, liver cancer, colon cancer, stomach cancer, a cancer of the spleen, skin cancer, a brain cancer other than a glioblastoma, a kidney cancer, a thyroid cancer, or the like.

In particular embodiments, the TAA or TSA is selected from the group consisting of alpha folate receptor, 5T4, $α_vβ_6$ integrin, BCMA, B7-H3, B7-H6, CAIX, CD19, CD20, CD22, CD30, CD33, CD44, CD44v6, CD44v7/8, CD70, CD79a, CD79b, CD123, CD138, CD171, CEA, CSPG4, EGFR, EGFR family including ErbB2 (HER2), EGFRvIII, EGP2, EGP40, EPCAM, EphA2, EpCAM, FAP, fetal AchR, FRα, GD2, GD3, 'Glypican-3 (GPC3), HLA-A1+MAGE1, HLA-A2+MAGE1, HLA-A3+MAGE1, HLA-A1+NY-ESO-1, HLA-A2+NY-ESO-1, HLA-A3+NY-ESO-1, IL-11Rα, IL-13Rα2, Lambda, Lewis-Y, Kappa, Mesothelin, Muc1, Muc16, NCAM, NKG2D Ligands, NY-ESO-1, PRAME, PSCA, PSMA, ROR1, SSX, Survivin, TAG72, TEMs, and VEGFR2.

a. Binding Domain

In particular embodiments, CARs contemplated herein comprise an extracellular binding domain that specifically binds to a target polypeptide, e.g, target antigen, expressed on tumor cell. As used herein, the terms, "binding domain," "extracellular domain," "extracellular binding domain," "antigen-specific binding domain," and "extracellular antigen specific binding domain," are used interchangeably and provide a CAR with the ability to specifically bind to the target antigen of interest. A binding domain may comprise any protein, polypeptide, oligopeptide, or peptide that possesses the ability to specifically recognize and bind to a biological molecule (e.g., a cell surface receptor or tumor protein, lipid, polysaccharide, or other cell surface target molecule, or component thereof). A binding domain includes any naturally occurring, synthetic, semi-synthetic, or recombinantly produced binding partner for a biological molecule of interest.

In particular embodiments, the extracellular binding domain of a CAR comprises an antibody or antigen binding fragment thereof. An "antibody" refers to a binding agent that is a polypeptide comprising at least a light chain or heavy chain immunoglobulin variable region which specifically recognizes and binds an epitope of a target antigen, such as a peptide, lipid, polysaccharide, or nucleic acid containing an antigenic determinant, such as those recognized by an immune cell. Antibodies include antigen binding fragments thereof. The term also includes genetically engineered forms such as chimeric antibodies (for example, humanized murine antibodies), heteroconjugate antibodies (such as, bispecific antibodies) and antigen binding fragments thereof. See also, Pierce Catalog and Handbook, 1994-1995 (Pierce Chemical Co., Rockford, IL); Kuby, *J., Immunology*, 3rd Ed., W. H. Freeman & Co., New York, 1997.

In particular embodiments, the target antigen is an epitope of an alpha folate receptor, 5T4, $\alpha_v\beta_6$ integrin, BCMA, B7-H3, B7-H6, CAIX, CD19, CD20, CD22, CD30, CD33, CD44, CD44v6, CD44v7/8, CD70, CD79a, CD79b, CD123, CD138, CD171, CEA, CSPG4, EGFR, EGFR family including ErbB2 (HER2), EGFRvIII, EGP2, EGP40, EPCAM, EphA2, EpCAM, FAP, fetal AchR, FRα, GD2, GD3, 'Glypican-3 (GPC3), HLA-A1+MAGE1, HLA-A2+MAGE1, HLA-A3+MAGE1, HLA-A1+NY-ESO-1, HLA-A2+NY-ESO-1, HLA-A3+NY-ESO-1, IL-11Rα, IL-13Rα2, Lambda, Lewis-Y, Kappa, Mesothelin, Muc1, Muc16, NCAM, NKG2D Ligands, NY-ESO-1, PRAME, PSCA, PSMA, ROR1, SSX, Survivin, TAG72, TEMs, or VEGFR2 polypeptide.

Light and heavy chain variable regions contain a "framework" region interrupted by three hypervariable regions, also called "complementarity-determining regions" or "CDRs." The CDRs can be defined or identified by conventional methods, such as by sequence according to Kabat et al (Wu, TT and Kabat, E. A., J Exp Med. 132(2):211-50, (1970); Borden, P. and Kabat E. A., PNAS, 84: 2440-2443 (1987); (see, Kabat et al., *Sequences of Proteins of Immunological Interest*, U.S. Department of Health and Human Services, 1991, which is hereby incorporated by reference), or by structure according to Chothia et al (Choithia, C. and Lesk, A. M., J Mol. Biol., 196(4): 901-917 (1987), Choithia, C. et al, Nature, 342: 877-883 (1989)).

The sequences of the framework regions of different light or heavy chains are relatively conserved within a species, such as humans. The framework region of an antibody, that is the combined framework regions of the constituent light and heavy chains, serves to position and align the CDRs in three-dimensional space. The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, the CDRs located in the variable domain of the heavy chain of the antibody are referred to as CDRH1, CDRH2, and CDRH3, whereas the CDRs located in the variable domain of the light chain of the antibody are referred to as CDRL1, CDRL2, and CDRL3. Antibodies with different specificities (i.e., different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs).

References to "$V_H$" or "VH" refer to the variable region of an immunoglobulin heavy chain, including that of an antibody, Fv, scFv, dsFv, Fab, or other antibody fragment as disclosed herein. References to "$V_L$" or "VL" refer to the variable region of an immunoglobulin light chain, including that of an antibody, Fv, scFv, dsFv, Fab, or other antibody fragment as disclosed herein.

A "monoclonal antibody" is an antibody produced by a single clone of B lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. Monoclonal antibodies include humanized monoclonal antibodies.

A "chimeric antibody" has framework residues from one species, such as human, and CDRs (which generally confer antigen binding) from another species, such as a mouse. In particular preferred embodiments, a CAR contemplated herein comprises antigen-specific binding domain that is a chimeric antibody or antigen binding fragment thereof.

In certain preferred embodiments, the antibody is a humanized antibody (such as a humanized monoclonal antibody) that specifically binds to a surface protein on a tumor cell. A "humanized" antibody is an immunoglobulin including a human framework region and one or more CDRs from a non-human (for example a mouse, rat, or synthetic) immunoglobulin. Humanized antibodies can be constructed by means of genetic engineering (see for example, U.S. Pat. No. 5,585,089).

In particular embodiments, the extracellular binding domain of a CAR comprises an antibody or antigen binding fragment thereof, including but not limited to a Camel Ig (a camelid antibody (VHH)), Ig NAR, Fab fragments, Fab' fragments, F(ab)'2 fragments, F(ab)'3 fragments, Fv, single chain Fv antibody ("scFv"), bis-scFv, (scFv)2, minibody, diabody, triabody, tetrabody, disulfide stabilized Fv protein ("dsFv"), and single-domain antibody (sdAb, Nanobody).

"Camel Ig" or "camelid VHH" as used herein refers to the smallest known antigen-binding unit of a heavy chain antibody (Koch-Nolte, et al, FASEB J., 21: 3490-3498 (2007)). A "heavy chain antibody" or a "camelid antibody" refers to an antibody that contains two VH domains and no light chains (Riechmann L. et al, J. Immunol. Methods 231:25-38 (1999); WO94/04678; WO94/25591; U.S. Pat. No. 6,005,079).

"IgNAR" of "immunoglobulin new antigen receptor" refers to class of antibodies from the shark immune repertoire that consist of homodimers of one variable new antigen receptor (VNAR) domain and five constant new antigen receptor (CNAR) domains.

Papain digestion of antibodies produces two identical antigen-binding fragments, called "Fab" fragments, each with a single antigen-binding site, and a residual "Fc" fragment, whose name reflects its ability to crystallize readily. The Fab fragment contains the heavy- and light-chain variable domains and also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other chemical couplings of antibody fragments are also known.

"Fv" is the minimum antibody fragment which contains a complete antigen-binding site. In a single-chain Fv (scFv) species, one heavy- and one light-chain variable domain can be covalently linked by a flexible peptide linker such that the light and heavy chains can associate in a "dimeric" structure analogous to that in a two-chain Fv species.

The term "diabodies" refers to antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies may be bivalent or bispecific. Diabodies are described more fully in, for example, EP 404,097; WO 1993/01161; Hudson et al., Nat. Med. 9:129-134 (2003); and Hollinger et al., PNAS USA 90: 6444-6448 (1993). Triabodies and tetrabodies are also described in Hudson et al., Nat. Med. 9:129-134 (2003).

"Single domain antibody" or "sdAb" or "nanobody" refers to an antibody fragment that consists of the variable region of an antibody heavy chain (VH domain) or the variable region of an antibody light chain (VL domain) (Holt, L., et al, Trends in Biotechnology, 21(11): 484-490).

"Single-chain Fv" or "scFv" antibody fragments comprise the VH and VL domains of antibody, wherein these domains are present in a single polypeptide chain and in either orientation (e.g., VL-VH or VH-VL). Generally, the scFv polypeptide further comprises a polypeptide linker between the VH and VL domains which enables the scFv to form the desired structure for antigen binding. For a review of scFv, see, e.g., Pluckthiin, in *The Pharmacology of Monoclonal Antibodies*, vol. 113, Rosenburg and Moore eds., (Springer-Verlag, New York, 1994), pp. 269-315.

In a certain embodiment, the scFv binds an alpha folate receptor, 5T4, $\alpha_v\beta_6$ integrin, BCMA, B7-H3, B7-H6, CAIX, CD19, CD20, CD22, CD30, CD33, CD44, CD44v6, CD44v7/8, CD70, CD79a, CD79b, CD123, CD138, CD171, CEA, CSPG4, EGFR, EGFR family including ErbB2 (HER2), EGFRvIII, EGP2, EGP40, EPCAM, EphA2, EpCAM, FAP, fetal AchR, FRα, GD2, GD3, 'Glypican-3 (GPC3), HLA-A1+MAGE1, HLA-A2+MAGE1, HLA-A3+MAGE1, HLA-A1+NY-ESO-1, HLA-A2+NY-ESO-1, HLA-A3+NY-ESO-1, IL-11Rα, IL-13Rα2, Lambda, Lewis-Y, Kappa, Mesothelin, Muc1, Muc16, NCAM, NKG2D Ligands, NY-ESO-1, PRAME, PSCA, PSMA, ROR1, SSX, Survivin, TAG72, TEMs, or VEGFR2 polypeptide.

b. Linkers

In certain embodiments, the CARs contemplated herein may comprise linker residues between the various domains, e.g., between $V_H$ and $V_L$ domains, added for appropriate spacing and conformation of the molecule. CARs contemplated herein, may comprise one, two, three, four, or five or more linkers. In particular embodiments, the length of a linker is about 1 to about 25 amino acids, about 5 to about 20 amino acids, or about 10 to about 20 amino acids, or any intervening length of amino acids. In some embodiments, the linker is 1, 2, 3, 4, 5, 6, 7, 8, 9, 10, 11, 12, 13, 14, 15, 16, 17, 18, 19, 20, 21, 22, 23, 24, 25, or more amino acids long.

Illustrative examples of linkers include glycine polymers $(G)_n$; glycine-serine polymers $(G_{1-5}S_{1-5})_n$, where n is an integer of at least one, two, three, four, or five; glycine-alanine polymers; alanine-serine polymers; and other flexible linkers known in the art. Glycine and glycine-serine polymers are relatively unstructured, and therefore may be able to serve as a neutral tether between domains of fusion proteins such as the CARs described herein. Glycine accesses significantly more phi-psi space than even alanine, and is much less restricted than residues with longer side chains (see Scheraga, *Rev. Computational Chem.* 11173-142 (1992)). The ordinarily skilled artisan will recognize that design of a CAR in particular embodiments can include linkers that are all or partially flexible, such that the linker can include a flexible linker as well as one or more portions that confer less flexible structure to provide for a desired CAR structure.

Other exemplary linkers include, but are not limited to the following amino acid sequences: GGG; DGGGS (SEQ ID NO: 1); TGEKP (SEQ ID NO: 2) (see, e.g., Liu et al., PNAS 5525-5530 (1997)); GGRR (SEQ ID NO: 3) (Pomerantz et al. 1995, supra); (GGGGS)$_n$ wherein=1, 2, 3, 4 or 5 (SEQ ID NO: 4) (Kim et al., PNAS 93, 1156-1160 (1996.); EGKSSGSGSESKVD (SEQ ID NO:5) (Chaudhary et al., 1990, Proc. Natl. Acad. Sci. U.S.A. 87:1066-1070); KESGSVSSEQLAQFRSLD (SEQ ID NO:6) (Bird et al., 1988, Science 242:423-426), GGRRGGGS (SEQ ID NO:7); LRQRDGERP (SEQ ID NO:8); LRQKDGGGSERP (SEQ ID NO:9); LRQKd(GGGS)$_2$ ERP (SEQ ID NO:10). Alternatively, flexible linkers can be rationally designed using a computer program capable of modeling both DNA-binding sites and the peptides themselves (Desjarlais & Berg, PNAS 90:2256-2260 (1993), PNAS 91:11099-11103 (1994) or by phage display methods.

In particular embodiments a CAR comprises a scFV that further comprises a variable region linking sequence. A "variable region linking sequence," is an amino acid sequence that connects a heavy chain variable region to a light chain variable region and provides a spacer function compatible with interaction of the two sub-binding domains so that the resulting polypeptide retains a specific binding affinity to the same target molecule as an antibody that comprises the same light and heavy chain variable regions. In one embodiment, the variable region linking sequence is 1, 2, 3, 4, 5, 6, 7, 8, 9, 10, 11, 12, 13, 14, 15, 16, 17, 18, 19, 20, 21, 22, 23, 24, 25, or more amino acids long. In a particular embodiment, the variable region linking sequence comprises a glycine-serine polymer $(G_{1-5}S_{1-5})_n$, where n is an integer of at least 1, 2, 3, 4, or 5. In another embodiment, the variable region linking sequence comprises a $(G_4S)_3$ amino acid linker.

c. Spacer Domain

In particular embodiments, the binding domain of the CAR is followed by one or more "spacer domains," which refers to the region that moves the antigen binding domain away from the effector cell surface to enable proper cell/cell contact, antigen binding and activation (Patel et al., *Gene Therapy*, 1999; 6: 412-419). The spacer domain may be derived either from a natural, synthetic, semi-synthetic, or recombinant source. In certain embodiments, a spacer domain is a portion of an immunoglobulin, including, but not limited to, one or more heavy chain constant regions, e.g., CH2 and CH3. The spacer domain can include the amino acid sequence of a naturally occurring immunoglobulin hinge region or an altered immunoglobulin hinge region.

In one embodiment, the spacer domain comprises the CH2 and CH3 of IgG1.

d. Hinge Domain

The binding domain of the CAR is generally followed by one or more "hinge domains," which plays a role in positioning the antigen binding domain away from the effector cell surface to enable proper cell/cell contact, antigen binding and activation. A CAR generally comprises one or more hinge domains between the binding domain and the transmembrane Domain™. The hinge domain may be derived either from a natural, synthetic, semi-synthetic, or recombinant source. The hinge domain can include the amino acid sequence of a naturally occurring immunoglobulin hinge region or an altered immunoglobulin hinge region.

Illustrative hinge domains suitable for use in the CARs described herein include the hinge region derived from the extracellular regions of type 1 membrane proteins such as CD8α, CD4, CD28 and CD7, which may be wild-type hinge regions from these molecules or may be altered. In another embodiment, the hinge domain comprises a CD8α hinge region.

e. Transmembrane™ Domain

The "transmembrane domain" is the portion of the CAR that fuses the extracellular binding portion and intracellular signaling domain and anchors the CAR to the plasma membrane of the immune effector cell. The TM domain may be derived either from a natural, synthetic, semi-synthetic, or recombinant source.

Illustrative™ domains may be derived from (i.e., comprise at least the transmembrane region(s) of) the alpha, beta or zeta chain of the T-cell receptor, CD3 epsilon, CD3 zeta, CD4, CD5, CD9, CD16, CD22, CD27, CD28, CD33, CD37, CD45, CD64, CD80, CD86, CD134, CD137, and CD154.

In one embodiment, the CARs contemplated herein comprise a TM domain derived from CD8α. In another embodiment, a CAR contemplated herein comprises a TM domain derived from CD8α and a short oligo- or polypeptide linker, preferably between 1, 2, 3, 4, 5, 6, 7, 8, 9, or 10 amino acids in length that links the TM domain and the intracellular signaling domain of the CAR. A glycine-serine linker provides a particularly suitable linker.

f. Intracellular Signaling Domain

In particular embodiments, CARs contemplated herein comprise an intracellular signaling domain. An "intracellular signaling domain," refers to the part of a CAR that participates in transducing the message of effective CAR binding to a target antigen into the interior of the immune effector cell to elicit effector cell function, e.g., activation, cytokine production, proliferation and cytotoxic activity, including the release of cytotoxic factors to the CAR-bound target cell, or other cellular responses elicited with antigen binding to the extracellular CAR domain.

The term "effector function" refers to a specialized function of the cell. Effector function of the T cell, for example, may be cytolytic activity or help or activity including the secretion of a cytokine. Thus, the term "intracellular signaling domain" refers to the portion of a protein which transduces the effector function signal and that directs the cell to perform a specialized function. While usually the entire intracellular signaling domain can be employed, in many cases it is not necessary to use the entire domain. To the extent that a truncated portion of an intracellular signaling domain is used, such truncated portion may be used in place of the entire domain as long as it transduces the effector function signal. The term intracellular signaling domain is meant to include any truncated portion of the intracellular signaling domain sufficient to transducing effector function signal.

It is known that signals generated through the TCR alone are insufficient for full activation of the T cell and that a secondary or costimulatory signal is also required. Thus, T cell activation can be said to be mediated by two distinct classes of intracellular signaling domains: primary signaling domains that initiate antigen-dependent primary activation through the TCR (e.g., a TCR/CD3 complex) and costimulatory signaling domains that act in an antigen-independent manner to provide a secondary or costimulatory signal. In preferred embodiments, a CAR contemplated herein comprises an intracellular signaling domain that comprises one or more "costimulatory signaling domain" and a "primary signaling domain."

Primary signaling domains regulate primary activation of the TCR complex either in a stimulatory way, or in an inhibitory way. Primary signaling domains that act in a stimulatory manner may contain signaling motifs which are known as immunoreceptor tyrosine-based activation motifs or ITAMs.

Illustrative examples of ITAM containing primary signaling domains that are of particular use in the invention include those derived from TCRζ, FcRγ, FcRPβ, CD3γ, CD3δ, CD3ε, CD3ζ, CD22, CD79a, CD79b, and CD66d. In particular preferred embodiments, a CAR comprises a CD3ζ primary signaling domain and one or more costimulatory signaling domains. The intracellular primary signaling and costimulatory signaling domains may be linked in any order in tandem to the carboxyl terminus of the transmembrane domain.

CARs contemplated herein comprise one or more costimulatory signaling domains to enhance the efficacy and expansion of T cells expressing CAR receptors. As used herein, the term, "costimulatory signaling domain," or "costimulatory domain", refers to an intracellular signaling domain of a costimulatory molecule.

Illustrative examples of such costimulatory molecules include CD27, CD28, 4-1BB (CD137), OX40 (CD134), CD30, CD40, PD-1, ICOS (CD278), CTLA4, LFA-1, CD2, CD7, LIGHT, TRIM, LCK3, SLAM, DAP10, LAG3, HVEM and NKD2C, and CD83. In one embodiment, a CAR comprises one or more costimulatory signaling domains selected from the group consisting of CD28, CD137, and CD134, and a CD3 primary signaling domain.

In one embodiment, a CAR comprises an scFv that binds an alpha folate receptor, 5T4, $α_vβ_6$ integrin, BCMA, B7-H3, B7-H6, CAIX, CD19, CD20, CD22, CD30, CD33, CD44, CD44v6, CD44v7/8, CD70, CD79a, CD79b, CD123, CD138, CD171, CEA, CSPG4, EGFR, EGFR family including ErbB2 (HER2), EGFRvIII, EGP2, EGP40, EPCAM, EphA2, EpCAM, FAP, fetal AchR, FRα, GD2, GD3, 'Glypican-3 (GPC3), HLA-A1+MAGE1, HLA-A2+MAGE1, HLA-A3+MAGE1, HLA-A1+NY-ESO-1, HLA-A2+NY-ESO-1, HLA-A3+NY-ESO-1, IL-11Rα, IL-13Rα2, Lambda, Lewis-Y, Kappa, Mesothelin, Muc1, Muc16, NCAM, NKG2D Ligands, NY-ESO-1, PRAME, PSCA, PSMA, ROR1, SSX, Survivin, TAG72, TEMs, or VEGFR2 polypeptide; a transmembrane domain derived from a polypeptide selected from the group consisting of: CD8α; CD4, CD45, PD1, and CD152; and one or more intracellular costimulatory signaling domains selected from the group consisting of: CD28, CD54, CD134, CD137, CD152, CD273, CD274, and CD278; and a CD3 primary signaling domain.

In another embodiment, a CAR comprises an scFv that binds an alpha folate receptor, 5T4, $\alpha_v\beta_6$ integrin, BCMA, B7-H3, B7-H6, CAIX, CD19, CD20, CD22, CD30, CD33, CD44, CD44v6, CD44v7/8, CD70, CD79a, CD79b, CD123, CD138, CD171, CEA, CSPG4, EGFR, EGFR family including ErbB2 (HER2), EGFRvIII, EGP2, EGP40, EPCAM, EphA2, EpCAM, FAP, fetal AchR, FRα, GD2, GD3, 'Glypican-3 (GPC3), HLA-A1+MAGE1, HLA-A2+MAGE1, HLA-A3+MAGE1, HLA-A1+NY-ESO-1, HLA-A2+NY-ESO-1, HLA-A3+NY-ESO-1, IL-11Rα, IL-13Rα2, Lambda, Lewis-Y, Kappa, Mesothelin, Muc1, Muc16, NCAM, NKG2D Ligands, NY-ESO-1, PRAME, PSCA, PSMA, ROR1, SSX, Survivin, TAG72, TEMs, or VEGFR2 polypeptide; a hinge domain selected from the group consisting of: IgG1 hinge/CH2/CH3 and CD8α, and CD8α; a transmembrane domain derived from a polypeptide selected from the group consisting of: CD8α; CD4, CD45, PD1, and CD152; and one or more intracellular costimulatory signaling domains selected from the group consisting of: CD28, CD134, and CD137; and a CD3 primary signaling domain.

In yet another embodiment, a CAR comprises an scFv, further comprising a linker, that binds an alpha folate receptor, 5T4, $\alpha_v\beta_6$ integrin, BCMA, B7-H3, B7-H6, CAIX, CD19, CD20, CD22, CD30, CD33, CD44, CD44v6, CD44v7/8, CD70, CD79a, CD79b, CD123, CD138, CD171, CEA, CSPG4, EGFR, EGFR family including ErbB2 (HER2), EGFRvIII, EGP2, EGP40, EPCAM, EphA2, EpCAM, FAP, fetal AchR, FRα, GD2, GD3, 'Glypican-3 (GPC3), HLA-A1+MAGE1, HLA-A2+MAGE1, HLA-A3+MAGE1, HLA-A1+NY-ESO-1, HLA-A2+NY-ESO-1, HLA-A3+NY-ESO-1, IL-11Rα, IL-13Rα2, Lambda, Lewis-Y, Kappa, Mesothelin, Muc1, Muc16, NCAM, NKG2D Ligands, NY-ESO-1, PRAME, PSCA, PSMA, ROR1, SSX, Survivin, TAG72, TEMs, or VEGFR2 polypeptide; a hinge domain selected from the group consisting of: IgG1 hinge/CH2/CH3 and CD8α, and CD8α; a transmembrane domain comprising a TM domain derived from a polypeptide selected from the group consisting of: CD8α; CD4, CD45, PD1, and CD152, and a short oligo- or polypeptide linker, preferably between 1, 2, 3, 4, 5, 6, 7, 8, 9, or 10 amino acids in length that links the TM domain to the intracellular signaling domain of the CAR; and one or more intracellular costimulatory signaling domains selected from the group consisting of: CD28, CD134, and CD137; and a CD3 primary signaling domain.

In a particular embodiment, a CAR comprises an scFv that binds an alpha folate receptor, 5T4, $\alpha_v\beta_6$ integrin, BCMA, B7-H3, B7-H6, CAIX, CD19, CD20, CD22, CD30, CD33, CD44, CD44v6, CD44v7/8, CD70, CD79a, CD79b, CD123, CD138, CD171, CEA, CSPG4, EGFR, EGFR family including ErbB2 (HER2), EGFRvIII, EGP2, EGP40, EPCAM, EphA2, EpCAM, FAP, fetal AchR, FRα, GD2, GD3, 'Glypican-3 (GPC3), HLA-A1+MAGE1, HLA-A2+MAGE1, HLA-A3+MAGE1, HLA-A1+NY-ESO-1, HLA-A2+NY-ESO-1, HLA-A3+NY-ESO-1, IL-11Rα, IL-13Rα2, Lambda, Lewis-Y, Kappa, Mesothelin, Muc1, Muc16, NCAM, NKG2D Ligands, NY-ESO-1, PRAME, PSCA, PSMA, ROR1, SSX, Survivin, TAG72, TEMs, or VEGFR2 polypeptide; a hinge domain comprising a CD8α polypeptide; a CD8α transmembrane domain comprising a polypeptide linker of about 3 amino acids; one or more intracellular costimulatory signaling domains selected from the group consisting of: CD28, CD134, and CD137; and a CD3ζ primary signaling domain.

E. Polypeptides

The present invention contemplates, in part, engineered TCR and CAR polypeptides and fragments thereof, cells and compositions comprising the same, and vectors that express polypeptides. "Polypeptide," "polypeptide fragment," "peptide" and "protein" are used interchangeably, and refer to a recombinant, synthetic, or non-natural amino acid polymer. Polypeptides are not limited to a specific length, e.g., they may comprise a full length protein sequence or a fragment of a full length protein, and may include post-translational modifications of the polypeptide, for example, glycosylations, acetylations, phosphorylations and the like, as well as other modifications known in the art, both naturally occurring and non-naturally occurring. In various embodiments, the polypeptides contemplated herein comprise a signal (or leader) sequence at the N-terminal end of the protein, which cotranslationally or post-translationally directs transfer of the protein. Illustrative examples of suitable signal sequences useful in disclosed herein include, but are not limited to the IgG1 heavy chain signal polypeptide, a CD8α signal polypeptide, or a human GM-CSF receptor alpha signal polypeptide. Polypeptides can be prepared using any of a variety of well known recombinant and/or synthetic techniques. Polypeptides contemplated herein specifically encompass the CARs of the present disclosure, or sequences that have deletions from, additions to, and/or substitutions of one or more amino acid of a polypeptide as contemplated herein.

Polypeptides include "polypeptide variants." Polypeptide variants may differ from a naturally occurring polypeptide in one or more substitutions, deletions, additions and/or insertions. Such variants may be naturally occurring or may be synthetically generated, for example, by modifying one or more of the above polypeptide sequences. For example, in particular embodiments, it may be desirable to improve the binding affinity and/or other biological properties of the engineered TCRs or CARs by introducing one or more substitutions, deletions, additions and/or insertions. Preferably, polypeptides of the invention include polypeptides having at least about 65%, 70%, 75%, 85%, 90%, 95%, 98%, or 99% amino acid identity thereto.

Polypeptides include "polypeptide fragments." Polypeptide fragments refer to a polypeptide, which can be monomeric or multimeric, that has an amino-terminal deletion, a carboxyl-terminal deletion, and/or an internal deletion or substitution of a naturally-occurring or recombinantly-produced polypeptide. In certain embodiments, a polypeptide fragment can comprise an amino acid chain at least 5 to about 500 amino acids long. It will be appreciated that in certain embodiments, fragments are at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 150, 200, 250, 300, 350, 400, or 450 amino acids long.

The polypeptide may also be fused in-frame or conjugated to a linker or other sequence for ease of synthesis, purification or identification of the polypeptide (e.g., poly-His), or to enhance binding of the polypeptide to a solid support.

As noted above, polypeptides contemplated herein may be altered in various ways including amino acid substitutions, deletions, truncations, and insertions. Methods for such manipulations are generally known in the art. For example, amino acid sequence variants of a reference polypeptide can be prepared by mutations in the DNA. Methods for mutagenesis and nucleotide sequence alterations are well known in the art. See, for example, Kunkel (1985, *Proc. Natl. Acad. Sci. USA.* 82: 488-492), Kunkel et al., (1987, *Methods in Enzymol,* 154: 367-382), U.S. Pat. No. 4,873, 192, Watson, J. D. et al., (*Molecular Biology of the Gene,*

Fourth Edition, Benjamin/Cummings, Menlo Park, Calif., 1987) and the references cited therein. Guidance as to appropriate amino acid substitutions that do not affect biological activity of the protein of interest may be found in the model of Dayhoff et al., (1978) *Atlas of Protein Sequence and Structure* (Natl. Biomed. Res. Found., Washington, D.C.).

In certain embodiments, a variant will contain conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Modifications may be made in the structure of the polynucleotides and polypeptides of the present invention and still obtain a functional molecule that encodes a variant or derivative polypeptide with desirable characteristics.

Polypeptide variants further include glycosylated forms, aggregative conjugates with other molecules, and covalent conjugates with unrelated chemical moieties (e.g., pegylated molecules). Covalent variants can be prepared by linking functionalities to groups which are found in the amino acid chain or at the N- or C-terminal residue, as is known in the art. Variants also include allelic variants, species variants, and muteins. Truncations or deletions of regions which do not affect functional activity of the proteins are also variants.

In one embodiment, where expression of two or more polypeptides is desired, the polynucleotide sequences encoding them can be separated by and IRES sequence as discussed elsewhere herein. In another embodiment, two or more polypeptides can be expressed as a fusion protein that comprises one or more self-cleaving polypeptide sequences.

Polypeptides of the present invention include fusion polypeptides. In preferred embodiments, fusion polypeptides and polynucleotides encoding fusion polypeptides are provided. Fusion polypeptides and fusion proteins refer to a polypeptide having at least two, three, four, five, six, seven, eight, nine, or ten or more polypeptide segments. Fusion polypeptides are typically linked C-terminus to N-terminus, although they can also be linked C-terminus to C-terminus, N-terminus to N-terminus, or N-terminus to C-terminus. The polypeptides of the fusion protein can be in any order or a specified order. Fusion polypeptides or fusion proteins can also include conservatively modified variants, polymorphic variants, alleles, mutants, subsequences, and interspecies homologs, so long as the desired transcriptional activity of the fusion polypeptide is preserved. Fusion polypeptides may be produced by chemical synthetic methods or by chemical linkage between the two moieties or may generally be prepared using other standard techniques. Ligated DNA sequences comprising the fusion polypeptide are operably linked to suitable transcriptional or translational control elements as discussed elsewhere herein.

In one embodiment, a fusion partner comprises a sequence that assists in expressing the protein (an expression enhancer) at higher yields than the native recombinant protein. Other fusion partners may be selected so as to increase the solubility of the protein or to enable the protein to be targeted to desired intracellular compartments or to facilitate transport of the fusion protein through the cell membrane.

Fusion polypeptides may further comprise a polypeptide cleavage signal between each of the polypeptide domains described herein. In addition, polypeptide site can be put into any linker peptide sequence. Exemplary polypeptide cleavage signals include polypeptide cleavage recognition sites such as protease cleavage sites, nuclease cleavage sites (e.g., rare restriction enzyme recognition sites, self-cleaving ribozyme recognition sites), and self-cleaving viral oligopeptides (see deFelipe and Ryan, 2004. *Traffic,* 5(8); 616-26).

Suitable protease cleavages sites and self-cleaving peptides are known to the skilled person (see, e.g., in Ryan et al., 1997. *J. Gener. Virol.* 78, 699-722; Scymczak et al. (2004) Nature Biotech. 5, 589-594). Exemplary protease cleavage sites include, but are not limited to the cleavage sites of potyvirus NIa proteases (e.g., tobacco etch virus protease), potyvirus HC proteases, potyvirus P1 (P35) proteases, byovirus NIa proteases, byovirus RNA-2-encoded proteases, aphthovirus L proteases, enterovirus 2A proteases, rhinovirus 2A proteases, picoma 3C proteases, comovirus 24K proteases, nepovirus 24K proteases, RTSV (rice tungro spherical virus) 3C-like protease, PYVF (parsnip yellow fleck virus) 3C-like protease, heparin, thrombin, factor Xa and enterokinase. Due to its high cleavage stringency, TEV (tobacco etch virus) protease cleavage sites are preferred in one embodiment, e.g., EXXYXQ(G/S) (SEQ ID NO:11), for example, ENLYFQG (SEQ ID NO:12) and ENLYFQS (SEQ ID NO:13), wherein X represents any amino acid (cleavage by TEV occurs between Q and G or Q and S).

In a particular embodiment, self-cleaving peptides include those polypeptide sequences obtained from potyvirus and cardiovirus 2A peptides, FMDV (foot-and-mouth disease virus), equine rhinitis A virus, Thosea asigna virus and porcine teschovirus.

In certain embodiments, the self-cleaving polypeptide site comprises a 2A or 2A-like site, sequence or domain (Donnelly et al., 2001. *J. Gen. Virol.* 82:1027-1041).

F. Polynucleotides

In particular embodiments, polynucleotides encoding one or more engineered TCR or CAR polypeptides contemplated herein are provided. As used herein, the terms "polynucleotide" or "nucleic acid" refers to messenger RNA (mRNA), RNA, genomic RNA (gRNA), plus strand RNA (RNA(+)), minus strand RNA (RNA(-)), genomic DNA (gDNA), complementary DNA (cDNA), recombinant DNA, synthetic DNA, or non-naturally occurring DNA. Polynucleotides include single and double stranded polynucleotides. Preferably, polynucleotides of the invention include polynucleotides or variants having at least about 50%, 55%, 60%, 65%, 70%, 75%, 80%, 85%, 90%, 95%, 96%, 97%, 98%, 99% or 100% sequence identity to any of the reference sequences described herein (see, e.g., Sequence Listing), typically where the variant maintains at least one biological activity of the reference sequence. In various illustrative embodiments, the present invention contemplates, in part, polynucleotides comprising expression vectors, viral vectors, and transfer plasmids, and compositions, and cells comprising the same.

In particular embodiments, polynucleotides are provided by this invention that encode at least about 5, 10, 25, 50, 100, 150, 200, 250, 300, 350, 400, 500, 1000, 1250, 1500, 1750, or 2000 or more contiguous amino acid residues of a polypeptide of the invention, as well as all intermediate lengths. It will be readily understood that "intermediate lengths," in this context, means any length between the quoted values, such as 6, 7, 8, 9, etc., 101, 102, 103, etc.; 151, 152, 153, etc.; 201, 202, 203, etc.

As used herein, the terms "polynucleotide variant" and "variant" and the like refer to polynucleotides displaying substantial sequence identity with a reference polynucleotide sequence or polynucleotides that hybridize with a reference sequence under stringent conditions that are defined hereinafter. These terms include polynucleotides in which one or more nucleotides have been added or deleted, or replaced with different nucleotides compared to a reference polynucleotide. In this regard, it is well understood in the art that certain alterations inclusive of mutations, additions, deletions and substitutions can be made to a reference polynucleotide whereby the altered polynucleotide retains the biological function or activity of the reference polynucleotide.

The recitations "sequence identity" or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. Included are nucleotides and polypeptides having at least about 50%, 55%, 60%, 65%, 70%, 75%, 80%, 85%, 90%, 95%, 96%, 97%, 98%, 99% or 100% sequence identity to any of the reference sequences described herein, typically where the polypeptide variant maintains at least one biological activity of the reference polypeptide.

Terms used to describe sequence relationships between two or more polynucleotides or polypeptides include "reference sequence," "comparison window," "sequence identity," "percentage of sequence identity," and "substantial identity". A "reference sequence" is at least 12 but frequently 15 to 18 and often at least 25 monomer units, inclusive of nucleotides and amino acid residues, in length. Because two polynucleotides may each comprise (1) a sequence (i.e., only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, WI, USA) or by inspection and the best alignment (i.e., resulting in the highest percentage homology over the comparison window) generated by any of the various methods selected. Reference also may be made to the BLAST family of programs as for example disclosed by Altschul et al., 1997, Nucl. Acids Res. 25:3389. A detailed discussion of sequence analysis can be found in Unit 19.3 of Ausubel et al., Current Protocols in Molecular Biology, John Wiley & Sons Inc, 1994-1998, Chapter 15.

The polynucleotides of the present invention, regardless of the length of the coding sequence itself, may be combined with other DNA sequences, such as promoters and/or enhancers, untranslated regions (UTRs), Kozak sequences, polyadenylation signals, additional restriction enzyme sites, multiple cloning sites, internal ribosomal entry sites (IRES), recombinase recognition sites (e.g., LoxP, FRT, and Att sites), termination codons, transcriptional termination signals, and polynucleotides encoding self-cleaving polypeptides, epitope tags, as disclosed elsewhere herein or as known in the art, such that their overall length may vary considerably. It is therefore contemplated that a polynucleotide fragment of almost any length may be employed, with the total length preferably being limited by the ease of preparation and use in the intended recombinant DNA protocol.

Polynucleotides can be prepared, manipulated and/or expressed using any of a variety of well established techniques known and available in the art. In order to express a desired polypeptide, a nucleotide sequence encoding the polypeptide, can be inserted into appropriate vector. Examples of vectors are plasmid, autonomously replicating sequences, and transposable elements. Additional exemplary vectors include, without limitation, plasmids, phagemids, cosmids, artificial chromosomes such as yeast artificial chromosome (YAC), bacterial artificial chromosome (BAC), or P1-derived artificial chromosome (PAC), bacteriophages such as lambda phage or M13 phage, and animal viruses. Examples of categories of animal viruses useful as vectors include, without limitation, retrovirus (including lentivirus), adenovirus, adeno-associated virus, herpesvirus (e.g., herpes simplex virus), poxvirus, baculovirus, papillomavirus, and papovavirus (e.g., SV40). Examples of expression vectors are pClneo vectors (Promega) for expression in mammalian cells; pLenti4/V5-DEST™, pLenti6/V5-DEST™, and pLenti6.2/V5-GW/lacZ (Invitrogen) for lentivirus-mediated gene transfer and expression in mammalian cells. In particular embodiments, he coding sequences of the chimeric proteins disclosed herein can be ligated into such expression vectors for the expression of the chimeric protein in mammalian cells.

The "control elements" or "regulatory sequences" present in an expression vector are those non-translated regions of the vector-origin of replication, selection cassettes, promoters, enhancers, translation initiation signals (Shine Dalgarno sequence or Kozak sequence) introns, a polyadenylation sequence, 5' and 3' untranslated regions-which interact with host cellular proteins to carry out transcription and translation. Such elements may vary in their strength and specificity. Depending on the vector system and host utilized, any number of suitable transcription and translation elements, including ubiquitous promoters and inducible promoters may be used.

In particular embodiments, a vector for use in practicing the invention including, but not limited to expression vectors and viral vectors, will include exogenous, endogenous, or heterologous control sequences such as promoters and/or enhancers. An "endogenous" control sequence is one which is naturally linked with a given gene in the genome. An "exogenous" control sequence is one which is placed in juxtaposition to a gene by means of genetic manipulation (i.e., molecular biological techniques) such that transcription of that gene is directed by the linked enhancer/promoter. A "heterologous" control sequence is an exogenous sequence that is from a different species than the cell being genetically manipulated.

The term "promoter" as used herein refers to a recognition site of a polynucleotide (DNA or RNA) to which an RNA polymerase binds. An RNA polymerase initiates and transcribes polynucleotides operably linked to the promoter. In particular embodiments, promoters operative in mammalian cells comprise an AT-rich region located approximately 25 to 30 bases upstream from the site where transcription is initiated and/or another sequence found 70 to 80 bases upstream from the start of transcription, a CNCAAT region where N may be any nucleotide.

The term "enhancer" refers to a segment of DNA which contains sequences capable of providing enhanced transcription and in some instances can function independent of their orientation relative to another control sequence. An enhancer can function cooperatively or additively with promoters and/or other enhancer elements. The term "promoter/enhancer" refers to a segment of DNA which contains sequences capable of providing both promoter and enhancer functions.

The term "operably linked", refers to a juxtaposition wherein the components described are in a relationship permitting them to function in their intended manner. In one embodiment, the term refers to a functional linkage between a nucleic acid expression control sequence (such as a promoter, and/or enhancer) and a second polynucleotide sequence, e.g., a polynucleotide-of-interest, wherein the expression control sequence directs transcription of the nucleic acid corresponding to the second sequence.

As used herein, the term "constitutive expression control sequence" refers to a promoter, enhancer, or promoter/enhancer that continually or continuously allows for transcription of an operably linked sequence. A constitutive expression control sequence may be a "ubiquitous" promoter, enhancer, or promoter/enhancer that allows expression in a wide variety of cell and tissue types or a "cell specific," "cell type specific," "cell lineage specific," or "tissue specific" promoter, enhancer, or promoter/enhancer that allows expression in a restricted variety of cell and tissue types, respectively.

Illustrative ubiquitous expression control sequences suitable for use in particular embodiments of the invention include, but are not limited to, a cytomegalovirus (CMV) immediate early promoter, a viral simian virus 40 (SV40) (e.g., early or late), a Moloney murine leukemia virus (MoMLV) LTR promoter, a Rous sarcoma virus (RSV) LTR, a herpes simplex virus (HSV) (thymidine kinase) promoter, H5, P7.5, and P11 promoters from vaccinia virus, an elongation factor 1-alpha (EF1a) promoter, early growth response 1 (EGR1), ferritin H (FerH), ferritin L (FerL), Glyceraldehyde 3-phosphate dehydrogenase (GAPDH), eukaryotic translation initiation factor 4A1 (EIF4A1), heat shock 70 kDa protein 5 (HSPA5), heat shock protein 90 kDa beta, member 1 (HSP90B1), heat shock protein 70 kDa (HSP70), β-kinesin (β-KIN), the human ROSA 26 locus (Irions et al., Nature Biotechnology 25, 1477-1482 (2007)), a Ubiquitin C promoter (UBC), a phosphoglycerate kinase-1 (PGK) promoter, a cytomegalovirus enhancer/chicken β-actin (CAG) promoter, a β-actin promoter and a myeloproliferative sarcoma virus enhancer, negative control region deleted, d1587rev primer-binding site substituted (MND) promoter (Challita et al., J Virol. 69(2):748-55 (1995)).

In a particular embodiment, it may be desirable to express a polynucleotide comprising an engineered TCR or CAR from a promoter that provides stable and long-term expression in T cells and at sufficient levels to redirect the T cells to cells expressing the target antigen. In a preferred embodiment, the promoter is an EFla promoter or an MND promoter.

As used herein, "conditional expression" may refer to any type of conditional expression including, but not limited to, inducible expression; repressible expression; expression in cells or tissues having a particular physiological, biological, or disease state, etc. This definition is not intended to exclude cell type or tissue specific expression. Certain embodiments of the invention provide conditional expression of a polynucleotide-of-interest, e.g., expression is controlled by subjecting a cell, tissue, organism, etc., to a treatment or condition that causes the polynucleotide to be expressed or that causes an increase or decrease in expression of the polynucleotide encoded by the polynucleotide-of-interest.

Illustrative examples of inducible promoters/systems include, but are not limited to, steroid-inducible promoters such as promoters for genes encoding glucocorticoid or estrogen receptors (inducible by treatment with the corresponding hormone), metallothionine promoter (inducible by treatment with various heavy metals), MX-1 promoter (inducible by interferon), the "GeneSwitch" mifepristone-regulatable system (Sirin et al., 2003, Gene, 323:67), the cumate inducible gene switch (WO 2002/088346), tetracycline-dependent regulatory systems, etc.

Conditional expression can also be achieved by using a site specific DNA recombinase. According to certain embodiments of the invention the vector comprises at least one (typically two) site(s) for recombination mediated by a site specific recombinase.

As used herein, the terms "recombinase" or "site specific recombinase" include excisive or integrative proteins, enzymes, cofactors or associated proteins that are involved in recombination reactions involving one or more recombination sites (e.g., two, three, four, five, seven, ten, twelve, fifteen, twenty, thirty, fifty, etc.), which may be wild-type proteins (see Landy, Current Opinion in Biotechnology 3:699-707 (1993)), or mutants, derivatives (e.g., fusion proteins containing the recombination protein sequences or fragments thereof), fragments, and variants thereof. Illustrative examples of recombinases suitable for use in particular embodiments of the present invention include, but are not limited to: Cre, Int, IHF, Xis, Flp, Fis, Hin, Gin, (DC31, Cin, Tn3 resolvase, TndX, XerC, XerD, TnpX, Hjc, Gin, SpCCE1, and ParA.

G. Viral Vectors

In particular embodiments, population of cells comprising T cells, e.g., PBMCs, or a purified population of T cells is transduced with a retroviral vector, e.g., a lentiviral vector, encoding an engineered TCR or CAR as contemplated herein. The transduced T cells elicit a stable, long-term, and persistent T-cell response.

As used herein, the term "retrovirus" refers to an RNA virus that reverse transcribes its genomic RNA into a linear double-stranded DNA copy and subsequently covalently integrates its genomic DNA into a host genome. Illustrative retroviruses suitable for use in particular embodiments, include, but are not limited to: Moloney murine leukemia virus (M-MuLV), Moloney murine sarcoma virus (MoMSV), Harvey murine sarcoma virus (HaMuSV), murine mammary tumor virus (MuMTV), gibbon ape leukemia virus (GaLV), feline leukemia virus (FLV), spumavirus, Friend murine leukemia virus, Murine Stem Cell Virus (MSCV) and Rous Sarcoma Virus (RSV)) and lentivirus.

As used herein, the term "lentivirus" refers to a group (or genus) of complex retroviruses. Illustrative lentiviruses include, but are not limited to: HIV (human immunodeficiency virus; including HIV type 1, and HIV type 2); visna-maedi virus (VMV) virus; the caprine arthritis-encephalitis virus (CAEV); equine infectious anemia virus (EIAV); feline immunodeficiency virus (FIV); bovine immune deficiency virus (BIV); and simian immunodeficiency virus (SIV). In one embodiment, HIV based vector backbones (i.e., HIV cis-acting sequence elements) are preferred.

The term "vector" is used herein to refer to a nucleic acid molecule capable transferring or transporting another nucleic acid molecule. The transferred nucleic acid is generally linked to, e.g., inserted into, the vector nucleic acid molecule. A vector may include sequences that direct autonomous replication in a cell, or may include sequences sufficient to allow integration into host cell DNA. Useful vectors include, for example, plasmids (e.g., DNA plasmids or RNA plasmids), transposons, cosmids, bacterial artificial chromosomes, and viral vectors. Useful viral vectors include, e.g., replication defective retroviruses and lentiviruses.

As will be evident to one of skill in the art, the term "viral vector" is widely used to refer either to a nucleic acid molecule (e.g., a transfer plasmid) that includes virus-derived nucleic acid elements that typically facilitate transfer of the nucleic acid molecule or integration into the genome of a cell or to a viral particle that mediates nucleic acid transfer. Viral particles will typically include various viral components and sometimes also host cell components in addition to nucleic acid(s).

The term viral vector may refer either to a virus or viral particle capable of transferring a nucleic acid into a cell or to the transferred nucleic acid itself. Viral vectors and transfer plasmids contain structural and/or functional genetic elements that are primarily derived from a virus. The term "retroviral vector" refers to a viral vector or plasmid containing structural and functional genetic elements, or portions thereof, that are primarily derived from a retrovirus. The term "lentiviral vector" refers to a viral vector or plasmid containing structural and functional genetic elements, or portions thereof, including LTRs that are primarily derived from a lentivirus. The term "hybrid vector" refers to a vector, LTR or other nucleic acid containing both retroviral, e.g., lentiviral, sequences and non-lentiviral viral sequences. In one embodiment, a hybrid vector refers to a vector or transfer plasmid comprising retroviral e.g., lentiviral, sequences for reverse transcription, replication, integration and/or packaging.

In particular embodiments, the terms "lentiviral vector," "lentiviral expression vector" may be used to refer to lentiviral transfer plasmids and/or infectious lentiviral particles. Where reference is made herein to elements such as cloning sites, promoters, regulatory elements, heterologous nucleic acids, etc., it is to be understood that the sequences of these elements are present in RNA form in the lentiviral particles of the invention and are present in DNA form in the DNA plasmids of the invention.

At each end of the provirus are structures called "long terminal repeats" or "LTRs." The term "long terminal repeat (LTR)" refers to domains of base pairs located at the ends of retroviral DNAs which, in their natural sequence context, are direct repeats and contain U3, R and U5 regions. LTRs generally provide functions fundamental to the expression of retroviral genes (e.g., promotion, initiation and polyadenylation of gene transcripts) and to viral replication. The LTR contains numerous regulatory signals including transcriptional control elements, polyadenylation signals and sequences needed for replication and integration of the viral genome. The viral LTR is divided into three regions called U3, R and U5. The U3 region contains the enhancer and promoter elements. The U5 region is the sequence between the primer binding site and the R region and contains the polyadenylation sequence. The R (repeat) region is flanked by the U3 and U5 regions. The LTR composed of U3, R and U5 regions and appears at both the 5' and 3' ends of the viral genome. Adjacent to the 5' LTR are sequences necessary for reverse transcription of the genome (the tRNA primer binding site) and for efficient packaging of viral RNA into particles (the Psi site).

As used herein, the term "packaging signal" or "packaging sequence" refers to sequences located within the retroviral genome which are required for insertion of the viral RNA into the viral capsid or particle, see e.g., Clever et al., 1995. *J. of Virology*, Vol. 69, No. 4; pp. 2101-2109. Several retroviral vectors use the minimal packaging signal (also referred to as the psi [Ψ] sequence) needed for encapsidation of the viral genome. Thus, as used herein, the terms "packaging sequence," "packaging signal," "psi" and the symbol "Ψ" are used in reference to the non-coding sequence required for encapsidation of retroviral RNA strands during viral particle formation.

In various embodiments, vectors comprise modified 5' LTR and/or 3' LTRs. Either or both of the LTR may comprise one or more modifications including, but not limited to, one or more deletions, insertions, or substitutions. Modifications of the 3' LTR are often made to improve the safety of lentiviral or retroviral systems by rendering viruses replication-defective. As used herein, the term "replication-defective" refers to virus that is not capable of complete, effective replication such that infective virions are not produced (e.g., replication-defective lentiviral progeny). The term "replication-competent" refers to wild-type virus or mutant virus that is capable of replication, such that viral replication of the virus is capable of producing infective virions (e.g., replication-competent lentiviral progeny).

"Self-inactivating" (SIN) vectors refers to replication-defective vectors, e.g., retroviral or lentiviral vectors, in which the right (3') LTR enhancer-promoter region, known as the U3 region, has been modified (e.g., by deletion or substitution) to prevent viral transcription beyond the first round of viral replication. This is because the right (3') LTR U3 region is used as a template for the left (5') LTR U3 region during viral replication and, thus, the viral transcript cannot be made without the U3 enhancer-promoter. In a further embodiment of the invention, the 3' LTR is modified such that the U5 region is replaced, for example, with an ideal poly(A) sequence. It should be noted that modifications to the LTRs such as modifications to the 3' LTR, the 5' LTR, or both 3' and 5' LTRs, are also included in the invention.

An additional safety enhancement is provided by replacing the U3 region of the 5' LTR with a heterologous promoter to drive transcription of the viral genome during production of viral particles. Examples of heterologous promoters which can be used include, for example, viral simian virus 40 (SV40) (e.g., early or late), cytomegalovirus (CMV) (e.g., immediate early), Moloney murine leukemia virus (MoMLV), Rous sarcoma virus (RSV), and herpes simplex virus (HSV) (thymidine kinase) promoters. Typical promoters are able to drive high levels of transcription in a Tat-independent manner. This replacement reduces the possibility of recombination to generate replication-competent virus because there is no complete U3 sequence in the virus production system. In certain embodiments, the heterologous promoter has additional advantages in controlling the manner in which the viral genome is transcribed. For example, the heterologous promoter can be inducible, such that transcription of all or part of the viral genome will occur only when the induction factors are present. Induction factors include, but are not limited to, one or more chemical compounds or the physiological conditions such as temperature or pH, in which the host cells are cultured.

In some embodiments, viral vectors comprise a TAR element. The term "TAR" refers to the "trans-activation response" genetic element located in the R region of lentiviral (e.g., HIV) LTRs. This element interacts with the lentiviral trans-activator (tat) genetic element to enhance viral replication. However, this element is not required in embodiments wherein the U3 region of the 5' LTR is replaced by a heterologous promoter.

The "R region" refers to the region within retroviral LTRs beginning at the start of the capping group (i.e., the start of transcription) and ending immediately prior to the start of the poly A tract. The R region is also defined as being flanked by the U3 and U5 regions. The R region plays a role during reverse transcription in permitting the transfer of nascent DNA from one end of the genome to the other.

As used herein, the term "FLAP element" refers to a nucleic acid whose sequence includes the central polypurine tract and central termination sequences (cPPT and CTS) of a retrovirus, e.g., HIV-1 or HIV-2. Suitable FLAP elements are described in U.S. Pat. No. 6,682,907 and in Zennou, et al., 2000, Cell, 101:173. During HIV-1 reverse transcription, central initiation of the plus-strand DNA at the central polypurine tract (cPPT) and central termination at the central termination sequence (CTS) lead to the formation of a three-stranded DNA structure: the HIV-1 central DNA flap. While not wishing to be bound by any theory, the DNA flap may act as a cis-active determinant of lentiviral genome nuclear import and/or may increase the titer of the virus. In particular embodiments, the retroviral or lentiviral vector backbones comprise one or more FLAP elements upstream or downstream of the heterologous genes of interest in the vectors. For example, in particular embodiments a transfer plasmid includes a FLAP element. In one embodiment, a vector of the invention comprises a FLAP element isolated from HIV-1.

In one embodiment, retroviral or lentiviral transfer vectors comprise one or more export elements. The term "export element" refers to a cis-acting post-transcriptional regulatory element which regulates the transport of an RNA transcript from the nucleus to the cytoplasm of a cell. Examples of RNA export elements include, but are not limited to, the human immunodeficiency virus (HIV) rev response element (RRE) (see e.g., Cullen et al., 1991. *J. Virol.* 65: 1053; and Cullen et al., 1991. *Cell* 58: 423), and the hepatitis B virus post-transcriptional regulatory element (HPRE). Generally, the RNA export element is placed within the 3' UTR of a gene, and can be inserted as one or multiple copies.

In particular embodiments, expression of heterologous sequences in viral vectors is increased by incorporating posttranscriptional regulatory elements, efficient polyadenylation sites, and optionally, transcription termination signals into the vectors. A variety of posttranscriptional regulatory elements can increase expression of a heterologous nucleic acid at the protein, e.g., woodchuck hepatitis virus posttranscriptional regulatory element (WPRE; Zufferey et al., 1999, *J. Virol.*, 73:2886); the posttranscriptional regulatory element present in hepatitis B virus (HPRE) (Huang et al., *Mol. Cell. Biol.*, 5:3864); and the like (Liu et al., 1995, *Genes Dev.*, 9:1766). In particular embodiments, vectors of the invention comprise a posttranscriptional regulatory element such as a WPRE or HPRE In particular embodiments, vectors of the invention lack or do not comprise a posttranscriptional regulatory element such as a WPRE or HPRE because in some instances these elements increase the risk of cellular transformation and/or do not substantially or significantly increase the amount of mRNA transcript or increase mRNA stability. Therefore, in some embodiments, vectors of the invention lack or do not comprise a WPRE or HPRE as an added safety measure.

Elements directing the efficient termination and polyadenylation of the heterologous nucleic acid transcripts increases heterologous gene expression. Transcription termination signals are generally found downstream of the polyadenylation signal. In particular embodiments, vectors comprise a polyadenylation sequence 3' of a polynucleotide encoding a polypeptide to be expressed. The term "polyA site" or "polyA sequence" as used herein denotes a DNA sequence which directs both the termination and polyadenylation of the nascent RNA transcript by RNA polymerase II. Polyadenylation sequences can promote mRNA stability by addition of a polyA tail to the 3' end of the coding sequence and thus, contribute to increased translational efficiency. Efficient polyadenylation of the recombinant transcript is desirable as transcripts lacking a poly A tail are unstable and are rapidly degraded. Illustrative examples of polyA signals that can be used in a vector of the invention, includes an ideal polyA sequence (e.g., AATAAA, ATTAAA, AGTAAA), a bovine growth hormone polyA sequence (BGHpA), a rabbit β-globin polyA sequence (rβgpA), or another suitable heterologous or endogenous polyA sequence known in the art.

In various embodiments, the vectors of the invention comprise a promoter operably linked to a polynucleotide encoding an engineered TCR or CAR polypeptide. The vectors may have one or more LTRs, wherein either LTR comprises one or more modifications, such as one or more nucleotide substitutions, additions, or deletions. The vectors may further comprise one of more accessory elements to increase transduction efficiency (e.g., a cPPT/FLAP), viral packaging (e.g., a Psi (Ψ) packaging signal, RRE), and/or other elements that increase therapeutic gene expression (e.g., poly (A) sequences), and may optionally comprise a WPRE or HPRE. The skilled artisan would appreciate that many other different embodiments can be fashioned from the existing embodiments of the invention.

A "host cell" includes cells transfected, infected, or transduced in vivo, ex vivo, or in vitro with a recombinant vector or a polynucleotide of the invention. Host cells may include packaging cells, producer cells, and cells infected with viral vectors. In particular embodiments, host cells infected with viral vector of the invention are administered to a subject in need of therapy. In certain embodiments, the term "target cell" is used interchangeably with host cell and refers to transfected, infected, or transduced cells of a desired cell type. In preferred embodiments, the target cell is a T cell.

Large scale viral particle production is often necessary to achieve a reasonable viral titer. Viral particles are produced by transfecting a transfer vector into a packaging cell line that comprises viral structural and/or accessory genes, e.g., gag, pol, env, tat, rev, vif, vpr, vpu, vpx, or nef genes or other retroviral genes.

As used herein, the term "packaging vector" refers to an expression vector or viral vector that lacks a packaging signal and comprises a polynucleotide encoding one, two, three, four or more viral structural and/or accessory genes. Typically, the packaging vectors are included in a packaging cell, and are introduced into the cell via transfection, transduction or infection. Methods for transfection, transduction or infection are well known by those of skill in the art. A retroviral/lentiviral transfer vector of the present invention can be introduced into a packaging cell line, via transfection, transduction or infection, to generate a producer cell or cell line. The packaging vectors of the present invention can be introduced into human cells or cell lines by standard methods including, e.g., calcium phosphate transfection, lipofection or electroporation. In some embodiments, the packaging vectors are introduced into the cells together with a dominant selectable marker, such as neomycin, hygromycin, puromycin, blastocidin, zeocin, thymidine kinase, DHFR, Gln synthetase or ADA, followed by selection in the presence of the appropriate drug and isolation of clones. A selectable marker gene can be linked physically to genes encoding by the packaging vector, e.g., by IRES or self cleaving viral peptides.

Viral envelope proteins (env) determine the range of host cells which can ultimately be infected and transformed by recombinant retroviruses generated from the cell lines. In the case of lentiviruses, such as HIV-1, HIV-2, SIV, FIV and EIV, the env proteins include gp41 and gp120. Preferably, the viral env proteins expressed by packaging cells of the invention are encoded on a separate vector from the viral gag and pol genes, as has been previously described.

Illustrative examples of retroviral-derived env genes which can be employed in the invention include, but are not limited to: MLV envelopes, 10A1 envelope, BAEV, FeLV-B, RD114, SSAV, Ebola, Sendai, FPV (Fowl plague virus), and influenza virus envelopes.

Similarly, genes encoding envelopes from RNA viruses (e.g., RNA virus families of Picomaviridae, Calciviridae, Astroviridae, Togaviridae, Flaviviridae, Coronaviridae, Paramyxoviridae, Rhabdoviridae, Filoviridae, Orthomyxoviridae, Bunyaviridae, Arenaviridae, Reoviridae, Bimaviridae, Retroviridae) as well as from the DNA viruses (families of Hepadnaviridae, Circoviridae, Parvoviridae, Papovaviridae, Adenoviridae, Herpesviridae, Poxyiridae, and Iridoviridae) may be utilized. Representative examples include, FeLV, VEE, HFVW, WDSV, SFV, Rabies, ALV, BIV, BLV, EBV, CAEV, SNV, ChTLV, STLV, MPMV, SMRV, RAV, FuSV, MH2, AEV, AMV, CT 10, and EIAV.

In other embodiments, envelope proteins for pseudotyping a virus of present invention include, but are not limited to any of the following virus: Influenza A such as H1N1, H1N2, H3N2 and H5N1 (bird flu), Influenza B, Influenza C virus, Hepatitis A virus, Hepatitis B virus, Hepatitis C virus, Hepatitis D virus, Hepatitis E virus, Rotavirus, any virus of the Norwalk virus group, enteric adenoviruses, parvovirus, Dengue fever virus, Monkey pox, Mononegavirales, Lyssavirus such as rabies virus, Lagos bat virus, Mokola virus, Duvenhage virus, European bat virus 1 & 2 and Australian bat virus, Ephemerovirus, Vesiculovirus, Vesicular Stomatitis Virus (VSV), Herpesviruses such as Herpes simplex virus types 1 and 2, varicella zoster, cytomegalovirus, Epstein-Bar virus (EBV), human herpesviruses (HHV), human herpesvirus type 6 and 8, Human immunodeficiency virus (HIV), papilloma virus, murine gammaherpesvirus, Arenaviruses such as Argentine hemorrhagic fever virus, Bolivian hemorrhagic fever virus, Sabia-associated hemorrhagic fever virus, Venezuelan hemorrhagic fever virus, Lassa fever virus, Machupo virus, Lymphocytic choriomeningitis virus (LCMV), Bunyaviridiae such as Crimean-Congo hemorrhagic fever virus, Hantavirus, hemorrhagic fever with renal syndrome causing virus, Rift Valley fever virus, Filoviridae (filovirus) including Ebola hemorrhagic fever and Marburg hemorrhagic fever, Flaviviridae including Kaysanur Forest disease virus, Omsk hemorrhagic fever virus, Tick-borne encephalitis causing virus and Paramyxoviridae such as Hendra virus and Nipah virus, variola major and variola minor (smallpox), alphaviruses such as Venezuelan equine encephalitis virus, eastern equine encephalitis virus, western equine encephalitis virus, SARS-associated coronavirus (SARS-CoV), West Nile virus, any encephaliltis causing virus.

In one embodiment, the invention provides packaging cells which produce recombinant retrovirus, e.g., lentivirus, pseudotyped with the VSV-G glycoprotein.

The terms "pseudotype" or "pseudotyping" as used herein, refer to a virus whose viral envelope proteins have been substituted with those of another virus possessing preferable characteristics. For example, HIV can be pseudotyped with vesicular stomatitis virus G-protein (VSV-G) envelope proteins, which allows HIV to infect a wider range of cells because HIV envelope proteins (encoded by the env gene) normally target the virus to CD4+ presenting cells. In a preferred embodiment of the invention, lentiviral envelope proteins are pseudotyped with VSV-G. In one embodiment, the invention provides packaging cells which produce recombinant retrovirus, e.g., lentivirus, pseudotyped with the VSV-G envelope glycoprotein.

As used herein, the term "packaging cell lines" is used in reference to cell lines that do not contain a packaging signal, but do stably or transiently express viral structural proteins and replication enzymes (e.g., gag, pol and env) which are necessary for the correct packaging of viral particles. Any suitable cell line can be employed to prepare packaging cells of the invention. Generally, the cells are mammalian cells. In a particular embodiment, the cells used to produce the packaging cell line are human cells. Suitable cell lines which can be used include, for example, CHO cells, BHK cells, MDCK cells, C3H 10T1/2 cells, FLY cells, Psi-2 cells, BOSC 23 cells, PA317 cells, WEHI cells, COS cells, BSC 1 cells, BSC 40 cells, BMT 10 cells, VERO cells, W138 cells, MRC5 cells, A549 cells, HT1080 cells, 293 cells, 293T cells, B-50 cells, 3T3 cells, NIH3T3 cells, HepG2 cells, Saos-2 cells, Huh7 cells, HeLa cells, W163 cells, 211 cells, and 211A cells. In preferred embodiments, the packaging cells are 293 cells, 293T cells, or A549 cells.

As used herein, the term "producer cell line" refers to a cell line which is capable of producing recombinant retroviral particles, comprising a packaging cell line and a transfer vector construct comprising a packaging signal. The production of infectious viral particles and viral stock solutions may be carried out using conventional techniques. Methods of preparing viral stock solutions are known in the art and are illustrated by, e.g., Y. Soneoka et al. (1995) *Nucl. Acids Res.* 23:628-633, and N. R. Landau et al. (1992) *J. Virol.* 66:5110-5113. Infectious virus particles may be collected from the packaging cells using conventional techniques. For example, the infectious particles can be collected by cell lysis, or collection of the supernatant of the cell culture, as is known in the art. Optionally, the collected virus particles may be purified if desired. Suitable purification techniques are well known to those skilled in the art.

The delivery of a gene(s) or other polynucleotide sequence using a retroviral or lentiviral vector by means of viral infection rather than by transfection is referred to as "transduction." In one embodiment, retroviral vectors are transduced into a cell through infection and provirus integration. In certain embodiments, a target cell, e.g., a T cell, is "transduced" if it comprises a gene or other polynucleotide sequence delivered to the cell by infection using a viral or retroviral vector. In particular embodiments, a transduced cell comprises one or more genes or other polynucleotide sequences delivered by a retroviral or lentiviral vector in its cellular genome.

In particular embodiments, host cells transduced with viral vector of the invention that expresses one or more polypeptides, are administered to a subject to treat and/or prevent a B-cell malignancy. Other methods relating to the use of viral vectors in gene therapy, which may be utilized according to certain embodiments of the present invention, can be found in, e.g., Kay, M. A. (1997) *Chest* 111(6 Supp.):138S-142S; Ferry, N. and Heard, J. M. (1998) *Hum. Gene Ther.* 9:1975-81; Shiratory, Y. et al. (1999) *Liver* 19:265-74; Oka, K. et al. (2000) *Curr. Opin. Lipidol.* 11:179-86; Thule, P. M. and Liu, J. M. (2000) *Gene Ther.* 7:1744-52; Yang, N. S. (1992) *Crit. Rev. Biotechnol.* 12:335-56; Alt, M. (1995) *J. Hepatol.* 23:746-58; Brody, S. L. and Crystal, R. G. (1994) *Ann. N.Y. Acad. Sci.* 716:90-101; Strayer, D. S. (1999) *Expert Opin. Investig. Drugs* 8:2159-2172; Smith-Arica, J. R. and Bartlett, J. S. (2001) *Curr. Cardiol. Rep.* 3:43-49; and Lee, H. C. et al. (2000) *Nature* 408:483-8.

H. Compositions and Formulations

The compositions contemplated herein may comprise one or more polypeptides, polynucleotides, vectors comprising same, and T cell compositions, as contemplated herein. Compositions include, but are not limited to pharmaceutical compositions. A "pharmaceutical composition" refers to a composition formulated in pharmaceutically-acceptable or physiologically-acceptable solutions for administration to a cell or an animal, either alone, or in combination with one or more other modalities of therapy. It will also be understood that, if desired, the compositions of the invention may be administered in combination with other agents as well, such as, e.g., cytokines, growth factors, hormones, small molecules, chemotherapeutics, pro-drugs, drugs, antibodies, or other various pharmaceutically-active agents. There is virtually no limit to other components that may also be included in the compositions, provided that the additional agents do not adversely affect the ability of the composition to deliver the intended therapy.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein "pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, surfactant, or emulsifier which has been approved by the United States Food and Drug Administration as being acceptable for use in humans or domestic animals. Exemplary pharmaceutically acceptable carriers include, but are not limited to, to sugars, such as lactose, glucose and sucrose; starches, such as corn starch and potato starch; cellulose, and its derivatives, such as sodium carboxymethyl cellulose, ethyl cellulose and cellulose acetate; tragacanth; malt; gelatin; talc; cocoa butter, waxes, animal and vegetable fats, paraffins, silicones, bentonites, silicic acid, zinc oxide; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and any other compatible substances employed in pharmaceutical formulations.

In particular embodiments, compositions of the present invention comprise an amount modified T cells manufactured by the methods contemplated herein. It can generally be stated that a pharmaceutical composition comprising the T cells manufactured by the methods contemplated herein may be administered at a dosage of $10^2$ to $10^{10}$ cells/kg body weight, preferably $10^5$ to $10^6$ cells/kg body weight, including all integer values within those ranges. The number of cells will depend upon the ultimate use for which the composition is intended as will the type of cells included therein. For uses provided herein, the cells are generally in a volume of a liter or less, can be 500 mLs or less, even 250 mLs or 100 mLs or less. Hence the density of the desired cells is typically greater than $10^6$ cells/ml and generally is greater than $10^7$ cells/ml, generally $10^8$ cells/ml or greater. The clinically relevant number of immune cells can be apportioned into multiple infusions that cumulatively equal or exceed $10^5$, $10^6$, $10^7$, $10^8$, $10^9$, $10^{10}$, $10^{11}$, or $10^{12}$ cells. The cells may be allogeneic, syngeneic, xenogeneic, or autologous to the patient undergoing therapy. If desired, the treatment may also include administration of mitogens (e.g., PHA) or lymphokines, cytokines, and/or chemokines (e.g., IFN-γ, IL-2, IL-7, IL-15, IL-12, TNF-alpha, IL-18, and TNF-beta, GM-CSF, IL-4, IL-13, Flt3-L, RANTES, MIP1α, etc.) as described herein to enhance engraftment and function of infused T cells.

Generally, compositions comprising the cells activated and expanded as described herein may be utilized in the treatment and prevention of diseases that arise in individuals who are immunocompromised. In particular, compositions comprising the modified T cells manufactured by the methods contemplated herein are used in the treatment of cancer. The modified T cells of the present invention may be administered either alone, or as a pharmaceutical composition in combination with carriers, diluents, excipients, and/or with other components such as IL-2, IL-7, and/or IL-15 or other cytokines or cell populations. In particular embodiments, pharmaceutical compositions contemplated herein comprise an amount of genetically modified T cells, in combination with one or more pharmaceutically or physiologically acceptable carriers, diluents or excipients.

Pharmaceutical compositions comprising modified T cells contemplated herein may further comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for parenteral administration, e.g., intravascular (intravenous or intraarterial), intraperitoneal or intramuscular administration.

In one embodiment, the compositions are administered intravenously.

The liquid pharmaceutical compositions, whether they be solutions, suspensions or other like form, may include one or more of the following: DMSO, sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose.

In particular embodiments, the cells are frozen in infusible cryogenic medium, 50% plasmalyte and 50% Cryostor 10; 50/40/10 (XVIVO/HABS/DMSO); or Cryostor 10.

The parenteral preparation can be enclosed in glass or plastic bags, ampoules, disposable syringes or multiple dose vials. An injectable pharmaceutical composition is preferably sterile.

In a particular embodiment, compositions contemplated herein comprise an effective amount of an expanded modified T cell composition, alone or in combination with one or more therapeutic agents. Thus, the T cell compositions may be administered alone or in combination with other known cancer treatments, such as radiation therapy, chemotherapy, transplantation, immunotherapy, hormone therapy, photodynamic therapy, etc. The compositions may also be administered in combination with antibiotics. Such therapeutic agents may be accepted in the art as a standard treatment for a particular disease state as described herein, such as a particular cancer. Exemplary therapeutic agents contemplated include cytokines, growth factors, steroids, NSAIDs, DMARDs, anti-inflammatories, chemotherapeutics, radiotherapeutics, therapeutic antibodies, or other active and ancillary agents.

In certain embodiments, compositions comprising T cells contemplated herein may be administered in conjunction with any number of chemotherapeutic agents. Illustrative examples of chemotherapeutic agents include alkylating agents such as thiotepa and cyclophosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine resume; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; ellipitinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2, 2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL®, Bristol-Myers Squibb Oncology, Princeton, N.J.) and doxetaxel (TAXOTERE®., Rhne-Poulenc Rorer, Antony, France); chlorambucil; gemcitabine; 6-thioguanine; mercaptopurine; methotrexate; platinum analogs such as cisplatin and carboplatin; vinblastine; platinum; etoposide; ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylomithine (DMFO); retinoic acid derivatives such as Targretin™ (bexarotene), Panretin™ (alitretinoin); ONTAK™ (denileukin diftitox); esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

A variety of other therapeutic agents may be used in conjunction with the compositions described herein. In one embodiment, the composition comprising T cells is administered with an anti-inflammatory agent. Anti-inflammatory agents or drugs include, but are not limited to, steroids and glucocorticoids (including betamethasone, budesonide, dexamethasone, hydrocortisone acetate, hydrocortisone, hydrocortisone, methylprednisolone, prednisolone, prednisone, triamcinolone), nonsteroidal anti-inflammatory drugs (NSAIDS) including aspirin, ibuprofen, naproxen, methotrexate, sulfasalazine, leflunomide, anti-TNF medications, cyclophosphamide and mycophenolate.

Other exemplary NSAIDs are chosen from the group consisting of ibuprofen, naproxen, naproxen sodium, Cox-2 inhibitors such as VIOXX® (rofecoxib) and CELEBREX® (celecoxib), and sialylates. Exemplary analgesics are chosen from the group consisting of acetaminophen, oxycodone, tramadol of proporxyphene hydrochloride. Exemplary glucocorticoids are chosen from the group consisting of cortisone, dexamethasone, hydrocortisone, methylprednisolone, prednisolone, or prednisone. Exemplary biological response modifiers include molecules directed against cell surface markers (e.g., CD4, CD5, etc.), cytokine inhibitors, such as the TNF antagonists (e.g., etanercept (ENBREL®), adalimumab (HUMIRA®) and infliximab (REMICADE®), chemokine inhibitors and adhesion molecule inhibitors. The biological response modifiers include monoclonal antibodies as well as recombinant forms of molecules. Exemplary DMARDs include azathioprine, cyclophosphamide, cyclosporine, methotrexate, penicillamine, leflunomide, sulfasalazine, hydroxychloroquine, Gold (oral (auranofin) and intramuscular) and minocycline.

Illustrative examples of therapeutic antibodies suitable for combination with the CAR modified T cells contemplated herein, include but are not limited to, abagovomab, adecatumumab, afutuzumab, alemtuzumab, altumomab, amatuximab, anatumomab, arcitumomab, bavituximab, bectumomab, bevacizumab, bivatuzumab, blinatumomab, brentuximab, cantuzumab, catumaxomab, cetuximab, citatuzumab, cixutumumab, clivatuzumab, conatumumab, daratumumab, drozitumab, duligotumab, dusigitumab, detumomab, dacetuzumab, dalotuzumab, ecromeximab, elotuzumab, ensituximab, ertumaxomab, etaracizumab, farietuzumab, ficlatuzumab, figitumumab, flanvotumab, futuximab, ganitumab, gemtuzumab, girentuximab, glembatumumab, ibritumomab, igovomab, imgatuzumab, indatuximab, inotuzumab, intetumumab, ipilimumab, iratumumab, labetuzumab, lexatumumab, lintuzumab, lorvotuzumab, lucatumumab, mapatumumab, matuzumab, milatuzumab, minretumomab, mitumomab, moxetumomab, namatumab, naptumomab, necitumumab, nimotuzumab, nofetumomab, ocaratuzumab, ofatumumab, olaratumab, onartuzumab, oportuzumab, oregovomab, panitumumab, parsatuzumab, patritumab, pemtumomab, pertuzumab, pintumomab, pritumumab, racotumomab, radretumab, rilotumumab, rituximab, robatumumab, satumomab, sibrotuzumab, siltuximab, simtuzumab, solitomab, tacatuzumab, taplitumomab, tenatumomab, teprotumumab, tigatuzumab, tositumomab, trastuzumab, tucotuzumab, ublituximab, veltuzumab, vorsetuzumab, votumumab, zalutumumab, CC49 and 3F8.

In certain embodiments, the compositions described herein are administered in conjunction with a cytokine. By "cytokine" as used herein is meant a generic term for proteins released by one cell population that act on another cell as intercellular mediators. Examples of such cytokines are lymphokines, monokines, chemokines, e.g., RANTES, MIPla, and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-alpha and -beta; mullerian-inhibiting substance; mouse gonadotropin-associated peptide; inhibin; activin; vascular endothelial growth factor; integrin; thrombopoietin (TPO); nerve growth factors such as NGF-beta; platelet-growth factor; transforming growth factors (TGFs) such as TGF-alpha and TGF-beta; insulin-like growth factor-I and -II; erythropoietin (EPO); osteoinductive factors; interferons such as interferon-alpha, beta, and -gamma; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1alpha, IL-2, IL-3, IL-4, IL-5, IL-6, IL-7, IL-8, IL-9, IL-10, IL-11, IL-12; IL-15, IL-21, a tumor necrosis factor such as TNF-alpha or TNF-beta; and other polypeptide factors including LIF and kit ligand (KL). As used herein, the term cytokine includes proteins from natural sources or from recombinant cell culture, and biologically active equivalents of the native sequence cytokines.

I. Target Cells and Antigens

The present invention contemplates, in part, cell manufacturing platforms for producing genetically modified immune effector cells redirected to a target cell, e.g., a tumor or cancer cell, and that comprise engineered T cell receptors or CARs having a binding domain that binds to target antigens on the cells. Cancer cells can also spread to other parts of the body through the blood and lymph systems. There are several main types of cancer. Carcinoma is a cancer that begins in the skin or in tissues that line or cover internal organs. Sarcoma is a cancer that begins in bone, cartilage, fat, muscle, blood vessels, or other connective or supportive tissue. Leukemia is a cancer that starts in blood-forming tissue such as the bone marrow, and causes large numbers of abnormal blood cells to be produced and enter the blood. Lymphoma and multiple myeloma are cancers that begin in the cells of the immune system. Central nervous system cancers are cancers that begin in the tissues of the brain and spinal cord.

In one embodiment, the target cell expresses an antigen, e.g., target antigen, that is not substantially found on the surface of other normal (desired) cells. In one embodiment, the target cell is a pancreatic parenchymal cell, pancreatic duct cell, hepatic cell, cardiac muscle cell, skeletal muscle cell, osteoblast, skeletal myoblast, neuron, vascular endothelial cell, pigment cell, smooth muscle cell, glial cell, fat cell, bone cell, chondrocyte, pancreatic islet cell, CNS cell, PNS cell, liver cell, adipose cell, renal cell, lung cell, skin cell, ovary cell, follicular cell, epithelial cell, immune cell, or an endothelial cell.

In certain embodiments, the target cell is part of a pancreatic tissue, neural tissue, cardiac tissue, bone marrow, muscle tissue, bone tissue, skin tissue, liver tissue, hair follicles, vascular tissue, adipose tissue, lung tissue, and kidney tissue.

In a particular embodiment, the target cell is a tumor cell. In another particular embodiment, the target cell is a cancer cell, such as a cell in a patient with cancer. Exemplary cells that can be killed with the disclosed methods include cells of the following tumors: a liquid tumor such as a leukemia, including acute leukemia (such as acute lymphocytic leukemia, acute myelocytic leukemia, and myeloblastic, promyelocytic, myelomonocytic, monocytic and erythroleukemia), chronic leukemias (such as chronic myelocytic (granulocytic) leukemia and chronic lymphocytic leukemia), polycythemia vera, lymphoma, Hodgkin's disease, non-Hodgkin's lymphoma, multiple myeloma, Waldenstrom's macroglobulinemia, heavy chain disease).

In another embodiment, the cell is a solid tumor cell, such as sarcomas and carcinomas, fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, pancreatic cancer, breast cancer, ovarian cancer, prostate cancer, hepatocellular carcinomna, lung cancer, colorectal cancer, squamous cell carcinoma, basal cell carcinoma, adenocarcinoma (for example adenocarcinoma of the pancreas, colon, ovary, lung, breast, stomach, prostate, cervix, or esophagus), sweat gland carcinoma, sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, bladder carcinoma, CNS tumors (such as a glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma).

In one embodiment, the cancer is selected from the group consisting of: The method of claim 1, wherein the cancer is selected from the group consisting of Wilms' tumor, Ewing sarcoma, a neuroendocrine tumor, a glioblastoma, a neuroblastoma, a melanoma, skin cancer, breast cancer, colon cancer, rectal cancer, prostate cancer, liver cancer, renal cancer, pancreatic cancer, lung cancer, biliary cancer, cervical cancer, endometrial cancer, esophageal cancer, gastric cancer, head and neck cancer, medullary thyroid carcinoma, ovarian cancer, glioma, lymphoma, leukemia, myeloma, acute lymphoblastic leukemia, acute myelogenous leukemia, chronic lymphocytic leukemia, chronic myelogenous leukemia, Hodgkin's lymphoma, non-Hodgkin's lymphoma, and urinary bladder cancer.

In one embodiment, the target cell is a malignant cell of the liver, pancreas, lung, breast, bladder, brain, bone, thyroid, kidney, skin, and hematopoietic system. In another embodiment, the target cell is a cell in a liver cancer, pancreatic cancer, lung cancer, breast cancer, bladder cancer, brain cancer, bone cancer, thyroid cancer, kidney cancer, skin cancer, or hematological cancer.

In one embodiment, the target antigen is an epitope of alpha folate receptor, 5T4, $\alpha_v\beta_6$ integrin, BCMA, B7-H3, B7-H6, CAIX, CD19, CD20, CD22, CD30, CD33, CD44, CD44v6, CD44v7/8, CD70, CD79a, CD79b, CD123, CD138, CD171, CEA, CSPG4, EGFR, EGFR family including ErbB2 (HER2), EGFRvIII, EGP2, EGP40, EPCAM, EphA2, EpCAM, FAP, fetal AchR, FR$\alpha$, GD2, GD3, 'Glypican-3 (GPC3), HLA-A1+MAGE1, HLA-A2+MAGE1, HLA-A3+MAGE1, HLA-A1+NY-ESO-1, HLA-A2+NY-ESO-1, HLA-A3+NY-ESO-1, IL-11R$\alpha$, IL-13R$\alpha$2, Lambda, Lewis-Y, Kappa, Mesothelin, Muc1, Muc16, NCAM, NKG2D Ligands, NY-ESO-1, PRAME, PSCA, PSMA, ROR1, SSX, Survivin, TAG72, TEMs, or VEGFR2.

J. Therapeutic Methods

The modified T cells manufactured by the methods contemplated herein provide improved adoptive immunotherapy for use in the treatment of various conditions including, without limitation, cancer, infectious disease, autoimmune disease, inflammatory disease, and immunodeficiency. In particular embodiments, the specificity of a primary T cell is redirected to tumor or cancer cells by genetically modifying the primary T cell with an engineered TCR or CAR contemplated herein. In one embodiment, the present invention includes a type of cellular therapy where T cells are modified to express an engineered TCR or CAR that targets cancer cells that express a target antigen, and the modified T cell is infused to a recipient in need thereof. The infused cell is able to kill tumor cells in the recipient. Unlike antibody therapies, engineered TCR or CAR modified T cells are able to replicate in vivo; thus, contributing to long-term persistence that can lead to sustained cancer therapy.

In one embodiment, the engineered TCR and CAR T cells of the invention can undergo robust in vivo T cell expansion and can persist for an extended amount of time. In another embodiment, the engineered TCR or CAR T cells of the invention evolve into specific memory T cells that can be reactivated to inhibit any additional tumor formation or growth.

In particular embodiments, compositions comprising an immune effector cell genetically modified with a vector comprising a promoter operably linked to a polynucleotide encoding a CAR are used in the treatment of solid tumors or cancers including, without limitation, liver cancer, pancreatic cancer, lung cancer, breast cancer, bladder cancer, brain cancer, bone cancer, thyroid cancer, kidney cancer, or skin cancer.

In particular embodiments, compositions comprising an immune effector cell genetically modified with a vector comprising a promoter operably linked to a polynucleotide encoding an engineered TCR or CAR that comprises an antigen-specific binding domain that binds an epitope of PSCA or MUC1 are used in the treatment of various cancers including but not limited to pancreatic, bladder, and lung.

In particular embodiments, compositions comprising an immune effector cell genetically modified with a vector comprising a promoter operably linked to a polynucleotide encoding an engineered TCR or CAR are used in the treatment of liquid tumors, including but a leukemia, including acute leukemia (e.g., ALL, AML, and myeloblastic, promyelocytic, myelomonocytic, monocytic and erythroleukemia), chronic leukemias (e.g., CLL, SLL, CML, HCL), polycythemia vera, lymphoma, Hodgkin's disease, non-Hodgkin's lymphoma, multiple myeloma, Waldenstrom's macroglobulinemia, and heavy chain disease.

In particular embodiments, compositions comprising an immune effector cell genetically modified with a vector comprising a promoter operably linked to a polynucleotide encoding an engineered TCR or CAR are used in the treatment of B-cell malignancies, including but not limited to multiple myeloma (MM), non-Hodgkin's lymphoma (NHL), and chronic lymphocytic leukemia (CLL).

Multiple myeloma is a B-cell malignancy of mature plasma cell morphology characterized by the neoplastic transformation of a single clone of these types of cells. These plasma cells proliferate in BM and may invade adjacent bone and sometimes the blood. Variant forms of multiple myeloma include overt multiple myeloma, smoldering multiple myeloma, plasma cell leukemia, non-secretory myeloma, IgD myeloma, osteosclerotic myeloma, solitary plasmacytoma of bone, and extramedullary plasmacytoma (see, for example, Braunwald, et al. (eds), Harrison's Principles of Internal Medicine, 15th Edition (McGraw-Hill 2001)).

Non-Hodgkin lymphoma encompasses a large group of cancers of lymphocytes (white blood cells). Non-Hodgkin lymphomas can occur at any age and are often marked by lymph nodes that are larger than normal, fever, and weight loss. There are many different types of non-Hodgkin lymphoma. For example, non-Hodgkin's lymphoma can be divided into aggressive (fast-growing) and indolent (slow-growing) types. Although non-Hodgkin lymphomas can be derived from B-cells and T-cells, as used herein, the term "non-Hodgkin lymphoma" and "B-cell non-Hodgkin lymphoma" are used interchangeably. B-cell non-Hodgkin lymphomas (NHL) include Burkitt lymphoma, chronic lymphocytic leukemia/small lymphocytic lymphoma (CLL/SLL), diffuse large B-cell lymphoma, follicular lymphoma, immunoblastic large cell lymphoma, precursor B-lymphoblastic lymphoma, and mantle cell lymphoma. Lymphomas that occur after bone marrow or stem cell transplantation are usually B-cell non-Hodgkin lymphomas.

Chronic lymphocytic leukemia (CLL) is an indolent (slow-growing) cancer that causes a slow increase in immature white blood cells called B lymphocytes, or B cells. Cancer cells spread through the blood and bone marrow, and can also affect the lymph nodes or other organs such as the liver and spleen. CLL eventually causes the bone marrow to fail. Sometimes, in later stages of the disease, the disease is called small lymphocytic lymphoma.

In particular embodiments, methods comprising administering a therapeutically effective amount of modified T cells contemplated herein or a composition comprising the same, to a patient in need thereof, alone or in combination with one or more therapeutic agents, are provided. In certain embodiments, the cells of the invention are used in the treatment of patients at risk for developing a cancer. Thus, the present invention provides methods for the treatment or prevention of a cancer comprising administering to a subject in need thereof, a therapeutically effective amount of the modified T cells of the invention.

In one embodiment, a method of treating a cancer in a subject in need thereof comprises administering an effective amount, e.g., therapeutically effective amount of a composition comprising genetically modified immune effector cells contemplated herein. The quantity and frequency of administration will be determined by such factors as the condition of the patient, and the type and severity of the patient's disease, although appropriate dosages may be determined by clinical trials.

In one embodiment, the amount of modified T cells in the composition administered to a subject is at least $0.1 \times 10^7$ modified T cells/m2, at least $0.5 \times 10^7$ modified T cells/m2, at least $1 \times 10^7$ modified T cells/m2, at least $5 \times 10^7$ modified T cells/m2, at least $0.1 \times 10^8$ modified T cells/m2, at least $0.5 \times 10^8$ modified T cells/m2, at least $1 \times 10^8$ modified T cells/m2, at least $5 \times 10^8$ modified T cells/m2, or at least $1 \times 10^9$ modified T cells/m2, or any intervening number of modified T cells.

The number of modified T cells administered to a subject are often only a subset of the number of total cells administered to the subject. In a particular embodiment, the subject is administered at least $0.1 \times 10^7$ total T cells, at least $0.5 \times 10^7$ total T cells, at least $1 \times 10^7$ total T cells, at least $5 \times 10^7$ total T cells, at least $0.1 \times 10^8$ total T cells, at least $0.5 \times 10^8$ total T cells, at least $1 \times 10^8$ total T cells, at least $5 \times 10^8$ total T cells, at least $0.1 \times 10^9$ total T cells, at least $0.5 \times 10^9$ total T cells, at least $1 \times 10^9$ total T cells, at least $5 \times 10^9$ total T cells, or at least $0.1 \times 10^{10}$ total T cells or any intervening number of T cells.

One of ordinary skill in the art would recognize that multiple administrations of the compositions of the invention may be required to effect the desired therapy. For example a composition may be administered 1, 2, 3, 4, 5, 6, 7, 8, 9, or 10 or more times over a span of 1 week, 2 weeks, 3 weeks, 1 month, 2 months, 3 months, 4 months, 5 months, 6 months, 1 year, 2 years, 5, years, 10 years, or more.

In certain embodiments, it may be desirable to administer activated T cells to a subject and then subsequently redraw blood (or have an apheresis performed), activate T cells therefrom according to the present invention, and reinfuse the patient with these activated and expanded T cells. This process can be carried out multiple times every few weeks. In certain embodiments, T cells can be activated from blood draws of from 10 cc to 400 cc. In certain embodiments, T cells are activated from blood draws of 20 cc, 30 cc, 40 cc, 50 cc, 60 cc, 70 cc, 80 cc, 90 cc, 100 cc, 150 cc, 200 cc, 250 cc, 300 cc, 350 cc, or 400 cc or more. Not to be bound by theory, using this multiple blood draw/multiple reinfusion protocol may serve to select out certain populations of T cells.

The administration of the compositions contemplated herein may be carried out in any convenient manner, including by aerosol inhalation, injection, ingestion, transfusion, implantation or transplantation. In a preferred embodiment, compositions are administered parenterally. The phrases "parenteral administration" and "administered parenterally" as used herein refers to modes of administration other than enteral and topical administration, usually by injection, and includes, without limitation, intravascular, intravenous, intramuscular, intraarterial, intrathecal, intracapsular, intraorbital, intratumoral, intracardiac, intradermal, intraperitoneal, transtracheal, subcutaneous, subcuticular, intraarticular, subcapsular, subarachnoid, intraspinal and intrastemal injection and infusion. In one embodiment, the compositions contemplated herein are administered to a subject by direct injection into a tumor, lymph node, or site of infection.

In one embodiment, a subject in need thereof is administered an effective amount of a composition to increase a cellular immune response to a cancer in the subject. The immune response may include cellular immune responses mediated by cytotoxic T cells capable of killing infected cells, regulatory T cells, and helper T cell responses. Humoral immune responses, mediated primarily by helper T cells capable of activating B cells thus leading to antibody production, may also be induced. A variety of techniques may be used for analyzing the type of immune responses induced by the compositions of the present invention, which are well described in the art; e.g., Current Protocols in Immunology, Edited by: John E. Coligan, Ada M. Kruisbeek, David H. Margulies, Ethan M. Shevach, Warren Strober (2001) John Wiley & Sons, NY, N.Y.

In the case of T cell-mediated killing, CAR-ligand binding initiates CAR signaling to the T cell, resulting in activation of a variety of T cell signaling pathways that induce the T cell to produce or release proteins capable of inducing target cell apoptosis by various mechanisms. These T cell-mediated mechanisms include (but are not limited to) the transfer of intracellular cytotoxic granules from the T cell into the target cell, T cell secretion of pro-inflammatory cytokines that can induce target cell killing directly (or indirectly via recruitment of other killer effector cells), and up regulation of death receptor ligands (e.g. FasL) on the T cell surface that induce target cell apoptosis following binding to their cognate death receptor (e.g. Fas) on the target cell.

In one embodiment, the invention provides a method of treating a subject diagnosed with a cancer, comprising removing immune effector cells from the subject, genetically modifying said immune effector cells with a vector comprising a nucleic acid encoding an engineered TCR or CAR as contemplated herein, thereby producing a population of modified immune effector cells, and administering the population of modified immune effector cells to the same subject. In a preferred embodiment, the immune effector cells comprise T cells.

In certain embodiments, the present invention also provides methods for stimulating an immune effector cell mediated immune modulator response to a target cell population in a subject comprising the steps of administering to the subject an immune effector cell population expressing a nucleic acid construct encoding an engineered TCR or CAR molecule.

The methods for administering the cell compositions described herein includes any method which is effective to result in reintroduction of ex vivo genetically modified immune effector cells that either directly express an engineered TCR or CAR in the subject or on reintroduction of the genetically modified progenitors of immune effector cells that on introduction into a subject differentiate into mature immune effector cells that express the engineered TCR or CAR. One method comprises transducing peripheral blood T cells ex vivo with a nucleic acid construct in accordance with the invention and returning the transduced cells into the subject.

All publications, patent applications, and issued patents cited in this specification are herein incorporated by reference as if each individual publication, patent application, or issued patent were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims. The following examples are provided by way of illustration only and not by way of limitation. Those of skill in the art will readily recognize a variety of noncritical parameters that could be changed or modified to yield essentially similar results.

EXAMPLES

Adoptive Cellular Therapies (ACT) using autologous T cells engineered with Chimeric Antigen Receptors (CAR) is still challenged by the lack of a simple and robust manufacturing process. Due to the inherent complexity of live cell culture and patient to patient variability, it is important to develop methods that are efficient, repeatable, and scalable. Furthermore, development of a closed-system processing for ACT will be important in transforming ACT into standard treatment for a large number of patients.

Currently, existing T cell manufacturing methods include various complex steps for the isolation, activation, transduction and expansion of CAR T cells. In contrast, the present inventors used a small-scale research model to develop a simple, robust, well characterized, flexible, closed system T cell manufacturing platform that was transferred to large-scale clinical cGMP manufacturing process for engineered CAR T cells.

The manufacturing consistently achieved an average of 6.75 (+/−1.5) population doubling levels in 10 days. Average transduction efficiencies were 65.3% (+/−12.4%). The purity of the culture was consistently >98% CD3 cells. Phenotypically, the T cells expressed surface markers associated with tumor regression in animal models and clinical studies. In addition, the engineered CAR T cells exhibited cytotoxicity of antigen expressed targets both in vitro and in vivo.

Example 1

Small Scale Manufacturing Platform

A novel small scale manufacturing platform was established that was simple, reliable, and reproducible. The manufacturing platform was less complex and more robust than existing methods and implemented minimal manipulations in regards to activation, transduction, and expansion of CAR T cells. In addition, CAR T cells manufactured by the methods contemplated herein produced comparable, if not superior, engineered CAR T cell therapeutics produced by existing methods.

1. Harvesting PBMCs

PBMCs were used as the source of T cells for the small-scale research manufacturing platform. PBMCs from a whole blood draw can be manual isolation using a FICOLL™ gradient and washing. In this experiment, frozen PBMCs were used. Frozen vials of PBMCs were thawed in a 37° C. water bath. Once thawed, the PBMCs were transferred to a 50 mL conical tube containing ~20-30 mL of warm TCGM media then centrifuges at 175×g for 10 minutes. The supernatant was removed and the cell pellet was resuspended in a small volume of TCGM containing 250 IU/mL IL-2. An aliquot of the resuspended cells was counted via a multisizer or hemacytometer and the number of viable cells was determined.

2. Culture Initiation and Activation

At Day 0 (D0), PBMCs were seeded in T25 culture flasks at 1×10$^6$ cells/mL in a total volume of 10 mL TCGM with 250 IU/mL IL-2. T cells were activated by adding 5 uL of anti-CD3 antibody at 100 ng/uL and 5 uL of anti-CD28 antibody at 100 ng/uL to the culture. Once the PBMC cultures were set up, they were incubated lying down in a 37° C., 5% $CO_2$ incubator until Day 1 (D1) for subsequent transduced cells or until Day 3 (D3) if cells were not subsequently transduced.

3. Transduction

The titer of CAR T lentiviral vectors was determined. Cells were transduced at 1-2×10$^8$ TU/10$^6$ PBMCs (number of PBMCs plated at D0). Virus was diluted in TCGM+IL-2 to a volume of 2 mL or 20% v/v of the culture volume. Cells were transduced with virus for about 48 hours, until Day 3 (D3).

Several experiments determined that the transduction was most efficient at about 20 to 24 hours following activation of the cells. Cells were transduced with a GFP expressing lentivirus at 1-2×10$^8$ TU/10$^6$ PBMCs at D0, D1, and D2. Following transduction, GFP expressing cells were isolated by FACS analysis in order to determine the percentage of various types of T cells transduced and the vector copy number (VCN) of the transduced cells. GFP expressing cells were analyzed based on T cell marker expression. More transduced cells expressing GFP and the T cell markers CD3, CD8, or CD4 were identified when the cells were transduced 20 to 24 hours (D1) after activation. FIG. 1. In addition, the VCN was higher in cells transduced 20 to 24 hours (D1) after activation. FIG. 1.

Figure 2:
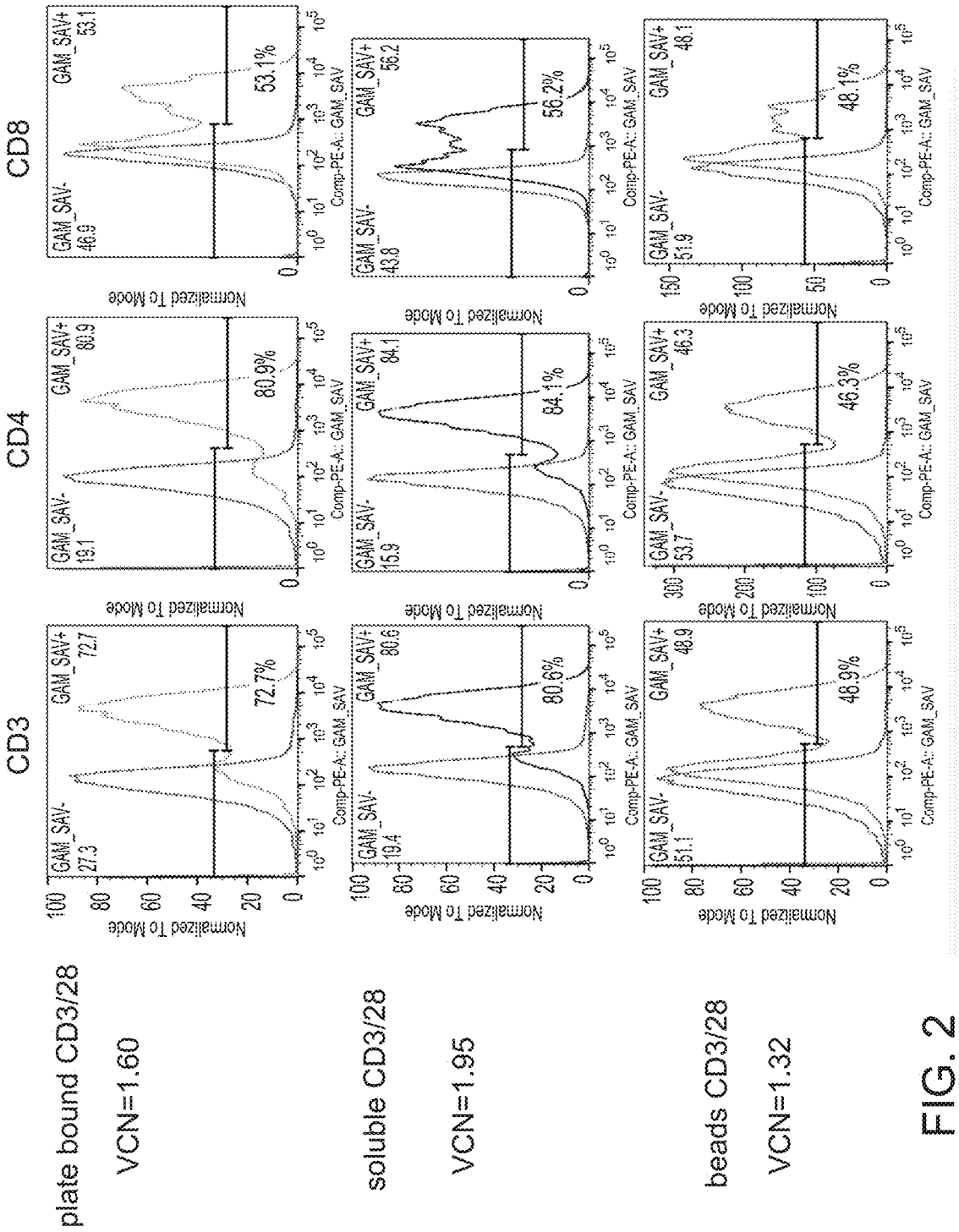
FIG. 2 shows the transduction efficiency of cells activated using different methods. PBMCs were activated using (i) plate bound anti-CD3 and anti-CD28 antibodies; (ii) soluble anti-CD3 and anti-CD28 antibodies; and (iii) bead bound anti-CD3 and anti-CD28 antibodies. Activated cells were transduced with an anti-CD19 CAR expressing lentivirus at $1-2\times10^8$ TU/$10^6$ PBMCs. Transduction efficiency and VCN was higher in GFP expressing the T cell markers CD3, CD8, or CD4 that were activated with soluble anti-CD3 and anti-CD28 antibodies compared to other methods.

Additional experiments determined that transduction efficiency T cells activated using soluble CD3 and CD28 ligands was comparable to the transduction efficiency of T cells activated by other methods. PBMCs were activated using (i) plate bound anti-CD3 and anti-CD28 antibodies at a concentration of 1 ug/mL for 20-24 hours; (ii) soluble anti-CD3 and anti-CD28 antibodies at a concentration of 50 ng/mL for 20-24 hours; and enriched lymphocytes from the same source as the PBMCs were activated using (iii) bead bound anti-CD3 and anti-CD28 antibodies, CD3/CD28 Dynabeads were used at a ratio of 3 beads to 1 Tcell for 20-24 hours. After activation, the cells were transduced with an anti-CD19 expressing lentivirus at 1-2×10$^8$ TU/10$^6$ PBMCs. More transduced cells expressing an anti-CD19 CAR and the T cell markers CD3, CD8, or CD4 were identified when the cells were activated with soluble anti-CD3 and anti-CD28 antibodies compared to other methods. FIG. 2. In addition, the VCN was also higher in cells activated with soluble anti-CD3 and anti-CD28 antibodies. FIG. 2.

Figure 3:
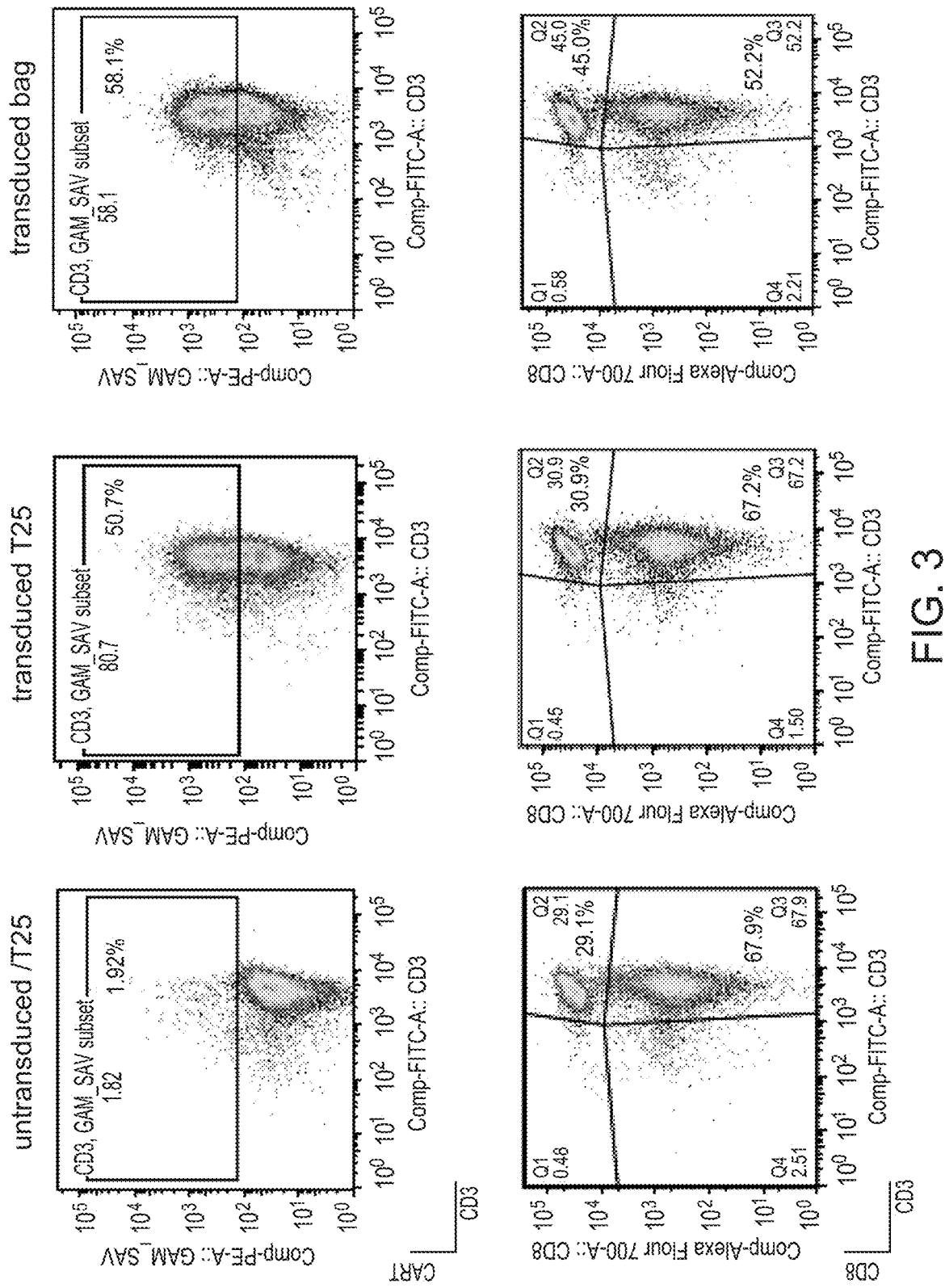
FIG. 3 shows that activation and transduction in cell culture bags was comparable to transduction in flasks. PBMCs were activated at D0 using soluble anti-CD3 and anti-CD28 antibodies at a concentration of 50 ng/mL. Activated cells were transduced with a kappaLC expressing lentivirus at $3\times10^8$ TU/$10^6$ PBMCs at D1. Transduction efficiency was comparable when the cells were activated and transduced in either cell culture bags or flasks. VCN was slightly higher in cells that were activated and transduced in cell culture bags.

Experiments also determined that activation and transduction in cell culture bags was comparable to transduction in flasks. PBMCs were activated at D0 using soluble anti-CD3 and anti-CD28 antibodies at a concentration of 50 ng/mL for 20-24 hours. After activation, the cells were transduced with a kappa$_{LC}$ expressing lentivirus at 3×10$^8$ TU/10$^6$ PBMCs at D1. The number of transduced cells expressing kappa$_L$c and the T cell markers CD3, CD8, or CD4 was comparable when the cells were activated and transduced in either cell culture bags or flasks. FIG. 3.

4. Expansion

Figure 4:
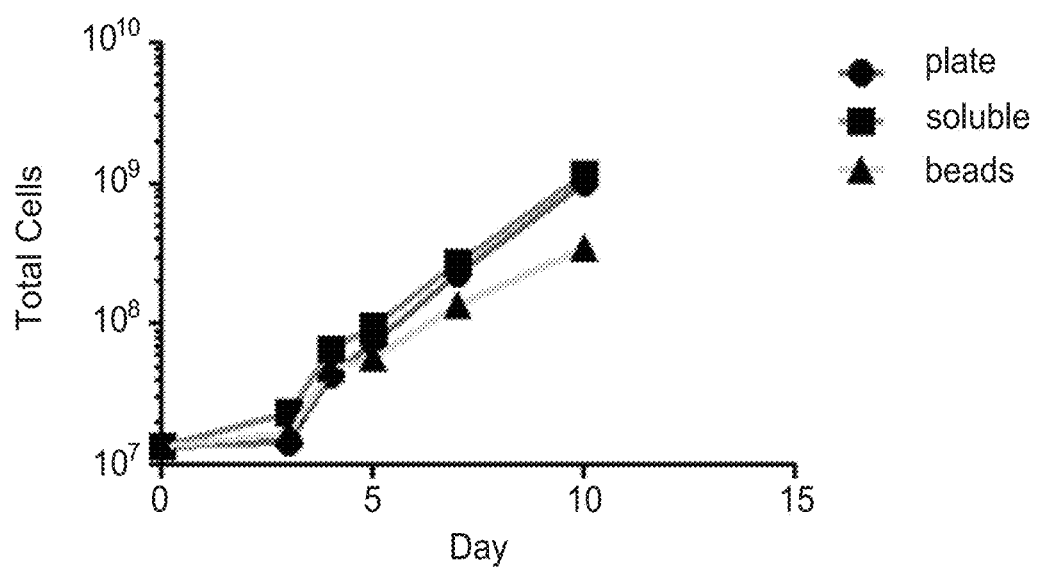
FIG. 4 shows T cell expansion among PBMCs activated by different methods was comparable. PBMCs were activated using (i) plate bound anti-CD3 and anti-CD28 antibodies; and (ii) soluble anti-CD3 and anti-CD28 antibodies; or purified lymphocytes were activated (iii) bead bound anti-CD3 and anti-CD28 antibodies. PBMCs and lymphocytes were from the same source. Activated cells were transduced with an anti-CD19 CAR expressing lentivirus at $1-2\times10^8$ TU/$10^6$ PBMCs. Cell expansion among PBMCs activated by the three methods was comparable throughout the ten day expansion culture period.
Figure 4:
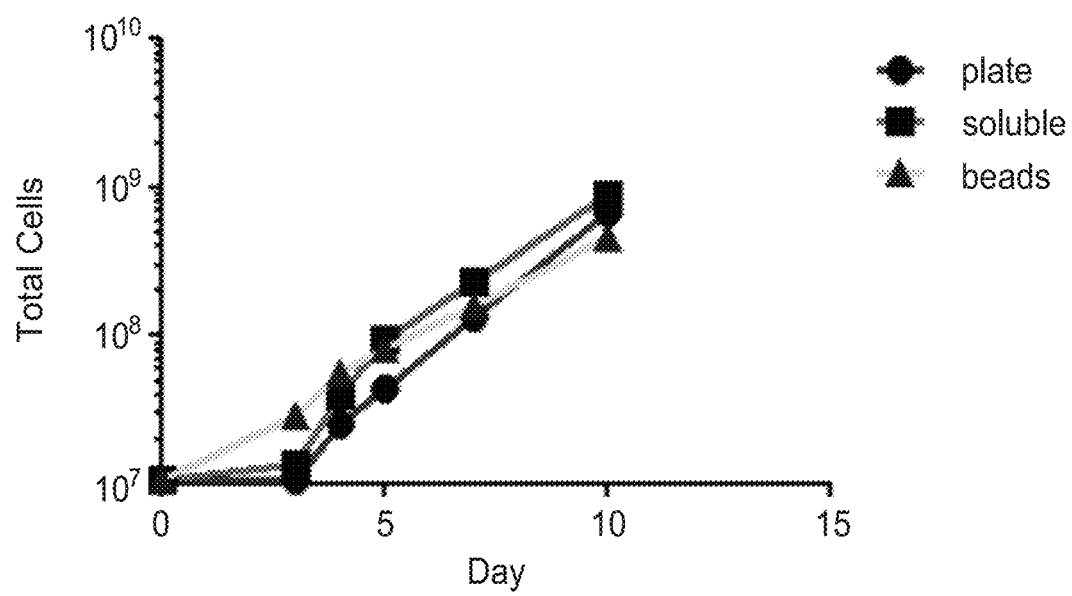

T cell expansion among PBMCs activated by different methods was also determined. PBMCs were activated using (i) plate bound anti-CD3 and anti-CD28 antibodies at a concentration of 1 ug/mL for 20-24 hours; (ii) soluble anti-CD3 and anti-CD28 antibodies at a concentration of 50 ng/mL for 20-24 hours; and (iii) bead bound anti-CD3 and anti-CD28 antibodies, Dynabeads were used at a ratio of 3:1 beads:Tcells for 20-24 hours. After activation, the cells were transduced with an anti-CD19 CAR expressing lentivirus at 1-2×10$^8$ TU/10$^6$ PBMCs. Activated and transduced cells were cultured for expansion for up to 10 days. Cell expansion among PBMCs activated by the three methods was comparable throughout the duration of the expansion culture period. FIG. 4.

Figure 5:
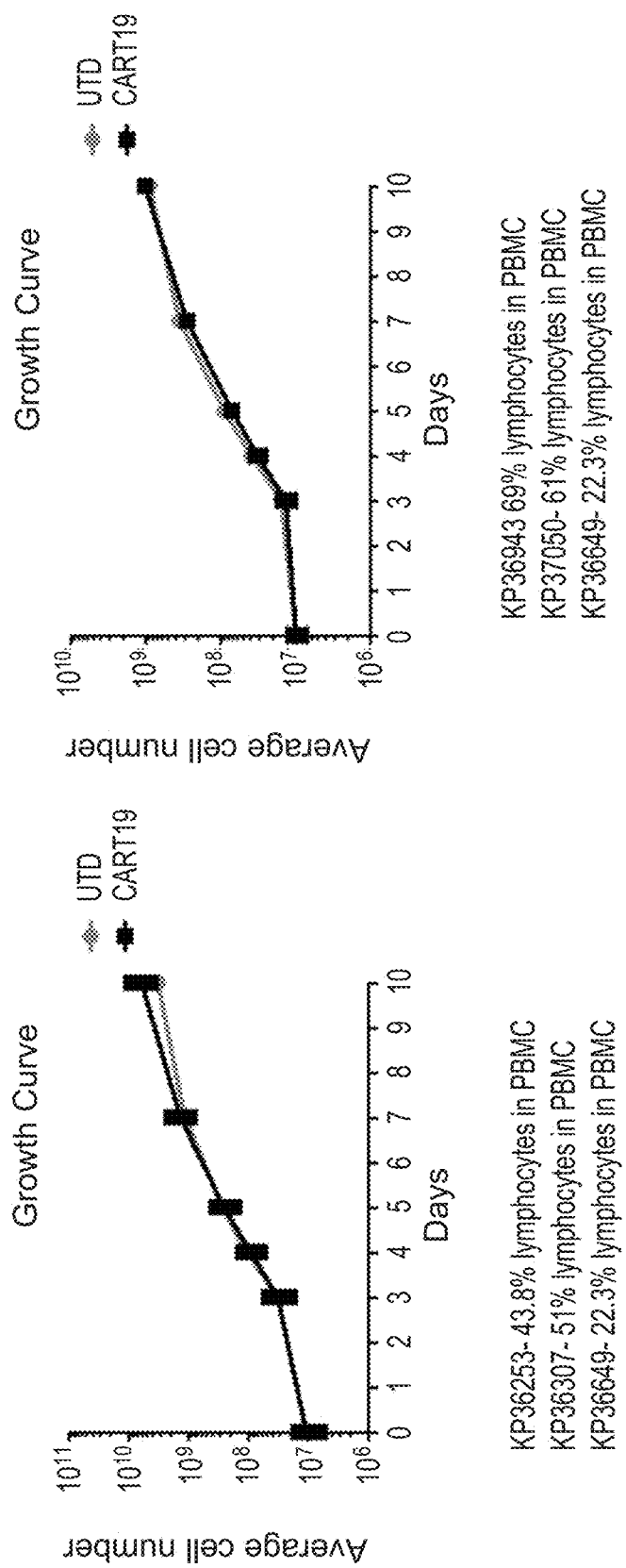
FIG. 5 shows PBMCs from multiple donors showed comparable and robust expansion. PBMCs were activated using soluble anti-CD3 and anti-CD28 antibodies. Activated cells were transduced with an anti-CD19 CAR expressing lentivirus at $1-2\times10^8$ TU/$10^6$ PBMCs. Activated and transduced cells from multiple donors cultured for 10 days showed comparable growth rates among each other and untransduced control (UTD). The number of lymphocytes present at day 10 in each expanded culture is also shown.
Figure 6:
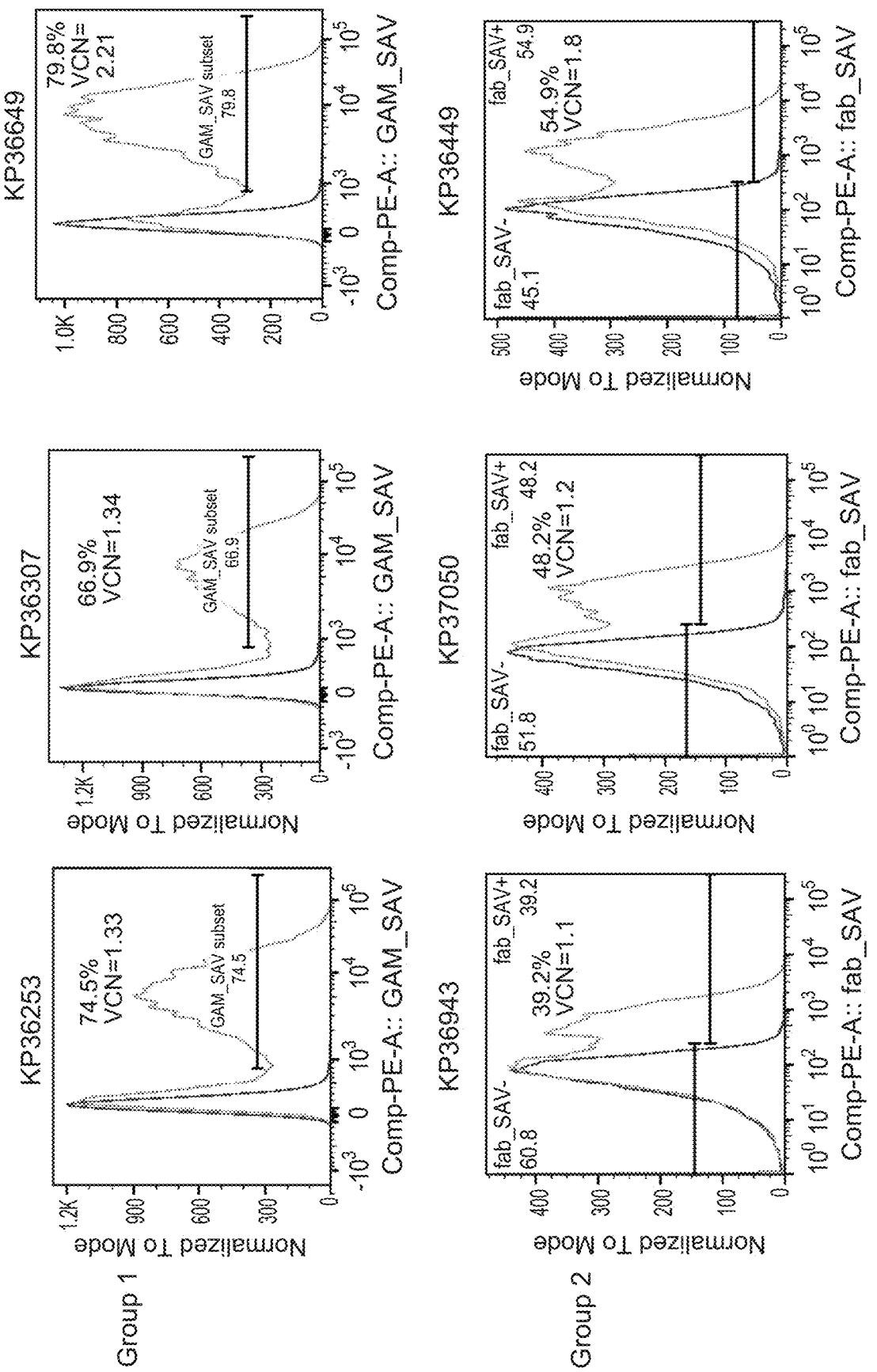
FIG. 6 is a representative FACS analysis that shows anti-CD19 CAR expression was comparable among the cell products generated from different patients, with an average of about 61% marking and a range of 29% to 80% (n=5). qPCR also demonstrated that the VCN among the cell products was comparable among the cell products generated from different patients.

PBMCs from multiple donors that were subjected to the T cells manufacturing methods contemplated herein showed reproducible and robust expansion, CAR cell surface expression, and VCN. PBMCs were activated using soluble anti-CD3 and anti-CD28 antibodies at a concentration of 50 ng/mL for 20-24 hours. Activated cells were transduced with an anti-CD19 CAR expressing lentivirus at 1-2×10$^8$ TU/10$^6$ PBMCs. Activated and transduced cells from multiple donors cultured for 10 days showed comparable growth rates among each other and untransduced control (UTD). FIG. 5. FIG. 5 also shows the number of lymphocytes present at day 10 in each expanded culture. FACS analysis determined that anti-CD19 expression was comparable among the cell products generated from different patients, with an average of about 61% marking and a range of 29% to 80% (n=5). FIG. 6. qPCR also demonstrated that the VCN among the cell products was comparable. FIG. 6.

5. Antigen Specific Tumor Clearance

Figure 7:
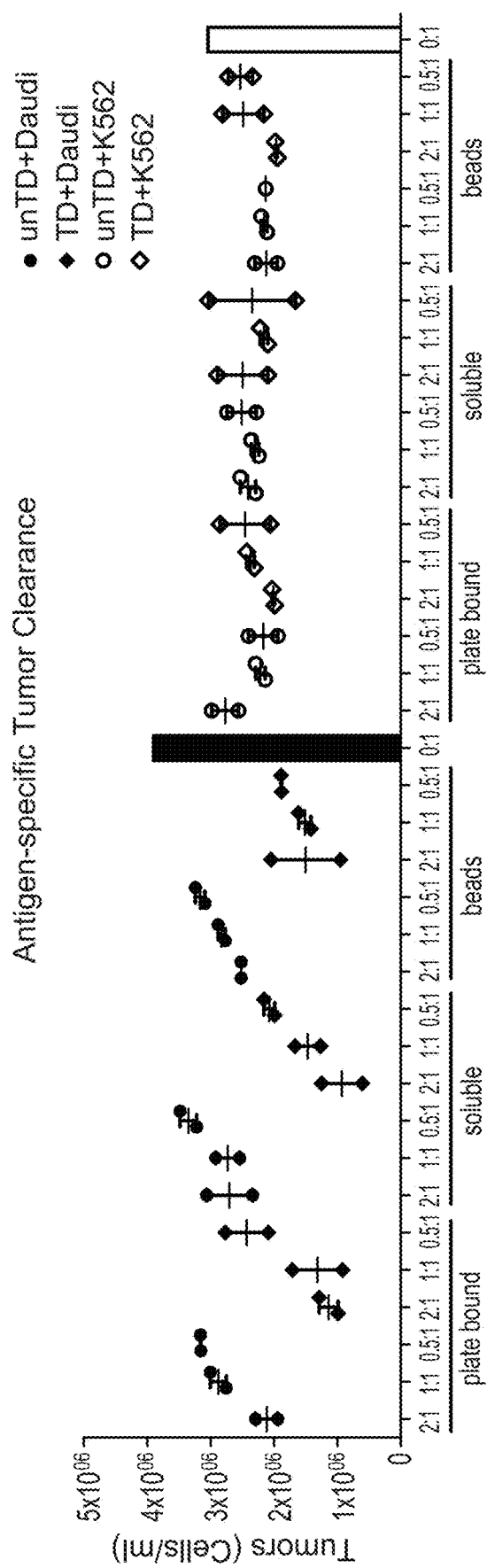
FIG. 7 shows that antigen specific tumor clearance by T cells activated using soluble antibodies was as good as, or better than T cells activated using other methods. PBMCs were activated using (i) plate bound anti-CD3 and anti-CD28 antibodies; (ii) soluble anti-CD3 and anti-CD28 antibodies; and (iii) bead bound anti-CD3 and anti-CD28 antibodies. Activated cells were transduced with an anti-CD19 CAR expressing lentivirus at $1-2\times10^8$ TU/$10^6$ PBMCs. Expanded anti-CD19 CAR T cells were co-cultured with CD19 expressing Daudi cells or non-CD19 expressing K562 cells. Anti-CD19 CAR T cells activated using soluble antibodies killed Daudi cells in an antigen specific manner, but not K562 cells as well as, or better than, anti-CD19 CAR T cells activated by the other methods.
Figure 8:
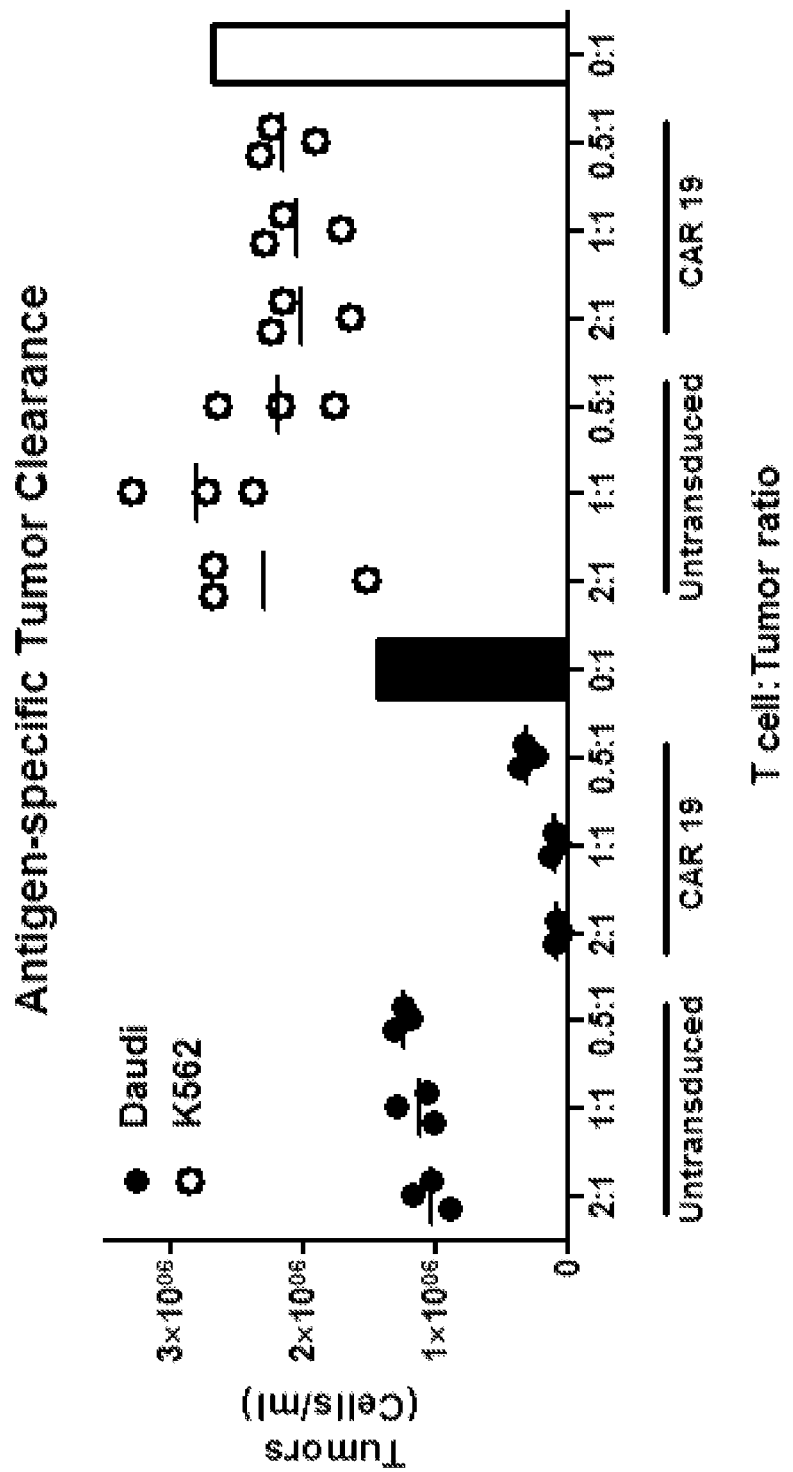
FIG. 8 shows a representative experiment of antigen specific tumor clearance by CAR T cells manufactured using the methods contemplated herein. PBMCs were activated using soluble anti-CD3 and anti-CD28 antibodies were transduced with an anti-CD19 CAR expressing lentivirus at $1-2\times10^8$ TU/$10^6$ PBMCs. Anti-CD19 CAR T cells killed CD19 expressing Daudi cells but not non-CD19 expressing K562 cells.

Antigen specific tumor clearance by T cells activated using soluble antibodies was as good as, or better than T cells activated using other methods. PBMCs were activated using (i) plate bound anti-CD3 and anti-CD28 antibodies at a concentration of 1 ug/mL for 20-24 hours; (ii) soluble anti-CD3 and anti-CD28 antibodies at a concentration of 50 ng/mL for 20-24 hours; and (iii) bead bound anti-CD3 and anti-CD28 antibodies, Dynabeads were used at a ratio of 3:1 beads:Tcells for 20-24 hours. After activation, the cells were transduced with an anti-CD19 CAR expressing lentivirus at 1-2×10$^8$ TU/10$^6$ PBMCs. Activated and transduced cells were cultured for expansion for up to 10 days. The therapeutic anti-CD19 CAR T cells were co-cultured with CD19 expressing Daudi cells or non-CD19 expressing K562 cells. After 10 days of co-culture anti-CD19 CAR T cells activated using soluble antibodies killed Daudi cells as well as, or better than, anti-CD19 CAR T cells activated using the other methods. FIG. 7 and FIG. 8.

6. The Small-Scale Manufacturing Platform

Overall, the small-scale manufacturing platform was used to develop a 10 day T cell expansion process: at D0, PBMCs are plated at a density of 1×10$^6$ cells/mL and activated using 50 ng/mL of anti-CD3 and anti-CD28 antibodies for about 24 hours; at D1, activated PBMCs were transduced with 2×10$^8$ TU/10$^6$ cells for about 24 hours to 48 hours; D3 to D9, transduced cells are expanded and reseeded to maintain log-phase growth. The T cell manufacturing process typically results in a 100-600 fold expansion of T cells depending on donor.

The foregoing experiments identified important elements for transferring the small scale research process to a large-scale clinical cGMP manufacturing process. The elements are shown in Table 1

TABLE 1

Small-Scale Elements Translated to Large-Scale Manufacturing Platform

| | |
|---|---|
| Starting Material | PBMC |
| Media Formulation | TCGM: XVIVO-15, supplemented with 5% HABS, 2 mM Glutamax, 10 mM HEPES, and 250 IU/mL of IL-2 (and optionally IL7 and/or IL-15) |
| Activation Method | 50 ng/mL soluble anti-CD3 and 50 ng/mL soluble anti-CD28 antibodies |
| Transduction | Transduction 20-24 hours post-activation |
| Expansion | Cells maintained in log-phase growth by seeding back at concentration of 0.3 × 10$^6$ cells/mL to 0.5 × 10$^6$ cells/mL |

7. Platform Robustness

Figure 16:
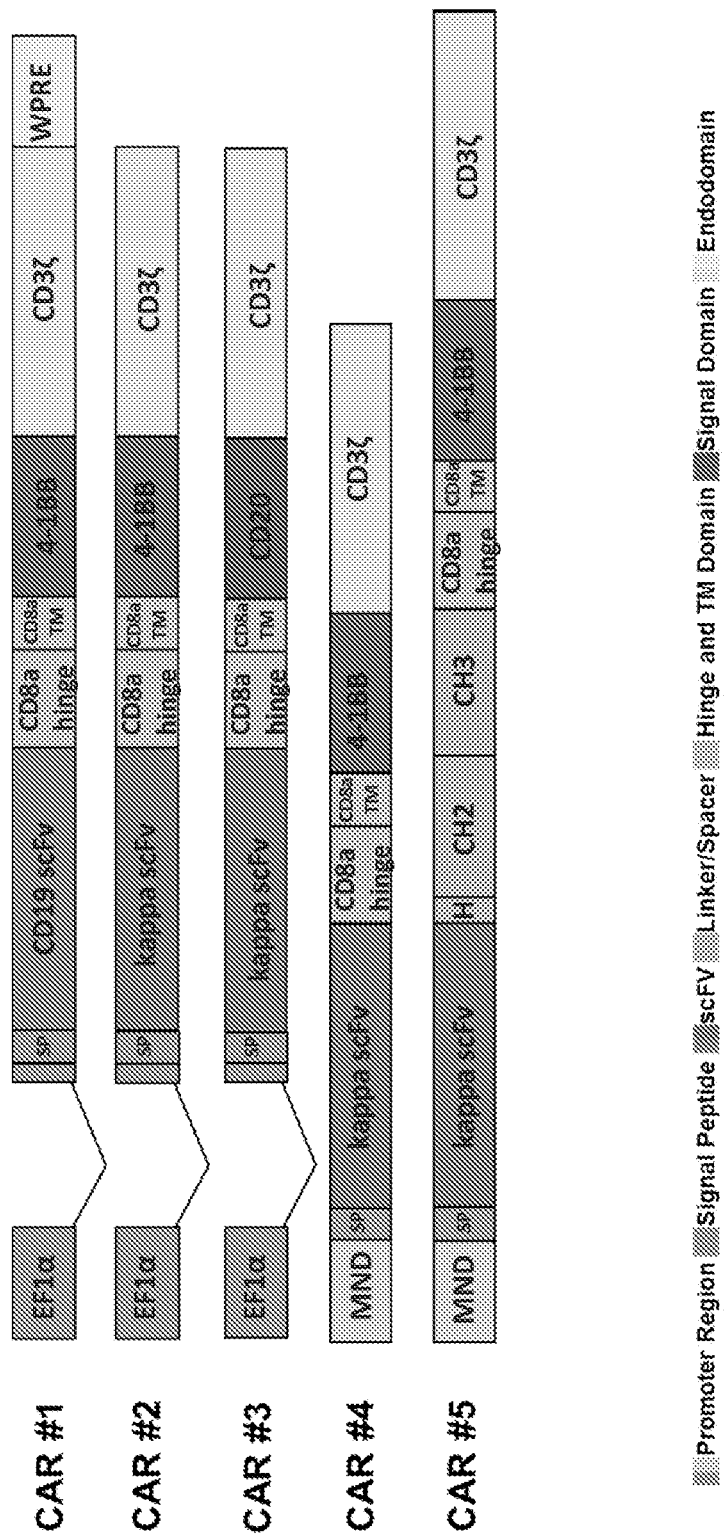
FIG. 16 shows a cartoon map of multiple lentiviral CAR constructs. Constructs varied in regards to promoter, scFV, +/− linker, hinge, transmembrane regions and signaling domains.

Manufacturing platform robustness was demonstrated by designing, manufacturing and evaluating multiple lentiviral CAR constructs. Constructs varied with regard to promoter, scFV, +/− linker, hinge, transmembrane regions and signaling domains used. FIG. 16.

CAR-encoding lentiviral vector (LV) supernatants were produced in HEK 293T cells as described elsewhere (e.g., Naldini et al., 1996, Dull et al., 1998 and Zufferey et al., 1998). 293 cells are transient transfected with 4-plasmids: a plasmid encoding HIV gag-pol, a plasmid encoding the VSV-G envelope protein, a plasmid encoding HIV rev protein, and a lentiviral transfer vector encoding a CAR, e.g., FIG. 16.

Figure 17A:
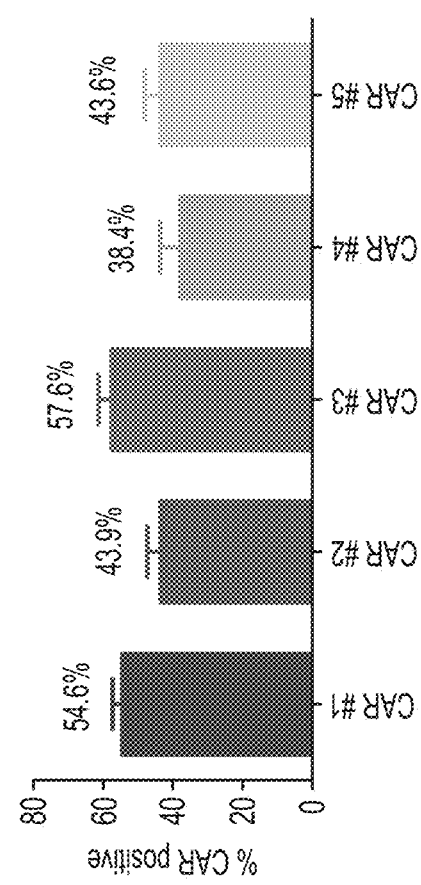
FIG. 17 shows various CAR T cell products showed (A) comparable growth rates; (B) VCN; and (C) cell surface expression of the different CAR constructs.
Figure 17B:
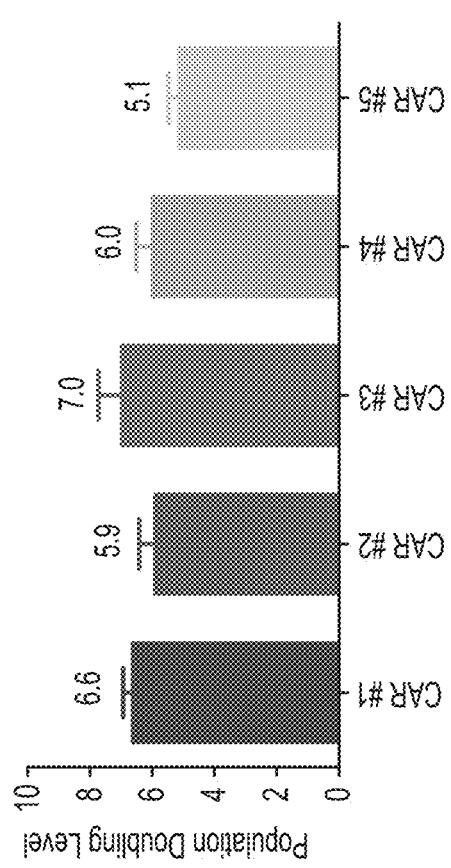
Figure 17C:
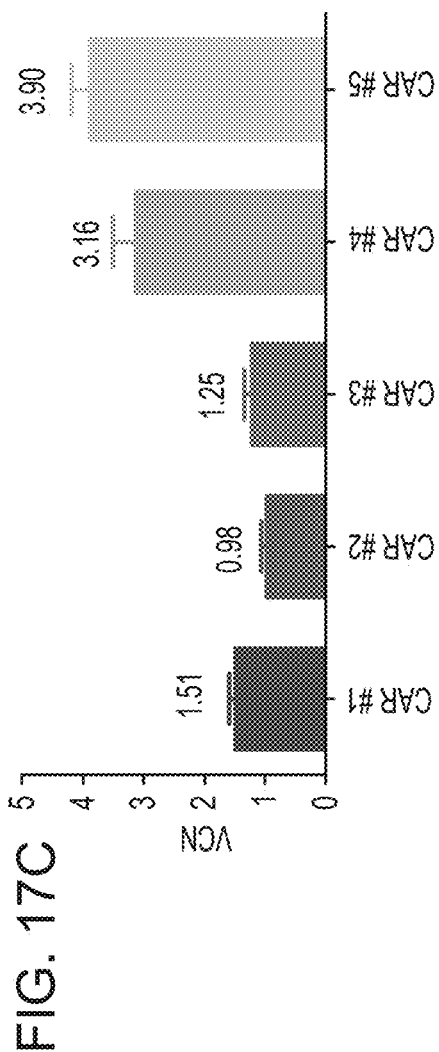

CAR T cells were manufactured as described in Example 1, supra. The various CAR T cell products showed comparable growth rates as determined by population doublings (FIG. 17A); qPCR showed that the VCN was comparable among the different CAR T cells, with approximately 1 to 4 copies per cell (FIG. 17B); and comparable cell surface expression of the different CAR construct was shown by FACS; percent marking ranged from about 40% to 60% depending on construct (FIG. 17C).

8. Generation of a Functional CART Drug Product

Figure 18:
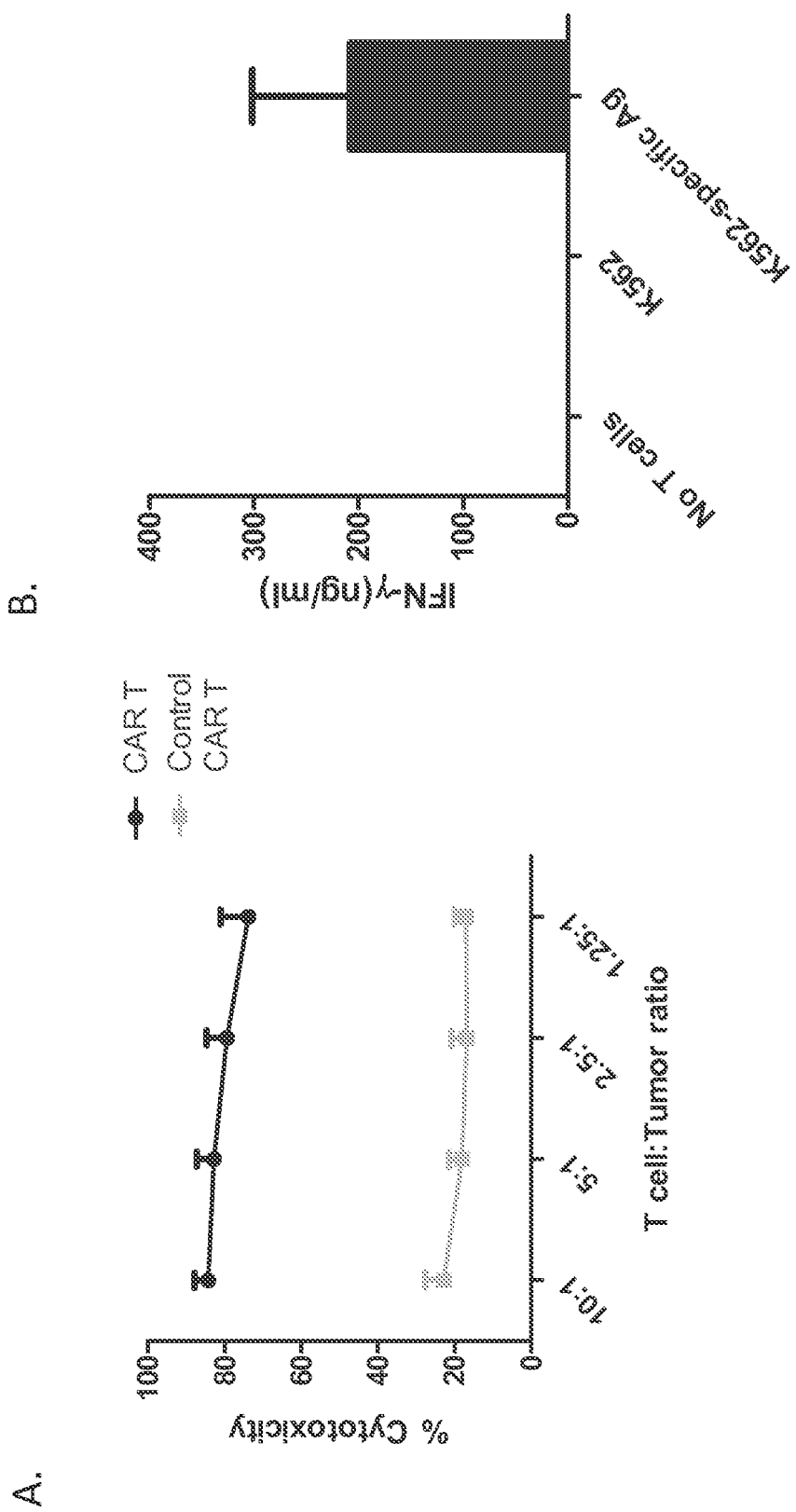
FIG. 18 shows antigen specific tumor clearance using expressing CAR T cells. (A). Anti-BCMA expressing CAR T cells killed BCMA expressing tumor cells labeled with carboxyfluorescein succinimidyl ester (CFSE); fluorescence was measured by FACS. (B). Anti-BCMA expressing CAR T cells were co-cultured with K562 cells and K562 cells genetically modified to express BCMA and supernatants were collected 24 hours later and assayed for IFN-γ release via ELISA. (n=3).

Anti-BCMA expressing CAR T cells were manufactured as described in Example 1, supra. These CAR T cells showed antigen specific tumor clearance. Anti-BCMA expressing CAR T cells were co-cultured for 4 hours with K562 cells, or K562 cells modified to express BCMA. Antigen expressing tumor cells were labeled with carboxyfluorescein succinimidyl ester (CFSE) and fluorescence was measured by FACS. Anti-BCMA expressing CAR T cells killed BCMA expressing K562 cells (FIG. 18A) and released IFN-γ (FIG. 18B). (n=3).

Example 2

Translation of Small Scale Research Platform to Large Scale Clinical cGMP Drug Manufacturing Platform The small-scale research process allowed for higher throughput evaluation of CAR constructs with assurance that data would be comparable for large scale cGMP drug manufacturing platform. This example provides data from representative experiments performed using the large scale clinical cGMP drug manufacturing platform.

1. Comparison Between Small-Scale and Large-Scale Manufacturing Methods

Figure 9:
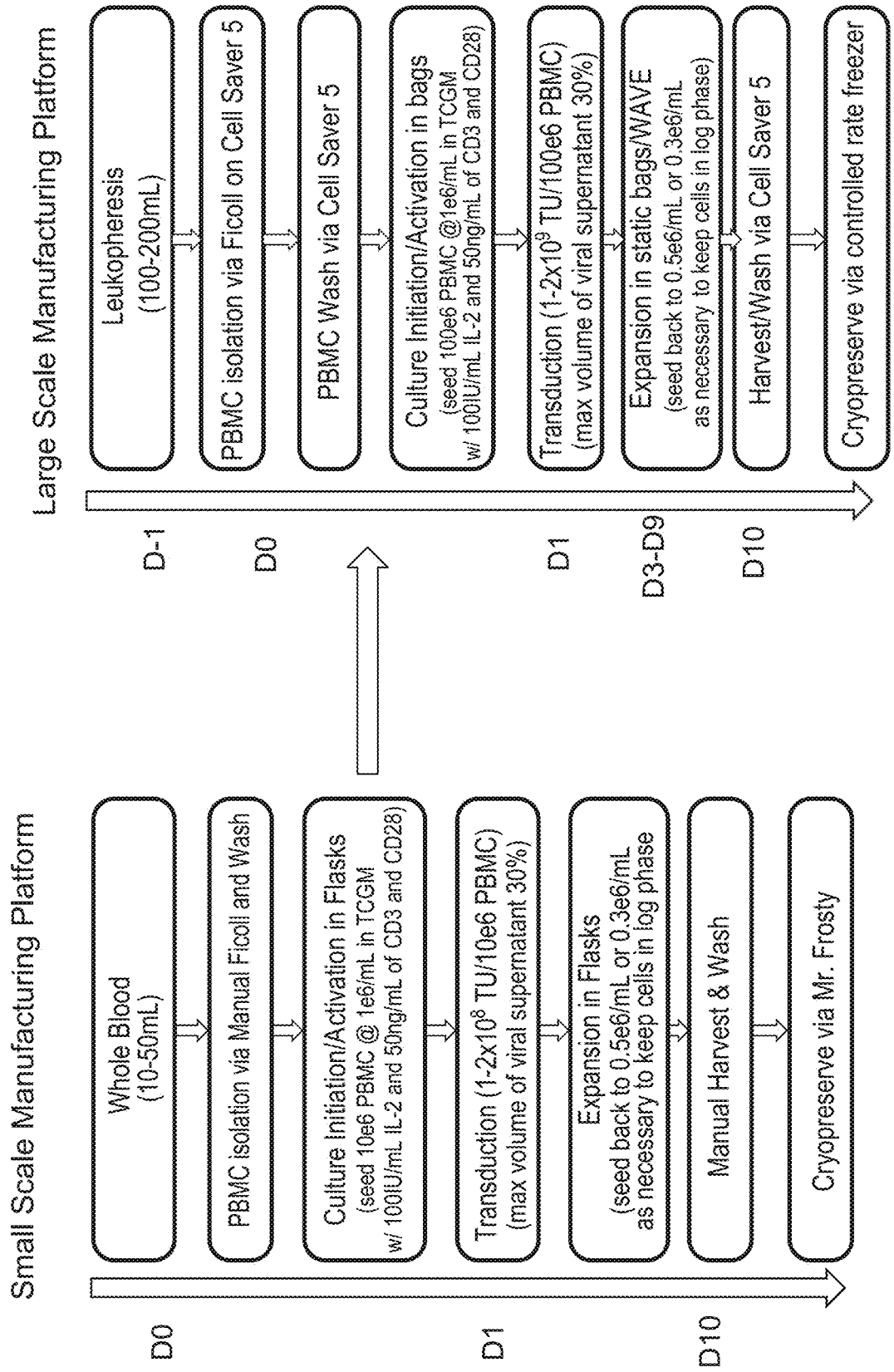
FIG. 9 shows a flowchart comparison of the small-scale research T cell manufacturing platform and the scaled up clinical cGMP drug manufacturing platform. The small-scale process allowed for higher throughput evaluation of CART constructs with assurance that data would be comparable for large scale cGMP manufacturing platform.
Figure 10:
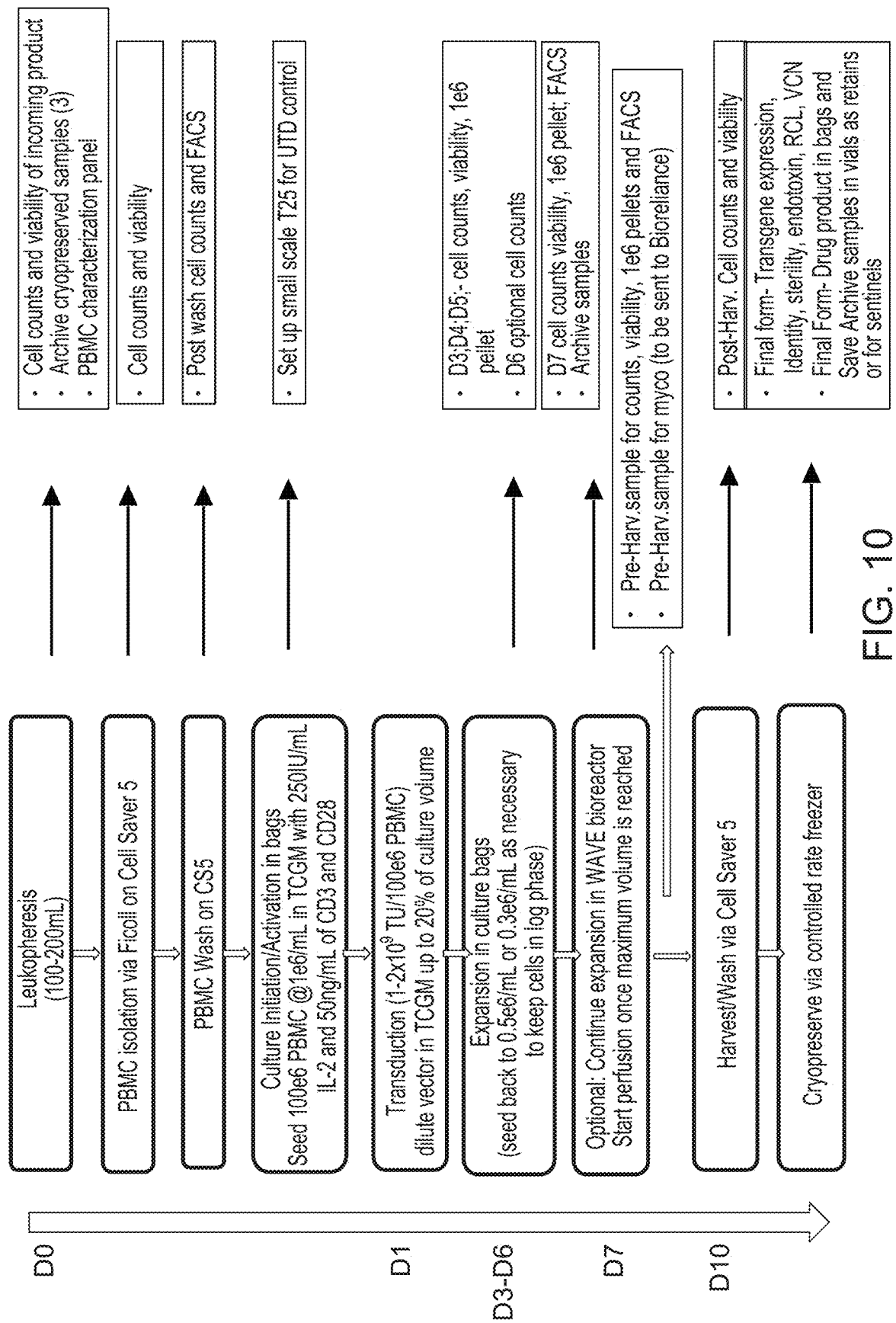
FIG. 10 shows a flowchart of the T cell manufacturing platform using fresh PBMCs, cell culture bags, and optionally a WAVE bioreactor.
Figure 11:
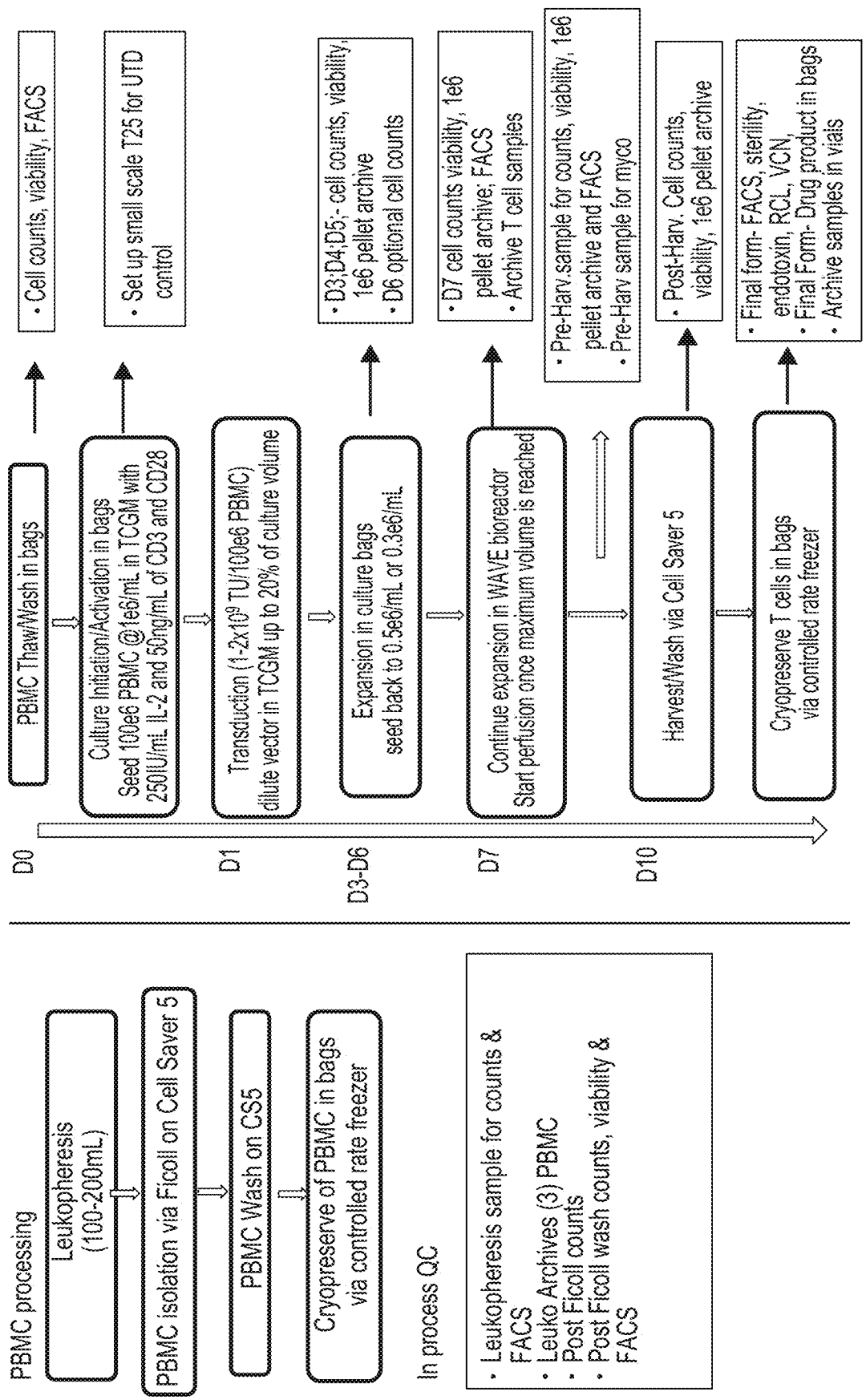
FIG. 11 shows a flowchart of the T cell manufacturing platform using frozen PBMCs, cell culture bags, and optionally a WAVE bioreactor.
Figure 12:
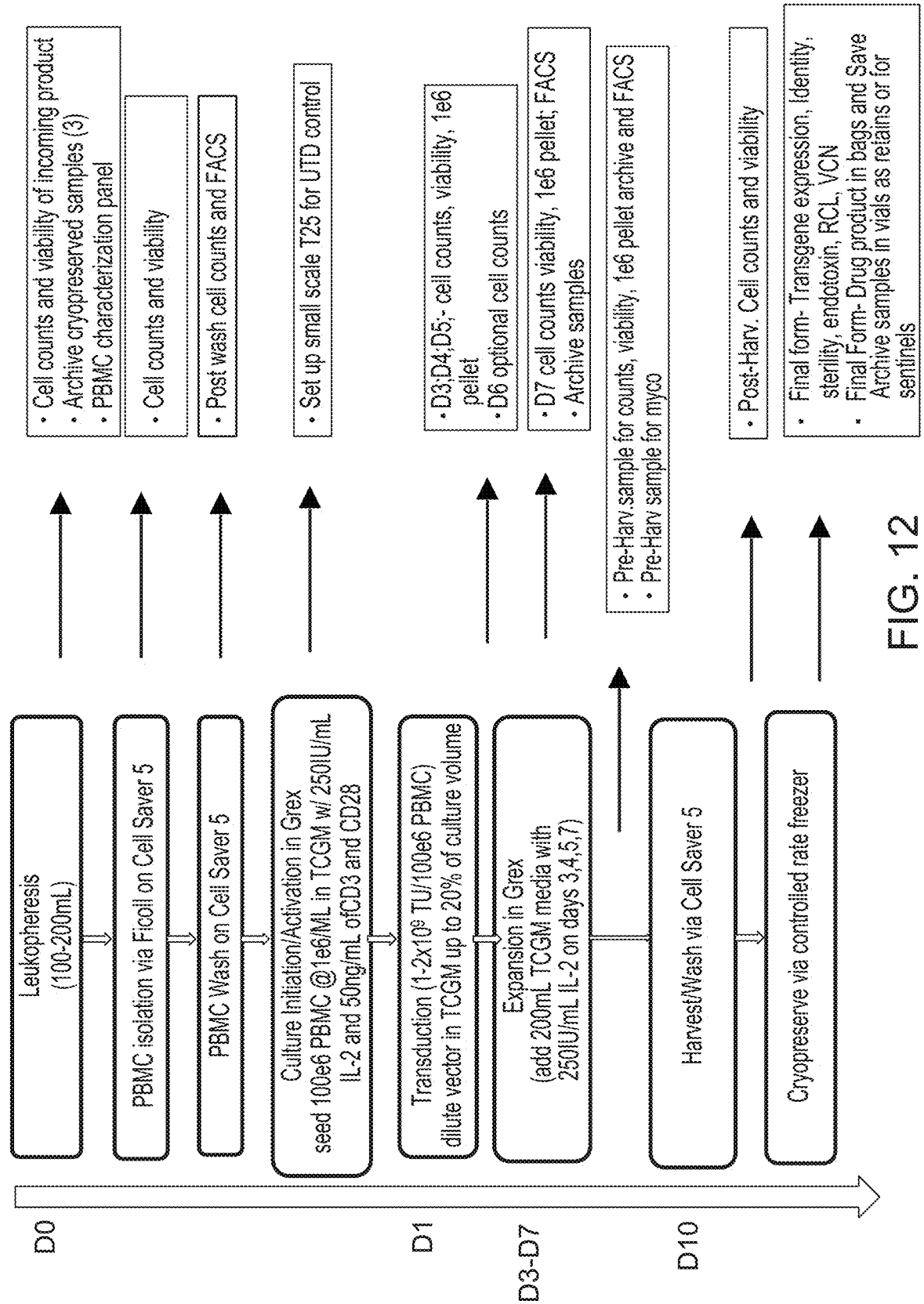
FIG. 12 shows a flowchart of the T cell manufacturing platform using fresh PBMCs, and a GREX bioreactor.

FIG. 9 shows a flowchart comparison of the small-scale research T cell manufacturing platform and the scaled up clinical cGMP dug manufacturing platform. CAR T cells were manufactured using the procedures outlined in Example 1. For large-scale manufacturing, e.g., FIGS. 10-12, CAR T cells were manufactured as follows:

Harvest.

Cells were harvested by leukapheresis using a Spectra Optia® Apheresis System or equivalent. Starting volumes of leukapheresis products used in the manufacturing process were about 100 mL to about 200 mL. Aliquots of the cells were counted, viability determined, cryopreserved, and characterized for PBMCs using FACS analysis.

Isolation.

PBMCs were isolated using a closed system FICOLL™ gradient on the Cell Saver® 5+ Autologous Blood Recovery System (Haemonetics). Post FICOLL™, the buffy coat was washed with CliniMACS buffer w/2% HABS and then resuspended in TCGM with 250 IU IU/mL IL-2. Pre- and post-wash cell counts, viability, and PBMC FACS analysis were performed.

Cryopreservation.

Particular embodiments of the large-scale manufacturing method comprise cryopreservation of the PBMCs after isolation and prior to any further downstream manufacturing. PBMCs are cryopreserved in TCFM and frozen in a controlled rate freezer at a temperature of about −80° C. to about −135° C. at a rate of 1° per minute in a controlled rate freezer and stored in the vapor phase of a liquid nitrogen storage tank.

DAY 0: Culture Initiation/Activation—Bags, Fresh Cells.

$1 \times 10^6$ PBMCs at a density of $1 \times 10^6$ PBMCs/mL in TCGM with 250 IU/mL IL-2 were seeded into 100 mL MACS® GMP Cell Differentiation Bags. PBMCs were activated by adding 50 ng/mL of anti-CD3 antibody and 50 ng/mL of anti-CD28 antibody to the culture and cultured for about 24 hours.

DAY 0: Culture Initiation/Activation—Bags, Frozen Cells.

Particular embodiments of the large-scale manufacturing process comprise using frozen PBMCs. Frozen PBMCs are thawed in a 37° C. water bath and washed in TCGM with 250 IU/mL IL-2. $1 \times 10^8$ thawed PBMCs in TCGM with 250 IU/mL IL-2 were seeded into 100 mL MACS® GMP Cell Differentiation Bags. Thawed PBMCs were activated by adding 50 ng/mL of anti-CD3 antibody and 50 ng/mL of anti-CD28 antibody to the culture and cultured for about 24 hours.

DAY 0: Culture Initiation/Activation—GREX Bioreactor.

Particular embodiments of the large-scale manufacturing process comprise manufacturing T cells in a GREX bioreactor. $1 \times 10^8$ PBMCs in TCGM with 250 IU/mL IL-2 were seeded in 100 mL of TCGM into a GREX-100. PBMCs were activated by adding 50 ng/mL of anti-CD3 antibody and 50 ng/mL of anti-CD28 antibody to the culture and cultured for about 24 hours.

Day 1: Transduction.

Activated cells were transduced with $1-2 \times 10^9$ TU of lentivirus/$10^8$ PBMCs. Lentivirus was diluted in TCGM to 20% of the culture volume. For example if the culture volume was 100 mL TCGM, the virus was diluted in TCGM to yield a maximum volume of 20 mL added to the culture. Cells were transduced for about 48 hours.

Day 3 to Day 10: Expansion.

Transduced cells are expanded in TCGM containing 250 IU/mL of IL-2 for 5 to 8 days. At each of the one or more days of expansion, aliquots of the cells were optionally taken and cells were counted, viability determined, cryopreserved, and characterized for PBMCs using FACS analysis. Cultures were reseeded as necessary at a density of $0.3 \times 10^6$ PBMCs/mL to $0.5 \times 10^6$ PBMCs/mL in order to keep the cells growing in log phase. For cell culture bag-based manufacturing, at Day 7 cells were optionally transferred to a WAVE bioreactor until Day 10 to allow for further expansion. In one embodiment, cell counts were done on days 3, 4, 5, 6, 7, 8 and/or 9 and/or 10. In one embodiment, if the cells are not reaching target levels of expansion by day 7 then they can be transferred to WAVE bioreactor with perfusion of media at 2 L/day for days 8 and 9 to allow for increased expansion.

For GREX-based manufacturing, cells were continuously cultured in the GREX bioreactor for the entire expansion period.

Day 10: Recovery and Cryopreservation.

Expanded cells were recovered and washed on a Cell Saver® 5+ Autologous Blood Recovery System. Cells were washed with 2 L of 0.9% NaCl and then a final wash was performed with PlasmaLyte. Pre- and post-recovery cell counts, viability, and FACS analysis were performed to determine purity and identity of the CAR T cells. Recovered cells were optionally cryopreserved in 50% plasmalyte and 50% Cryostor 10; 50/40/10 (XVIVO/HABS/DMSO); or Cryostor 10 and frozen in a controlled rate freezer at a temperature of about −80° C. to about −135° C. at a rate of 1 per minute in a controlled rate freezer and stored in the vapor phase of a liquid nitrogen storage tank.

Figure 13:
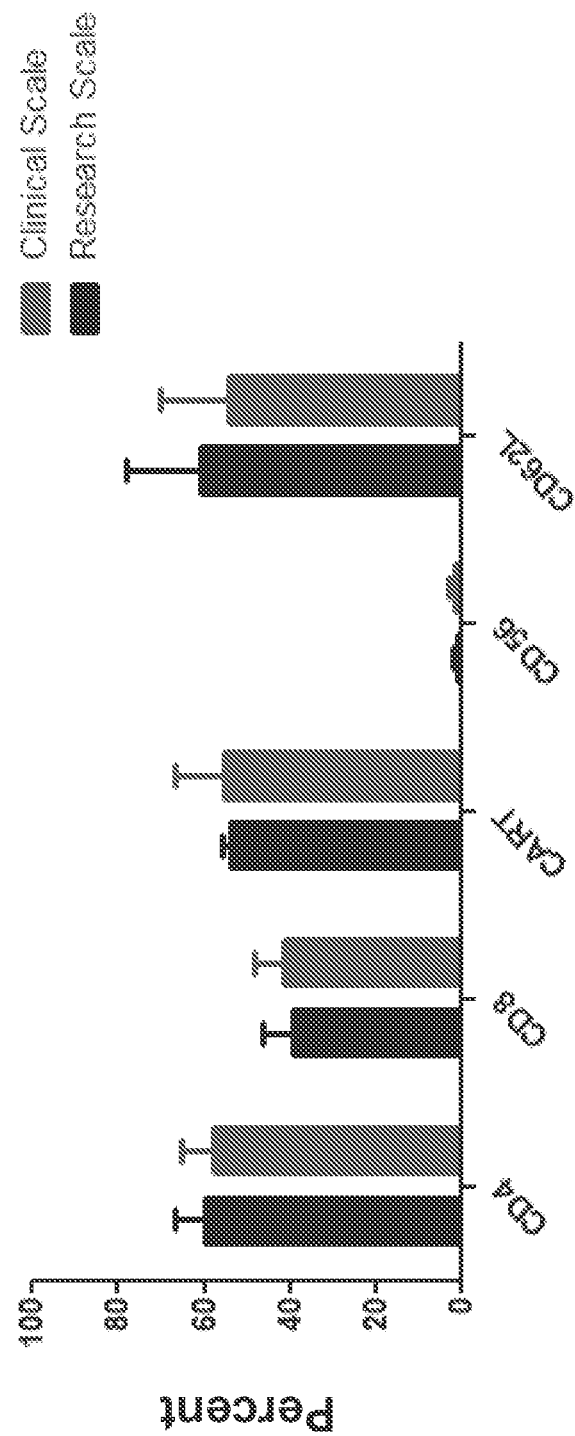
FIG. 13 shows a representative experiment comparing the phenotypes of final manufactured CAR T cell products from small-scale and large-scale manufacturing methods. FACS analysis for expression of CD4, CD8, CAR T construct, CD56, and CD62L cell surface markers did not identify any significant differences in phenotype of the final CAR T products between platforms. $p>0.20$ for all surface markers between the two platforms. (n=3).

2. Cell Phenotypes are Comparable in Final Cell Products Between Small-Scale and Large-Scale Manufacturing Methods CAR T cells were manufactured using small-scale methods described in Example 1 and the large-scale methods described in Example 2, supra. The final cell products were subjected to FACS analysis for expression of CD4, CD8, CAR T construct, CD56, and CD62L cell surface markers to determine any differences in the cell composition of the final product. No significant differences in phenotype of the final CAR T products between the research and clinical scale platforms were observed. $p \geq 0.20$ for all surface markers between the two platforms. (n=3). FIG. 13.

3. Simplified Cell Processing for PBMC Isolation & T Cell Harvest

One of the chief advantages of the manufacturing methods contemplated herein is the implementation of closed system processing steps. PBMCs were harvested by leukapheresis and isolated and washed using a Cell Saver® 5+ Autologous Blood Recovery System (Haemonetics). The Cell Saver® 5+ was also used for the recovery and washing of the final manufactured CAR T cell products.

Figure 14:
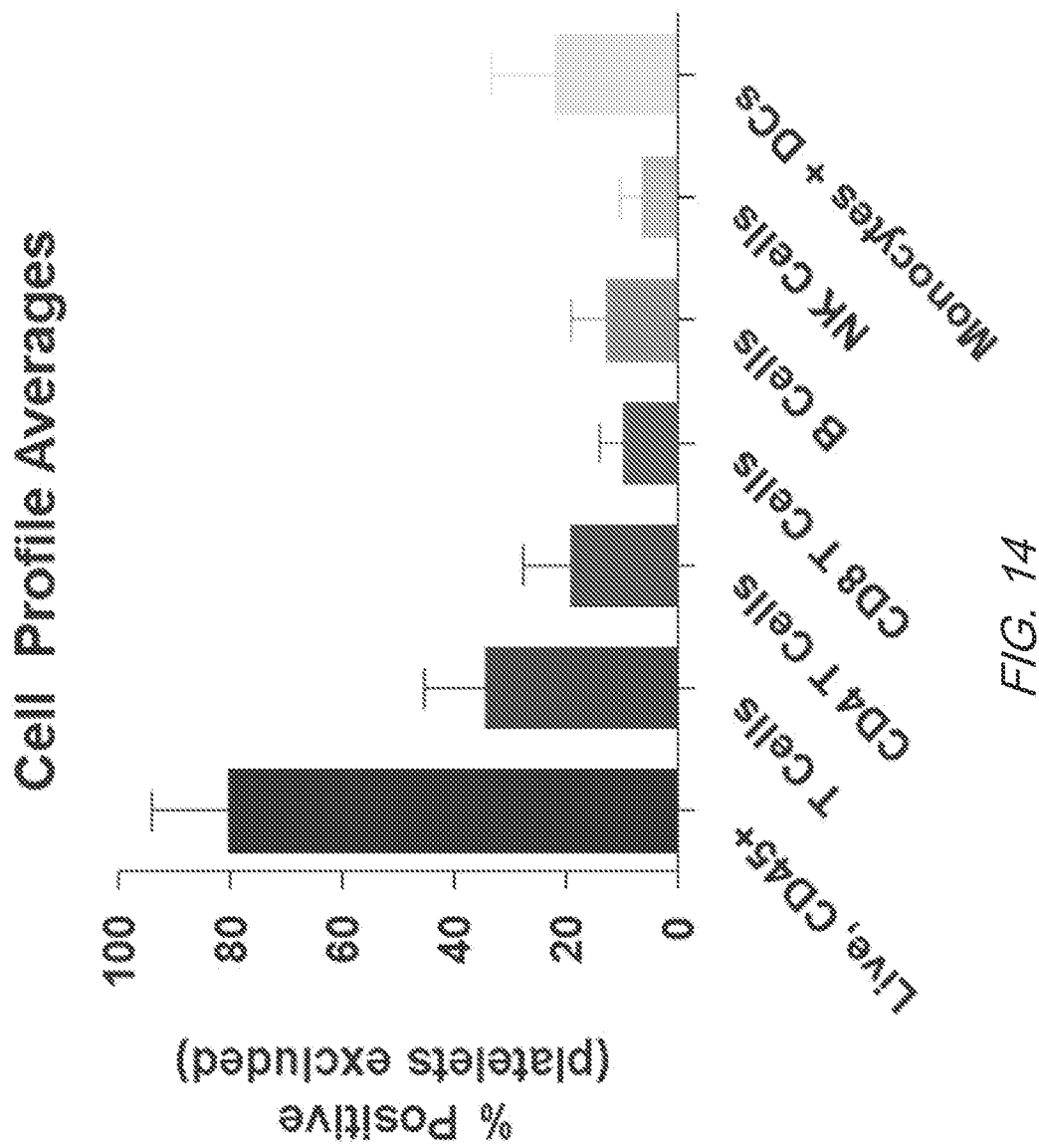
FIG. 14 shows the cellular composition of PBMCs from 18 donors from using a FICOLL™ isolation and washing performed on the Cell Saver® 5+Autologous Blood Recovery System (Haemonetics). The resulting cell populations were characterized by FACS for $CD45^+$ cells, T cells, $CD4^+$ T cells, $CD8^+$ T cells, B cells, NK cells, and monocytes and dendritic cells. The cell profiles were consistent among the 18 donors.
Figure 15A:
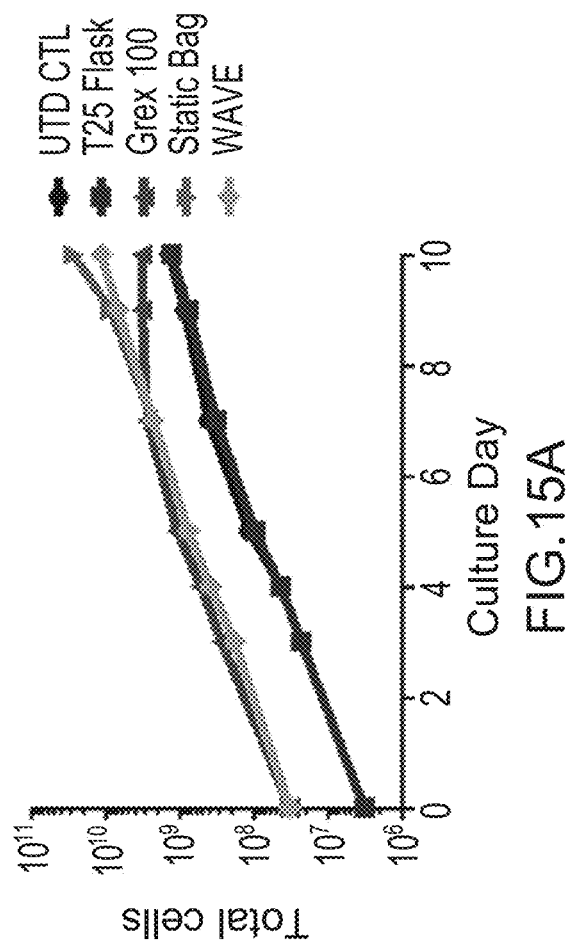
FIG. 15 shows that CAR T cells manufacturing using different methods produced compared final cell products. CAR T cells were manufactured using small-scale (T25 flask) and large-scale (GREX100, static cell culture bags, and WAVE bioreactor) devices. The cell growth rates and expanded cell numbers over a 10 day culture period were comparable among the methods. (A). FACS analysis showed that the amount of $CD3^+$ cells was consistent between the manufacturing methods. (B). qPCR showed that the VCN of the CD3+ cells was comparable among the various manufacturing methods tested.
Figure 15B:
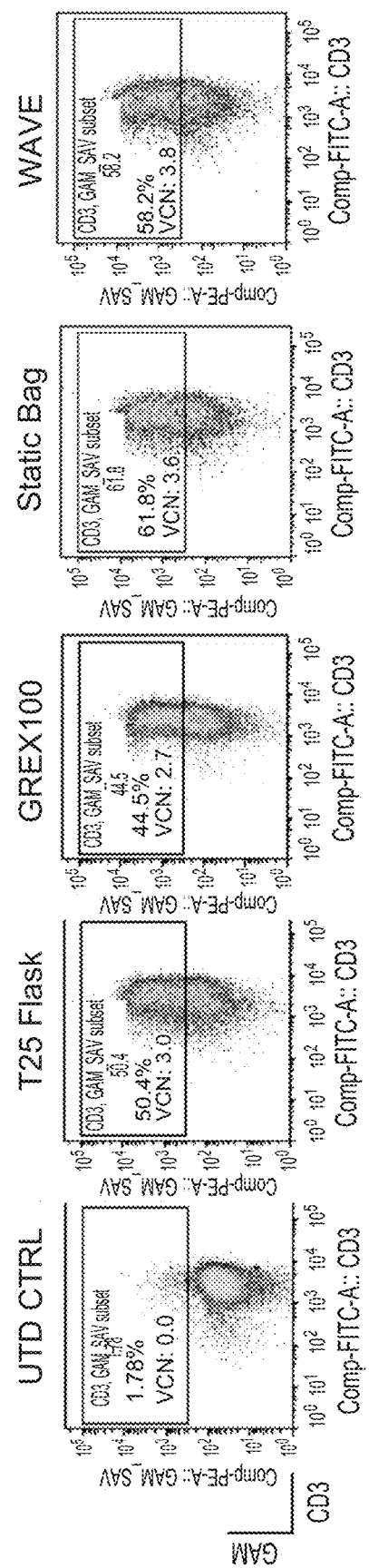

The final PBMC and CAR T products were characterized over multiple experiment (n=18) to demonstrate the remarkably consistent purity of the cellular composition of the starting material and final products. FIG. 14. Utilization of the closed system approach simplified manufacturing and minimized the equipment needed for cGMP processing 4. Manufacturing Process Flexibility In order to address patient to patient variability, and ensure that required dose levels of CAR T cells products could be achieved, multiple devices for the expansion of CAR T cells were compared to show the flexibility offered by the contemplated manufacturing process. Small-scale (T25 flask) and large-scale (GREX100, static cell culture bags, and WAVE bioreactor) manufacturing processes were performed as described supra. Cells manufactured by the different manufacturing methods showed comparable growth rates and expanded cell numbers over a 10 day culture period. FIG. 15A. FACS analysis showed that the amount of CD3+/CAR+ cells was consistent between the manufacturing methods. FIG. 15B. In addition, the VCN of the CD3+/CAR+ cells was comparable among the various manufacturing methods tested. FIG. 15B. These results demonstrate that the contemplated T cell manufacturing methods were flexible and produced comparable final cell products.

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method for manufacturing a human T cell therapeutic for a subject comprising:
   a) obtaining a population of human peripheral blood mononuclear cells (PBMCs) from the subject, wherein the PBMCs comprise CD4+ T cells, CD8+ T cells, and antigen presenting cells (APCs);
   b) culturing the population of PBMCs of step a) for about 20 hours to about 24 hours prior to transduction in a cell culture medium comprising i) one or more cytokines, ii) a soluble anti-CD3 antibody or CD3-binding fragment thereof, and iii) a soluble anti-CD28 antibody or a CD28-binding fragment thereof, thereby producing activated T cells;
   c) transducing the population of PBMCs of step b) comprising activated T cells with a lentiviral vector comprising a polynucleotide encoding an anti-B cell maturation antigen (BCMA) chimeric antigen receptor (CAR), thereby producing transduced T cells; and
   d) culturing the population of PBMCs of step c) in a cell growth medium to expand the number of the transduced T cells,
   thereby manufacturing the human T cell therapeutic for the subject.

2. The method of claim 1, wherein obtaining the population of PBMCs comprises leukapheresis.

3. The method of claim 1, wherein obtaining the population of PBMCs of step a) comprises sedimentation.

4. The method of claim 3, wherein the sedimentation comprises a density gradient.

5. The method of claim 3, wherein the sedimentation is performed using a semiautomated flowthrough centrifuge or a counter-flow centrifugal elutriation device.

6. The method of claim 1, further comprising washing the population of PBMCs of any one or more of steps (a), (b), (c), or (d), in a buffer or cell culture medium.

7. The method of claim 6, wherein the population of PBMCs are washed in T cell growth medium (TCGM) containing one or more cytokines.

8. The method of claim 7, wherein the one or more cytokines in the TCGM are selected from the group consisting of: IL-2, IL-7, IL-15, IL-9, and IL-21.

9. The method of claim 8, wherein the cytokine is IL-2.

10. The method of claim 9, wherein the concentration of IL-2 is about 250 IU/mL.

11. The method of claim 1, wherein the population of PBMCs of step (a) is cryopreserved in a controlled rate freezer.

12. The method of claim 11, wherein the cryopreserved population of PBMCs is thawed.

13. The method of claim 1, wherein the population of PBMCs is seeded for culturing in step (b) in TCGM at a density of about 1×10$^6$ cells/mL.

14. The method of claim 13, wherein the TCGM comprises one or more cytokines selected from the group consisting of: IL-2, IL-7, IL-15, IL-9, and IL-21.

15. The method of claim 14, wherein the one or more cytokines are selected from the group consisting of: IL-2, IL-7, and IL-15.

16. The method of claim 14, wherein the one or more cytokines comprise IL-2.

17. The method of claim 14, wherein the concentration of the one or more cytokines is about 250 IU/mL.

18. The method of claim 13, wherein about $1\times10^9$ transducing units (TU) to about $2\times10^9$ TU of the lentiviral vector are used to transduce $1\times10^8$ seeded cells.

19. The method of claim 1, wherein steps (b)-(d) are in a cell culture bag or a bioreactor.

20. The method of claim 1, wherein the concentration of the anti-CD3 antibody is about 50 ng/mL.

21. The method of claim 1, wherein the concentration of the anti-CD28 antibody is about 50 ng/mL.

22. The method of claim 1, wherein the lentiviral vector is diluted to 20% v/v of the total culture volume.

23. The method of claim 1, wherein the lentiviral vector is diluted to about 40% to about 50% v/v of the total culture volume.

24. The method of claim 1, wherein the population of PBMCs of step (c) is transduced for about 18 to about 48 hours.

25. The method of claim 1, wherein the population of PBMCs of step (c) is transduced for about 18 to about 36 hours.

26. The method of claim 1, wherein the population of PBMCs of step (c) is transduced for about 24 hours.

27. The method of claim 1, wherein the number of transduced T cells is expanded at least 50-fold or at least 100-fold during the culture of step d).

28. The method of claim 1, wherein the number of transduced T cells is expanded at least 200-fold, at least 300-fold, at least 400-fold, at least 500-fold, or at least 600-fold, during the culture of step d).

29. The method of claim 1, wherein the one or more cytokines in the cell culture medium of step (b) is IL-2.

30. The method of claim 1, wherein the PBMCs further comprise natural killer (NK) cells, B cells, monocytes and dendritic cells.

31. A method for manufacturing a human T cell therapeutic comprising:
a) providing a population of autologous human peripheral blood mononuclear cells (PBMCs) comprising CD4+ T cells, CD8+ T cells, and antigen presenting cells (APCs);
b) culturing the population of PBMCs of step a) for about 20 hours to about 24 hours prior to transduction in a cell culture medium comprising i) one or more cytokines, ii) a soluble anti-CD3 antibody or CD3-binding fragment thereof, and iii) a soluble anti-CD28 antibody or a CD28-binding fragment thereof, thereby producing activated T cells;
c) transducing the population of PBMCs of step b) comprising activated T cells with a lentiviral vector comprising a polynucleotide encoding an anti-B cell maturation antigen (BCMA) chimeric antigen receptor (CAR), thereby producing transduced T cells; and
d) culturing the population of PBMCs of step c) in a cell growth medium to expand the number of the transduced T cells, thereby manufacturing the human T cell therapeutic.

32. The method of claim 31, wherein the population of autologous human PBMCs is obtained from whole blood.

33. The method of claim 32, wherein the whole blood is processed by leukapheresis to obtain the autologous human PBMCs.

34. The method of claim 31, wherein the one or more cytokines in the cell culture medium of step (b) is IL-2.

35. The method of claim 31, wherein the PBMCs further comprise natural killer (NK) cells, B cells, monocytes and dendritic cells.

* * * * *

```
                        SEQUENCE LISTING

<160> NUMBER OF SEQ ID NOS: 13

<210> SEQ ID NO 1
    <211> LENGTH: 5
    <212> TYPE: PRT
    <213> ORGANISM: Artificial Sequence
    <220> FEATURE:
    <223> OTHER INFORMATION: Flexible peptide linker

<400> SEQUENCE: 1

Asp Gly Gly Gly Ser
    1               5

<210> SEQ ID NO 2
    <211> LENGTH: 5
    <212> TYPE: PRT
    <213> ORGANISM: Artificial Sequence
    <220> FEATURE:
    <223> OTHER INFORMATION: Flexible peptide linker

<400> SEQUENCE: 2

Thr Gly Glu Lys Pro
    1               5

<210> SEQ ID NO 3
    <211> LENGTH: 4
    <212> TYPE: PRT
    <213> ORGANISM: Artificial Sequence
    <220> FEATURE:
    <223> OTHER INFORMATION: Flexible peptide linker

<400> SEQUENCE: 3

Gly Gly Arg Arg
    1

<210> SEQ ID NO 4
    <211> LENGTH: 5
    <212> TYPE: PRT
    <213> ORGANISM: Artificial Sequence
    <220> FEATURE:
    <223> OTHER INFORMATION: Flexible peptide linker

<400> SEQUENCE: 4

Gly Gly Gly Gly Ser
    1               5

<210> SEQ ID NO 5
    <211> LENGTH: 14
    <212> TYPE: PRT
    <213> ORGANISM: Artificial Sequence
    <220> FEATURE:
    <223> OTHER INFORMATION: Flexible peptide linker

<400> SEQUENCE: 5
```

```
Glu Gly Lys Ser Ser Gly Ser Gly Ser Glu Ser Lys Val Asp
1               5                   10
```

```
<210> SEQ ID NO 6
<211> LENGTH: 18
<212> TYPE: PRT
<213> ORGANISM: Artificial Sequence
<220> FEATURE:
<223> OTHER INFORMATION: Flexible peptide linker

<400> SEQUENCE: 6
```

```
Lys Glu Ser Gly Ser Val Ser Ser Glu Gln Leu Ala Gln Phe Arg Ser
1               5                   10                  15

Leu Asp
```

```
<210> SEQ ID NO 7
<211> LENGTH: 8
<212> TYPE: PRT
<213> ORGANISM: Artificial Sequence
<220> FEATURE:
<223> OTHER INFORMATION: Flexible peptide linker

<400> SEQUENCE: 7
```

```
Gly Gly Arg Arg Gly Gly Gly Ser
1               5
```

```
<210> SEQ ID NO 8
<211> LENGTH: 9
<212> TYPE: PRT
<213> ORGANISM: Artificial Sequence
<220> FEATURE:
<223> OTHER INFORMATION: Flexible peptide linker

<400> SEQUENCE: 8
```

```
Leu Arg Gln Arg Asp Gly Glu Arg Pro
1               5
```

```
<210> SEQ ID NO 9
<211> LENGTH: 12
<212> TYPE: PRT
<213> ORGANISM: Artificial Sequence
<220> FEATURE:
<223> OTHER INFORMATION: Flexible peptide linker

<400> SEQUENCE: 9
```

```
Leu Arg Gln Lys Asp Gly Gly Gly Ser Glu Arg Pro
1               5                   10
```

```
<210> SEQ ID NO 10
<211> LENGTH: 16
<212> TYPE: PRT
<213> ORGANISM: Artificial Sequence
<220> FEATURE:
<223> OTHER INFORMATION: Flexible peptide linker

<400> SEQUENCE: 10
```

```
Leu Arg Gln Lys Asp Gly Gly Gly Ser Gly Gly Gly Ser Glu Arg Pro
1               5                   10                  15
```

```
<210> SEQ ID NO 11
<211> LENGTH: 7
<212> TYPE: PRT
<213> ORGANISM: Artificial Sequence
<220> FEATURE:
<223> OTHER INFORMATION: Polypeptide cleavage sequences
<220> FEATURE:
<221> NAME/KEY: MISC_FEATURE
```

```
<222> LOCATION: (2)..(3)
<223> OTHER INFORMATION: Xaa = Any amino acid
<220> FEATURE:
<221> NAME/KEY: MISC_FEATURE
<222> LOCATION: (5)..(5)
<223> OTHER INFORMATION: Xaa = Any amino acid
<220> FEATURE:
<221> NAME/KEY: MISC_FEATURE
<222> LOCATION: (7)..(7)
<223> OTHER INFORMATION: Xaa  is Gly or Ser

<400> SEQUENCE: 11

Glu Xaa Xaa Tyr Xaa Gln Xaa
1               5

<210> SEQ ID NO 12
<211> LENGTH: 7
<212> TYPE: PRT
<213> ORGANISM: Artificial Sequence
<220> FEATURE:
<223> OTHER INFORMATION: Polypeptide cleavage sequences

<400> SEQUENCE: 12

Glu Asn Leu Tyr Phe Gln Gly
1               5

<210> SEQ ID NO 13
<211> LENGTH: 7
<212> TYPE: PRT
<213> ORGANISM: Artificial Sequence
<220> FEATURE:
<223> OTHER INFORMATION: Polypeptide cleavage sequences

<400> SEQUENCE: 13

Glu Asn Leu Tyr Phe Gln Ser
1               5
```